US012702606B2

(12) United States Patent
Grey et al.

(10) Patent No.: US 12,702,606 B2
(45) Date of Patent: Aug. 11, 2026

(54) BED SNORE SENSOR FOR DETECTING SIGNAL INDICATIVE OF A SNORE

(71) Applicant: Sleep Number Corporation, Minneapolis, MN (US)

(72) Inventors: Dominic Grey, Brooklyn Park, MN (US); John Waite, Bloomington, MN (US); Ramazan Demirli, San Jose, CA (US); Omid Sayadi, San Jose, CA (US); Steven Jay Young, Los Gatos, CA (US); Shawn Barr, San Jose, CA (US); Alan Luckow, Ben Lomond, CA (US)

(73) Assignee: Sleep Number Corporation

( * ) Notice: Subject to any disclaimer, the term of this patent is extended or adjusted under 35 U.S.C. 154(b) by 391 days.

(21) Appl. No.: 18/221,056

(22) Filed: Jul. 12, 2023

(65) Prior Publication Data

US 2024/0041677 A1 Feb. 8, 2024

Related U.S. Application Data

(63) Continuation of application No. 16/233,343, filed on Dec. 27, 2018, now Pat. No. 11,737,938.

(Continued)

(51) Int. Cl.
*A61G 7/018* (2006.01)
*A47C 21/00* (2006.01)

(Continued)

(52) U.S. Cl.
CPC ............ *A61G 7/018* (2013.01); *A47C 21/003* (2013.01); *A61B 5/0205* (2013.01);

(Continued)

(58) Field of Classification Search
CPC .... A61G 7/018; A61G 7/015; A61G 7/05769; A47C 21/003; A47C 27/083;

(Continued)

(56) References Cited

U.S. PATENT DOCUMENTS 3,727,606 A 4/1973 Sielaff
3,795,019 A * 3/1974 Fragas ................ A47C 27/002 5/722

(Continued)

FOREIGN PATENT DOCUMENTS

CN 1557270 12/2004
CN 101224149 7/2008

(Continued)

OTHER PUBLICATIONS

U.S. Appl. No. 16/719,177, filed Dec. 18, 2019, Nunn et al.

(Continued)

*Primary Examiner* — Myles A Throop
(74) *Attorney, Agent, or Firm* — Norton Rose Fulbright US LLP

(57) ABSTRACT

A system can include a foundation structure and a sensor. The foundation structure can have a plurality of deck panels configured to support a mattress. The plurality of deck panels can include a head panel. The plurality of deck panels can have a head, a foot, a first side, and a second side, a first edge along the head, a second edge along the foot opposite of the first edge, a third edge along the first side, and a fourth edge along the second side opposite the third edge. The sensor can be configured to detect a sound indicative of a snore. The sensor can be positioned along the third edge or fourth edge of the head panel.

33 Claims, 30 Drawing Sheets

Related U.S. Application Data

(60) Provisional application No. 62/611,456, filed on Dec. 28, 2017.

(51) Int. Cl.

| | |
|---|---|
| ***A47C 27/08*** | (2006.01) |
| ***A47C 31/00*** | (2006.01) |
| ***A61B 5/00*** | (2006.01) |
| ***A61B 5/0205*** | (2006.01) |
| ***A61B 5/024*** | (2006.01) |
| ***A61B 5/08*** | (2006.01) |
| ***A61B 5/11*** | (2006.01) |
| ***A61B 7/00*** | (2006.01) |
| ***A61G 7/015*** | (2006.01) |
| ***A61G 7/057*** | (2006.01) |

(52) U.S. Cl.
CPC .......... *A61B 5/4809* (2013.01); *A61B 5/6891* (2013.01); *A61B 5/6892* (2013.01); *A61B 7/003* (2013.01); *A61G 7/015* (2013.01); *A47C 27/083* (2013.01); *A47C 31/008* (2013.01); *A61B 5/002* (2013.01); *A61B 5/024* (2013.01); *A61B 5/0816* (2013.01); *A61B 5/11* (2013.01); *A61B 5/4812* (2013.01); *A61B 5/4815* (2013.01); *A61B 5/4818* (2013.01); *A61B 5/7267* (2013.01); *A61B 2560/0242* (2013.01); *A61B 2562/0204* (2013.01); *A61B 2562/0247* (2013.01); *A61G 7/05769* (2013.01)

(58) Field of Classification Search
CPC ... A47C 31/008; A61B 5/0205; A61B 5/4809; A61B 5/6891; A61B 5/6892; A61B 7/003; A61B 5/002; A61B 5/024; A61B 5/0816; A61B 5/11; A61B 5/4812; A61B 5/4815; A61B 5/4818; A61B 5/7267; A61B 2560/0242; A61B 2562/0204; A61B 2562/0247
USPC .............................................................. 5/482
See application file for complete search history.

(56) References Cited

U.S. PATENT DOCUMENTS 3,799,161 A * 3/1974 Collins .................. A61B 46/00 128/854
3,998,209 A 12/1976 Macvaugh
4,146,885 A 3/1979 Lawson, Jr.
4,299,233 A 11/1981 Lemelson
4,644,330 A * 2/1987 Dowling ................ H03K 17/94 128/204.23
4,657,026 A 4/1987 Tagg
4,662,012 A 5/1987 Tarbet
4,766,628 A 8/1988 Greer et al.
4,788,729 A 12/1988 Greer et al.
D300,194 S 3/1989 Walker
4,829,616 A 5/1989 Walker
4,890,344 A 1/1990 Walker
4,897,890 A 2/1990 Walker
4,908,895 A 3/1990 Walker
D313,973 S 1/1991 Walker
4,982,466 A 1/1991 Higgins et al.
4,991,244 A 2/1991 Walker
5,020,176 A 6/1991 Dotson
5,062,169 A 11/1991 Kennedy et al.
5,144,706 A 9/1992 Walker et al.
5,170,522 A 12/1992 Walker
5,197,490 A 3/1993 Steiner et al.
5,444,786 A 8/1995 Raviv
5,459,452 A 10/1995 DePonte
5,487,196 A 1/1996 Wilkinson et al.
D368,475 S 4/1996 Scott
5,509,154 A 4/1996 Shafer et al.
5,515,865 A 5/1996 Scanlon
5,564,140 A 10/1996 Shoenhair et al.
5,642,540 A * 7/1997 Culver .................. A47C 21/06 5/490
5,642,546 A 7/1997 Shoenhair
5,652,484 A 7/1997 Shafer et al.
5,675,855 A 10/1997 Culp
5,684,460 A 11/1997 Scanlon
5,699,038 A 12/1997 Ulrich et al.
5,724,990 A 3/1998 Ogino
5,765,246 A 6/1998 Shoenhair
5,771,511 A 6/1998 Kummer et al.
5,796,340 A 8/1998 Miller
5,844,488 A 12/1998 Musick
5,844,996 A 12/1998 Enzmann et al.
5,848,450 A 12/1998 Oexman et al.
5,903,941 A 5/1999 Shafer et al.
5,904,172 A 5/1999 Gifft et al.
5,948,303 A 9/1999 Larson
5,964,720 A 10/1999 Pelz
5,989,193 A 11/1999 Sullivan
6,024,699 A 2/2000 Surwit et al.
6,037,723 A 3/2000 Shafer et al.
6,058,537 A 5/2000 Larson
6,062,216 A 5/2000 Corn
6,079,065 A 6/2000 Luff et al.
6,094,762 A 8/2000 Viard et al.
6,108,844 A 8/2000 Kraft et al.
6,120,441 A 9/2000 Griebel
6,146,332 A 11/2000 Pinsonneault et al.
6,147,592 A 11/2000 Ulrich et al.
6,161,231 A 12/2000 Kraft et al.
6,202,239 B1 3/2001 Ward et al.
6,208,250 B1 3/2001 Dixon et al.
6,234,642 B1 5/2001 Bokaemper
6,272,378 B1 8/2001 Baumgart-Schmitt
6,298,855 B1 * 10/2001 Baird ..................... A61B 46/00 128/853
6,386,201 B1 5/2002 Fard
6,396,224 B1 5/2002 Luff et al.
6,397,419 B1 6/2002 Mechache
6,438,776 B2 8/2002 Ferrand et al.
6,450,957 B1 9/2002 Yoshimi et al.
6,468,234 B1 10/2002 Ford et al.
6,483,264 B1 11/2002 Shafer et al.
6,485,441 B2 11/2002 Woodward
6,546,580 B2 4/2003 Shimada
6,547,743 B2 4/2003 Brydon
6,561,047 B1 5/2003 Gladney
6,566,833 B2 * 5/2003 Bartlett ................ A61G 7/0524 318/564
6,640,362 B1 * 11/2003 Kimball ............... A47G 9/0223 128/854
6,643,875 B2 11/2003 Boso et al.
6,686,711 B2 2/2004 Rose et al.
6,698,432 B2 3/2004 Ek
6,708,357 B2 3/2004 Gaboury et al.
6,719,708 B1 4/2004 Jansen
6,763,541 B2 7/2004 Mahoney et al.
6,778,090 B2 8/2004 Newham
6,804,848 B1 10/2004 Rose
6,832,397 B2 12/2004 Gaboury
6,840,117 B2 1/2005 Hubbard, Jr.
6,840,907 B1 1/2005 Brydon
6,847,301 B1 1/2005 Olson
D502,929 S 3/2005 Copeland et al.
6,878,121 B2 4/2005 Krausman
6,883,191 B2 4/2005 Gaboury et al.
6,993,380 B1 1/2006 Modarres
7,041,049 B1 5/2006 Raniere
7,077,810 B2 7/2006 Lange et al.
7,107,638 B2 * 9/2006 Wilson ................. A47G 9/0207 5/923
7,120,952 B1 10/2006 Bass et al.
7,150,718 B2 12/2006 Okada
7,237,287 B2 7/2007 Weismiller et al.
7,253,366 B2 8/2007 Bhai
7,304,580 B2 12/2007 Sullivan et al.

(56) References Cited

U.S. PATENT DOCUMENTS 7,314,451 B2 1/2008 Halperin et al.
7,321,811 B1 1/2008 Rawls-Meehan
7,330,127 B2 2/2008 Price et al.
7,389,554 B1 6/2008 Rose
7,396,331 B2 7/2008 Mack
7,429,247 B2 9/2008 Okada et al.
7,437,787 B2 10/2008 Bhai
7,465,280 B2 12/2008 Rawls-Meehan
7,480,951 B2 1/2009 Weismiller
7,506,390 B2 3/2009 Dixon et al.
7,520,006 B2 4/2009 Menkedick et al.
7,522,062 B2 4/2009 Mossbeck
7,524,279 B2 * 4/2009 Auphan ................ G16H 50/30 600/26
7,532,934 B2 5/2009 Lee et al.
7,538,659 B2 5/2009 Ulrich
7,542,959 B2 6/2009 Barnhill et al.
7,568,246 B2 8/2009 Weismiller et al.
7,631,377 B1 12/2009 Sanford
7,637,859 B2 12/2009 Lindback et al.
7,652,581 B2 1/2010 Gentry et al.
7,666,151 B2 2/2010 Sullivan et al.
7,669,263 B2 3/2010 Menkedick et al.
7,676,872 B2 3/2010 Block et al.
7,685,663 B2 3/2010 Rawls-Meehan
7,698,761 B2 4/2010 Neuenswander et al.
7,699,784 B2 4/2010 Wan et al.
7,717,848 B2 5/2010 Heruth et al.
7,749,154 B2 7/2010 Cornel
7,784,128 B2 8/2010 Kramer
7,785,257 B2 8/2010 Mack et al.
7,805,785 B2 10/2010 Rawls-Meehan
7,841,031 B2 11/2010 Rawls-Meehan
7,849,545 B2 12/2010 Flocard et al.
7,854,031 B2 12/2010 Rawls-Meehan
7,860,723 B2 12/2010 Rawls-Meehan
7,862,523 B2 1/2011 Ruotoistenmaki
7,865,988 B2 1/2011 Koughan et al.
7,868,757 B2 1/2011 Radivojevic et al.
7,869,903 B2 1/2011 Turner et al.
7,930,783 B2 4/2011 Rawls-Meehan
7,933,669 B2 4/2011 Rawls-Meehan
7,953,613 B2 5/2011 Gizewski
7,954,189 B2 6/2011 Rawls-Meehan
7,956,755 B2 6/2011 Lee et al.
7,967,739 B2 6/2011 Auphan
7,979,169 B2 7/2011 Rawls-Meehan
8,019,486 B2 9/2011 Rawls-Meehan
8,020,230 B2 9/2011 Rawls-Meehan
8,028,363 B2 10/2011 Rawls-Meehan
8,032,263 B2 10/2011 Rawls-Meehan
8,032,960 B2 10/2011 Rawls-Meehan
8,046,114 B2 10/2011 Rawls-Meehan
8,046,115 B2 10/2011 Rawls-Meehan
8,046,116 B2 10/2011 Rawls-Meehan
8,046,117 B2 10/2011 Rawls-Meehan
8,050,805 B2 11/2011 Rawls-Meehan
8,052,612 B2 11/2011 Tang
8,065,764 B2 11/2011 Kramer
8,069,852 B2 12/2011 Burton
8,073,535 B2 12/2011 Jung et al.
8,078,269 B2 12/2011 Suzuki et al.
8,078,336 B2 12/2011 Rawls-Meehan
8,078,337 B2 12/2011 Rawls-Meehan
8,083,682 B2 12/2011 Dalal et al.
8,090,478 B2 1/2012 Skinner et al.
8,092,399 B2 1/2012 Sasaki
8,094,013 B1 1/2012 Lee
8,096,960 B2 1/2012 Loree et al.
8,144,001 B1 3/2012 D'Souza
8,146,191 B2 4/2012 Bobey et al.
8,150,562 B2 4/2012 Rawls-Meehan
8,166,589 B2 5/2012 Hijlkema
8,181,290 B2 5/2012 Brykalski et al.
8,181,296 B2 5/2012 Rawls-Meehan
8,266,742 B2 9/2012 Andrienko
8,272,892 B2 9/2012 McNeely et al.
8,276,585 B2 10/2012 Buckley
8,279,057 B2 10/2012 Hirose
8,280,748 B2 10/2012 Allen
8,281,433 B2 10/2012 Riley et al.
8,282,452 B2 10/2012 Grigsby et al.
8,284,047 B2 10/2012 Collins, Jr.
8,287,452 B2 10/2012 Young et al.
8,336,369 B2 12/2012 Mahoney
8,341,784 B2 1/2013 Scott
8,341,786 B2 1/2013 Oexman et al.
8,348,840 B2 1/2013 Heit et al.
8,350,709 B2 1/2013 Receveur
8,375,488 B2 2/2013 Rawls-Meehan
8,376,954 B2 2/2013 Lange et al.
8,382,484 B2 2/2013 Wetmore et al.
8,386,008 B2 2/2013 Yuen et al.
8,398,538 B2 3/2013 Dothie
8,403,865 B2 3/2013 Halperin et al.
8,410,942 B2 4/2013 Chacon et al.
8,413,274 B2 4/2013 Weismiller et al.
8,421,606 B2 4/2013 Collins, Jr. et al.
8,428,696 B2 4/2013 Foo
8,444,558 B2 5/2013 Young et al.
8,491,492 B2 7/2013 Shinar et al.
8,517,953 B2 8/2013 Lange et al.
D691,118 S 10/2013 Ingham et al.
8,620,615 B2 12/2013 Oexman
D697,874 S 1/2014 Stusynski et al.
D698,338 S 1/2014 Ingham
D701,536 S 3/2014 Sakal
8,672,853 B2 3/2014 Young
8,679,034 B2 3/2014 Halperin et al.
8,769,747 B2 7/2014 Mahoney et al.
8,832,887 B2 9/2014 Mossbeck
8,840,564 B2 9/2014 Pinhas et al.
8,880,207 B2 11/2014 Abeyratne et al.
8,893,339 B2 11/2014 Fleury
8,909,357 B2 12/2014 Rawls-Meehan
8,931,329 B2 1/2015 Mahoney et al.
8,966,689 B2 3/2015 McGuire et al.
8,973,183 B1 3/2015 Palashewski et al.
8,984,687 B2 3/2015 Stusynski et al.
8,997,280 B1 * 4/2015 Hannula ............. A47C 31/105 5/500
D737,250 S 8/2015 Ingham et al.
9,131,781 B2 9/2015 Zaiss et al.
9,370,457 B2 6/2016 Nunn et al.
9,392,879 B2 7/2016 Nunn et al.
9,445,751 B2 9/2016 Young et al.
9,504,416 B2 11/2016 Young et al.
9,510,688 B2 12/2016 Nunn et al.
9,635,953 B2 5/2017 Nunn et al.
9,730,524 B2 8/2017 Chen et al.
9,737,154 B2 8/2017 Mahoney et al.
9,770,114 B2 9/2017 Brosnan et al.
9,844,275 B2 12/2017 Nunn et al.
D809,843 S 2/2018 Keeley et al.
D812,393 S 3/2018 Karschnik et al.
9,924,813 B1 3/2018 Basten et al.
9,931,085 B2 4/2018 Young et al.
10,058,467 B2 8/2018 Stusynski et al.
10,092,242 B2 10/2018 Nunn et al.
10,105,092 B2 10/2018 Franceschetti et al.
10,143,312 B2 12/2018 Brosnan et al.
10,149,549 B2 12/2018 Erko et al.
10,182,661 B2 1/2019 Nunn et al.
10,194,752 B2 2/2019 Zaiss et al.
10,194,753 B2 2/2019 Fleury et al.
10,201,234 B2 2/2019 Nunn et al.
10,251,490 B2 4/2019 Nunn et al.
10,342,358 B1 7/2019 Palashewski et al.
10,441,086 B2 10/2019 Nunn et al.
10,441,087 B2 10/2019 Karschnik et al.
10,448,749 B2 10/2019 Palashewski et al.
10,492,969 B2 12/2019 Stusynski et al.
10,632,032 B1 4/2020 Stusynski et al.
10,646,050 B2 5/2020 Nunn et al.

(56) References Cited

U.S. PATENT DOCUMENTS

| | | | | |
|---|---|---|---|---|
| 10,674,832 | B2 | 6/2020 | Brosnan et al. | |
| 10,716,512 | B2 | 7/2020 | Erko et al. | |
| 10,729,253 | B1 | 8/2020 | Gaunt | |
| 10,729,255 | B2 | 8/2020 | Erko et al. | |
| 10,736,432 | B2 | 8/2020 | Brosnan et al. | |
| 10,750,875 | B2 | 8/2020 | Palashewski et al. | |
| 10,827,846 | B2 | 11/2020 | Karschnik et al. | |
| 10,828,007 | B1 * | 11/2020 | Telfort | A61B 5/6833 |
| 10,881,219 | B2 | 1/2021 | Nunn et al. | |
| 10,957,335 | B2 | 3/2021 | Demirli et al. | |
| 10,959,535 | B2 | 3/2021 | Karschnik et al. | |
| D916,745 | S | 4/2021 | Stusynski et al. | |
| 10,980,351 | B2 | 4/2021 | Nunn et al. | |
| 11,096,849 | B2 | 8/2021 | Stusynski et al. | |
| 11,122,909 | B2 | 9/2021 | Palashewski et al. | |
| D932,808 | S | 10/2021 | Keeley | |
| 11,160,683 | B2 | 11/2021 | Nunn et al. | |
| 11,206,929 | B2 | 12/2021 | Palashewski et al. | |
| D954,725 | S | 6/2022 | Stusynski et al. | |
| D968,436 | S | 11/2022 | Stusynski et al. | |
| D975,121 | S | 1/2023 | Stusynski et al. | |
| 11,571,346 | B2 * | 2/2023 | Sayadi | A47C 21/003 |
| D1,000,464 | S | 10/2023 | Stusynski et al. | |
| 12,156,603 | B2 * | 12/2024 | Foucha | A47G 9/0223 |
| 2002/0124311 | A1 | 9/2002 | Peftoulidis | |
| 2002/0144342 | A1 * | 10/2002 | Fruge | A47C 27/088 5/706 |
| 2002/0184711 | A1 | 12/2002 | Mahoney et al. | |
| 2002/0189621 | A1 | 12/2002 | Ek | |
| 2003/0045806 | A1 | 3/2003 | Brydon | |
| 2003/0128125 | A1 | 7/2003 | Burbank et al. | |
| 2003/0163874 | A1 | 9/2003 | Boso et al. | |
| 2003/0166995 | A1 | 9/2003 | Jansen | |
| 2003/0182728 | A1 | 10/2003 | Chapman et al. | |
| 2003/0221261 | A1 | 12/2003 | Tarbet et al. | |
| 2004/0049132 | A1 | 3/2004 | Barron et al. | |
| 2004/0234080 | A1 | 11/2004 | Hernandez | |
| 2005/0022606 | A1 | 2/2005 | Partin et al. | |
| 2005/0038326 | A1 | 2/2005 | Mathur | |
| 2005/0115561 | A1 | 6/2005 | Stahmann et al. | |
| 2005/0190065 | A1 | 9/2005 | Ronholm | |
| 2005/0190068 | A1 | 9/2005 | Gentry et al. | |
| 2005/0283039 | A1 | 12/2005 | Cornel | |
| 2006/0020178 | A1 | 1/2006 | Sotos et al. | |
| 2006/0031996 | A1 | 2/2006 | Rawls-Meehan | |
| 2006/0047217 | A1 | 3/2006 | Mirtalebi | |
| 2006/0152378 | A1 | 7/2006 | Lokhorst | |
| 2006/0162074 | A1 | 7/2006 | Bader | |
| 2006/0198533 | A1 | 9/2006 | Wang et al. | |
| 2007/0049842 | A1 | 3/2007 | Hill et al. | |
| 2007/0118054 | A1 | 5/2007 | Pinhas et al. | |
| 2007/0149883 | A1 | 6/2007 | Yesha | |
| 2007/0179334 | A1 | 8/2007 | Groves et al. | |
| 2007/0180047 | A1 | 8/2007 | Dong et al. | |
| 2007/0180618 | A1 | 8/2007 | Weismiller et al. | |
| 2007/0276202 | A1 | 11/2007 | Raisanen et al. | |
| 2008/0052837 | A1 | 3/2008 | Blumberg | |
| 2008/0071200 | A1 | 3/2008 | Rawls-Meehan | |
| 2008/0077020 | A1 | 3/2008 | Young et al. | |
| 2008/0092291 | A1 | 4/2008 | Rawls-Meehan | |
| 2008/0092292 | A1 | 4/2008 | Rawls-Meehan | |
| 2008/0092293 | A1 | 4/2008 | Rawls-Meehan | |
| 2008/0092294 | A1 | 4/2008 | Rawls-Meehan | |
| 2008/0093784 | A1 | 4/2008 | Rawls-Meehan | |
| 2008/0097774 | A1 | 4/2008 | Rawls-Meehan | |
| 2008/0097778 | A1 | 4/2008 | Rawls-Meehan | |
| 2008/0097779 | A1 | 4/2008 | Rawls-Meehan | |
| 2008/0104750 | A1 | 5/2008 | Rawls-Meehan | |
| 2008/0104754 | A1 | 5/2008 | Rawls-Meehan | |
| 2008/0104755 | A1 | 5/2008 | Rawls-Meehan | |
| 2008/0104756 | A1 | 5/2008 | Rawls-Meehan | |
| 2008/0104757 | A1 | 5/2008 | Rawls-Meehan | |
| 2008/0104758 | A1 | 5/2008 | Rawls-Meehan | |
| 2008/0104759 | A1 | 5/2008 | Rawls-Meehan | |
| 2008/0104760 | A1 | 5/2008 | Rawls-Meehan | |
| 2008/0104761 | A1 | 5/2008 | Rawls-Meehan | |
| 2008/0109959 | A1 | 5/2008 | Rawls-Meehan | |
| 2008/0109964 | A1 | 5/2008 | Flocard et al. | |
| 2008/0109965 | A1 | 5/2008 | Mossbeck | |
| 2008/0115272 | A1 | 5/2008 | Rawls-Meehan | |
| 2008/0115273 | A1 | 5/2008 | Rawls-Meehan | |
| 2008/0115274 | A1 | 5/2008 | Rawls-Meehan | |
| 2008/0115275 | A1 | 5/2008 | Rawls-Meehan | |
| 2008/0115276 | A1 | 5/2008 | Rawls-Meehan | |
| 2008/0115277 | A1 | 5/2008 | Rawls-Meehan | |
| 2008/0115278 | A1 | 5/2008 | Rawls-Meehan | |
| 2008/0115279 | A1 | 5/2008 | Rawls-Meehan | |
| 2008/0115280 | A1 | 5/2008 | Rawls-Meehan | |
| 2008/0115281 | A1 | 5/2008 | Rawls-Meehan | |
| 2008/0115282 | A1 | 5/2008 | Rawls-Meehan | |
| 2008/0120775 | A1 | 5/2008 | Rawls-Meehan | |
| 2008/0120776 | A1 | 5/2008 | Rawls-Meehan | |
| 2008/0120777 | A1 | 5/2008 | Rawls-Meehan | |
| 2008/0120778 | A1 | 5/2008 | Rawls-Meehan | |
| 2008/0120779 | A1 | 5/2008 | Rawls-Meehan | |
| 2008/0120784 | A1 | 5/2008 | Warner et al. | |
| 2008/0122616 | A1 | 5/2008 | Warner | |
| 2008/0126122 | A1 | 5/2008 | Warner et al. | |
| 2008/0126132 | A1 | 5/2008 | Warner | |
| 2008/0127418 | A1 | 6/2008 | Rawls-Meehan | |
| 2008/0127424 | A1 | 6/2008 | Rawls-Meehan | |
| 2008/0147442 | A1 | 6/2008 | Warner | |
| 2008/0162171 | A1 | 7/2008 | Rawls-Meehan | |
| 2008/0262657 | A1 | 10/2008 | Howell et al. | |
| 2008/0275314 | A1 | 11/2008 | Mack et al. | |
| 2008/0281611 | A1 | 11/2008 | Rawls-Meehan | |
| 2008/0281612 | A1 | 11/2008 | Rawls-Meehan | |
| 2008/0281613 | A1 | 11/2008 | Rawls-Meehan | |
| 2008/0288272 | A1 | 11/2008 | Rawls-Meehan | |
| 2008/0288273 | A1 | 11/2008 | Rawls-Meehan | |
| 2008/0304677 | A1 * | 12/2008 | Abolfathi | G10K 11/17875 381/71.1 |
| 2008/0306351 | A1 | 12/2008 | Izumi | |
| 2008/0307582 | A1 | 12/2008 | Flocard et al. | |
| 2009/0018853 | A1 | 1/2009 | Rawls-Meehan | |
| 2009/0018854 | A1 | 1/2009 | Rawls-Meehan | |
| 2009/0018855 | A1 | 1/2009 | Rawls-Meehan | |
| 2009/0018856 | A1 | 1/2009 | Rawls-Meehan | |
| 2009/0018857 | A1 | 1/2009 | Rawls-Meehan | |
| 2009/0018858 | A1 | 1/2009 | Rawls-Meehan | |
| 2009/0024406 | A1 | 1/2009 | Rawls-Meehan | |
| 2009/0037205 | A1 | 2/2009 | Rawls-Meehan | |
| 2009/0043595 | A1 | 2/2009 | Rawls-Meehan | |
| 2009/0064420 | A1 | 3/2009 | Rawls-Meehan | |
| 2009/0100599 | A1 | 4/2009 | Rawls-Meehan | |
| 2009/0121660 | A1 | 5/2009 | Rawls-Meehan | |
| 2009/0139029 | A1 | 6/2009 | Rawls-Meehan | |
| 2009/0203972 | A1 | 8/2009 | Henehgan et al. | |
| 2009/0275808 | A1 | 11/2009 | DiMaio et al. | |
| 2009/0314354 | A1 | 12/2009 | Chaffee | |
| 2010/0025900 | A1 | 2/2010 | Rawls-Meehan | |
| 2010/0090383 | A1 | 4/2010 | Rawls-Meehan | |
| 2010/0094139 | A1 | 4/2010 | Brauers et al. | |
| 2010/0099954 | A1 | 4/2010 | Dickinson et al. | |
| 2010/0152546 | A1 * | 6/2010 | Behan | A61B 5/6887 600/301 |
| 2010/0170043 | A1 | 7/2010 | Young et al. | |
| 2010/0170044 | A1 | 7/2010 | Kao et al. | |
| 2010/0174198 | A1 | 7/2010 | Young et al. | |
| 2010/0174199 | A1 | 7/2010 | Young et al. | |
| 2010/0191136 | A1 | 7/2010 | Wolford | |
| 2010/0199432 | A1 | 8/2010 | Rawls-Meehan | |
| 2010/0231421 | A1 | 9/2010 | Rawls-Meehan | |
| 2010/0302044 | A1 * | 12/2010 | Chacon | A61F 5/56 128/848 |
| 2010/0317930 | A1 | 12/2010 | Oexman et al. | |
| 2011/0001622 | A1 | 1/2011 | Gentry | |
| 2011/0010014 | A1 | 1/2011 | Oexman et al. | |
| 2011/0015495 | A1 | 1/2011 | Dothie et al. | |
| 2011/0041592 | A1 | 2/2011 | Schmoeller et al. | |
| 2011/0068935 | A1 | 3/2011 | Riley et al. | |
| 2011/0087113 | A1 | 4/2011 | Mack et al. | |
| 2011/0094041 | A1 | 4/2011 | Rawls-Meehan | |
| 2011/0115635 | A1 | 5/2011 | Petrovski et al. | |

(56) References Cited

U.S. PATENT DOCUMENTS

2011/0138539 A1 6/2011 Mahoney et al.
2011/0144455 A1 6/2011 Young et al.
2011/0156915 A1 6/2011 Brauers et al.
2011/0163885 A1 7/2011 Poulos et al.
2011/0224510 A1 9/2011 Oakhill
2011/0239374 A1 10/2011 Rawls-Meehan
2011/0252569 A1 10/2011 Rawls-Meehan
2011/0258784 A1 10/2011 Rawls-Meehan
2011/0282216 A1 11/2011 Shinar et al.
2011/0283462 A1 11/2011 Rawls-Meehan
2011/0291795 A1 12/2011 Rawls-Meehan
2011/0291842 A1 12/2011 Oexman
2011/0295083 A1 12/2011 Doelling et al.
2011/0302720 A1 12/2011 Yakam et al.
2011/0306844 A1 12/2011 Young
2012/0017371 A1 1/2012 Pollard
2012/0025992 A1 2/2012 Tallent et al.
2012/0053423 A1 3/2012 Kenalty et al.
2012/0053424 A1 3/2012 Kenalty et al.
2012/0056729 A1 3/2012 Rawls-Meehan
2012/0057685 A1 3/2012 Rawls-Meehan
2012/0057716 A1 3/2012 Chang et al.
2012/0090698 A1 4/2012 Giori et al.
2012/0110738 A1 5/2012 Rawls-Meehan
2012/0110739 A1 5/2012 Rawls-Meehan
2012/0110740 A1 5/2012 Rawls-Meehan
2012/0112890 A1 5/2012 Rawls-Meehan
2012/0112891 A1 5/2012 Rawls-Meehan
2012/0112892 A1 5/2012 Rawls-Meehan
2012/0116591 A1 5/2012 Rawls-Meehan
2012/0119886 A1 5/2012 Rawls-Meehan
2012/0119887 A1 5/2012 Rawls-Meehan
2012/0138067 A1* 6/2012 Rawls-Meehan .... A61G 7/0514 5/616
2012/0154155 A1 6/2012 Brasch
2012/0186019 A1 7/2012 Rawls-Meehan
2012/0198632 A1 8/2012 Rawls-Meehan
2012/0204887 A1 8/2012 Connor
2012/0240340 A1 9/2012 Driscoll et al.
2012/0304391 A1 12/2012 Driscoll et al.
2012/0311790 A1 12/2012 Nomura et al.
2013/0160212 A1 6/2013 Oexman et al.
2013/0174347 A1 7/2013 Oexman et al.
2013/0227787 A1 9/2013 Herbst et al.
2013/0245502 A1 9/2013 Lange et al.
2014/0007656 A1 1/2014 Mahoney
2014/0047644 A1 2/2014 Mossbeck
2014/0137332 A1 5/2014 McGuire et al.
2014/0182061 A1 7/2014 Zaiss
2014/0250597 A1 9/2014 Chen et al.
2014/0257571 A1 9/2014 Chen et al.
2014/0259417 A1 9/2014 Nunn et al.
2014/0259418 A1 9/2014 Nunn et al.
2014/0259419 A1 9/2014 Stusynski
2014/0259431 A1 9/2014 Fleury
2014/0259433 A1 9/2014 Nunn et al.
2014/0259434 A1 9/2014 Nunn et al.
2014/0277611 A1 9/2014 Nunn et al.
2014/0277778 A1 9/2014 Nunn et al.
2014/0277822 A1 9/2014 Nunn et al.
2014/0313700 A1 10/2014 Connell et al.
2015/0007393 A1 1/2015 Palashewski
2015/0025327 A1 1/2015 Young et al.
2015/0026896 A1 1/2015 Fleury et al.
2015/0136146 A1 5/2015 Hood et al.
2015/0137994 A1 5/2015 Rahman et al.
2015/0157137 A1 6/2015 Nunn et al.
2015/0157519 A1 6/2015 Stusynski et al.
2015/0182033 A1 7/2015 Brosnan et al.
2015/0182397 A1 7/2015 Palashewski et al.
2015/0182399 A1 7/2015 Palashewski et al.
2015/0182418 A1 7/2015 Zaiss
2015/0199919 A1 7/2015 Ander et al.
2015/0290059 A1 10/2015 Brosnan et al.
2015/0374137 A1 12/2015 Mahoney et al.
2016/0015184 A1 1/2016 Nunn et al.
2016/0015314 A1 1/2016 Dusanter et al.
2016/0100696 A1 4/2016 Palashewski et al.
2016/0120716 A1* 5/2016 Ribble .................. A61G 7/001 5/616
2016/0242562 A1 8/2016 Karschnik et al.
2016/0300252 A1 10/2016 Frank et al.
2016/0338871 A1 11/2016 Nunn et al.
2016/0367039 A1 12/2016 Young et al.
2017/0003666 A1 1/2017 Nunn et al.
2017/0049243 A1 2/2017 Nunn et al.
2017/0065220 A1 3/2017 Young et al.
2017/0128001 A1 5/2017 Torre et al.
2017/0135632 A1 5/2017 Franceschetti et al.
2017/0143269 A1 5/2017 Young et al.
2017/0191516 A1 7/2017 Griffith et al.
2017/0303697 A1 10/2017 Chen et al.
2017/0318980 A1 11/2017 Mahoney et al.
2017/0354268 A1 12/2017 Brosnan et al.
2018/0116415 A1 5/2018 Karschnik et al.
2018/0116418 A1 5/2018 Shakal et al.
2018/0116419 A1 5/2018 Shakal et al.
2018/0116420 A1 5/2018 Shakal
2018/0119686 A1 5/2018 Shakal et al.
2018/0125259 A1 5/2018 Peterson et al.
2018/0125260 A1 5/2018 Peterson et al.
2019/0053761 A1 2/2019 Torre et al.
2019/0059603 A1 2/2019 Griffith et al.
2019/0069840 A1 3/2019 Young et al.
2019/0082855 A1 3/2019 Brosnan et al.
2019/0099009 A1 4/2019 Connor
2019/0104858 A1 4/2019 Erko et al.
2019/0125095 A1 5/2019 Nunn et al.
2019/0125097 A1 5/2019 Nunn et al.
2019/0200777 A1 7/2019 Demirli et al.
2019/0201265 A1 7/2019 Sayadi et al.
2019/0201266 A1 7/2019 Sayadi et al.
2019/0201267 A1 7/2019 Demirli et al.
2019/0201268 A1 7/2019 Sayadi et al.
2019/0201269 A1 7/2019 Sayadi et al.
2019/0201270 A1 7/2019 Sayadi et al.
2019/0206416 A1 7/2019 Demirli et al.
2019/0209405 A1 7/2019 Sayadi et al.
2019/0328146 A1 10/2019 Palashewski et al.
2019/0328147 A1 10/2019 Palashewski et al.
2020/0107646 A1 4/2020 Sherman et al.
2020/0178887 A1 6/2020 Ramirez et al.
2020/0315367 A1 10/2020 Demirli et al.
2020/0336010 A1 10/2020 Holmvik et al.
2020/0337470 A1 10/2020 Sayadi et al.
2020/0359807 A1 11/2020 Brosnan et al.
2020/0367663 A1 11/2020 Nunn et al.
2020/0383854 A1 12/2020 Gehrke et al.
2020/0405070 A1 12/2020 Palashewski et al.
2020/0405240 A1 12/2020 Palashewski et al.
2020/0405526 A1* 12/2020 Yu ....................... A61B 5/4836
2021/0000261 A1 1/2021 Erko et al.
2021/0034989 A1 2/2021 Palashewski et al.
2021/0045541 A1 2/2021 Nunn et al.
2021/0068552 A1 3/2021 Palashewski et al.
2021/0112992 A1 4/2021 Nunn et al.
2021/0267380 A1 9/2021 Stusynski
2021/0282570 A1 9/2021 Karschnik et al.
2021/0289947 A1 9/2021 Karschnik et al.
2021/0314405 A1 10/2021 Demirli et al.
2021/0346218 A1 11/2021 Stusynski et al.
2022/0000273 A1 1/2022 Palashewski et al.
2022/0000654 A1 1/2022 Nunn et al.
2022/0225786 A1 7/2022 Palashewski et al.
2022/0265059 A1 8/2022 Palashewski et al.
2022/0305231 A1 9/2022 Stusynski et al.
2022/0346565 A1 11/2022 Karschnik et al.
2022/0354431 A1 11/2022 Molina et al.
2022/0386947 A1 12/2022 Molina et al.
2022/0395233 A1 12/2022 Siyahjani et al.
2023/0018558 A1 1/2023 Demirli et al.
2023/0035257 A1 2/2023 Karschnik et al.
2023/0037482 A1 2/2023 Demirli et al.
2023/0054736 A1 2/2023 Holmvik et al.

(56) References Cited

U.S. PATENT DOCUMENTS

| | | | |
|---|---|---|---|
| 2023/0063373 | A1 | 3/2023 | Young et al. |
| 2023/0142604 | A1 | 5/2023 | Dixon et al. |
| 2023/0148762 | A1 | 5/2023 | Karschnik et al. |
| 2023/0181104 | A1 | 6/2023 | Johnston et al. |
| 2023/0190199 | A1 | 6/2023 | Molina |
| 2023/0210256 | A1 | 7/2023 | MacLachlan et al. |
| 2023/0210268 | A1 | 7/2023 | Kirk et al. |
| 2023/0210269 | A1 | 7/2023 | Hill et al. |
| 2023/0210274 | A1 | 7/2023 | Hill et al. |
| 2023/0210275 | A1 | 7/2023 | Hill et al. |
| 2023/0218093 | A1 | 7/2023 | Nunn et al. |

FOREIGN PATENT DOCUMENTS

| | | |
|---|---|---|
| DE | 40 05 822 | 8/1991 |
| GB | 2 471 401 | 12/2010 |
| JP | 2004-049388 | 2/2004 |
| JP | 2004/229875 | 8/2004 |
| JP | 2007-283106 | 11/2007 |
| WO | WO 2004/082549 | 9/2004 |
| WO | WO 2008/128250 | 10/2008 |
| WO | WO 2009/108228 | 9/2009 |
| WO | WO 2009/123641 | 10/2009 |
| WO | WO 2010/149788 | 12/2010 |

OTHER PUBLICATIONS

U.S. Appl. No. 17/745,508, filed May 16, 2022, Nunn et al.
U.S. Appl. No. 18/105,468, filed Feb. 3, 2023, Sayadi et al.
U.S. Appl. No. 18/135,448, filed Apr. 17, 2023, Demirli et al.
U.S. Appl. No. 18/199,255, filed May 18, 2023, Sayadi et al.
U.S. Appl. No. 18/199,750, filed May 19, 2023, Sayadi et al.
U.S. Appl. No. 18/204,141, filed May 31, 2023, Palashewski et al.
U.S. Appl. No. 18/221,056, filed Jul. 12, 2023, Grey et al.
U.S. Appl. No. 18/224,365, filed Jul. 20, 2023, Blomseth et al.
U.S. Appl. No. 18/224,899, filed Jul. 21, 2023, Brosnan et al.
U.S. Appl. No. 18/234,676, filed Aug. 16, 2023, Nunn et al.
U.S. Appl. No. 18/333,861, filed Jun. 13, 2023, Stusynski et al.
U.S. Appl. No. 18/370,552, filed Sep. 20, 2023, Molina et al.
U.S. Appl. No. 29/814,835, filed Nov. 9, 2021, Dixon et al.
U.S. Appl. No. 29/881,955, filed Jan. 9, 2023, Stusynski et al.
U.S. Appl. No. 29/910,800, filed Aug. 24, 2023, Stusynski et al.

* cited by examiner

FIG. 20A
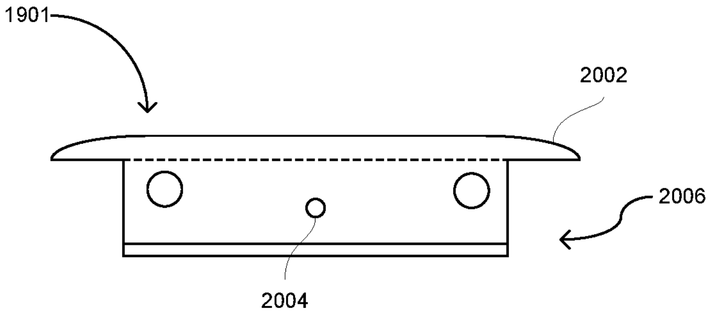
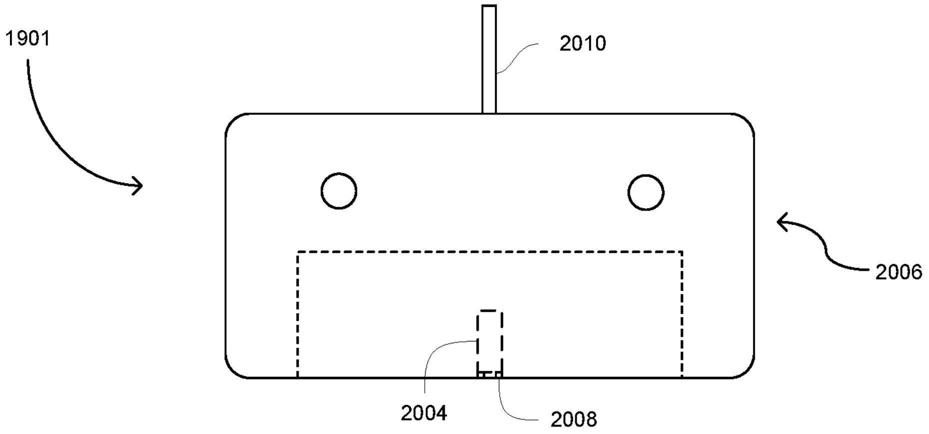
FIG. 20B

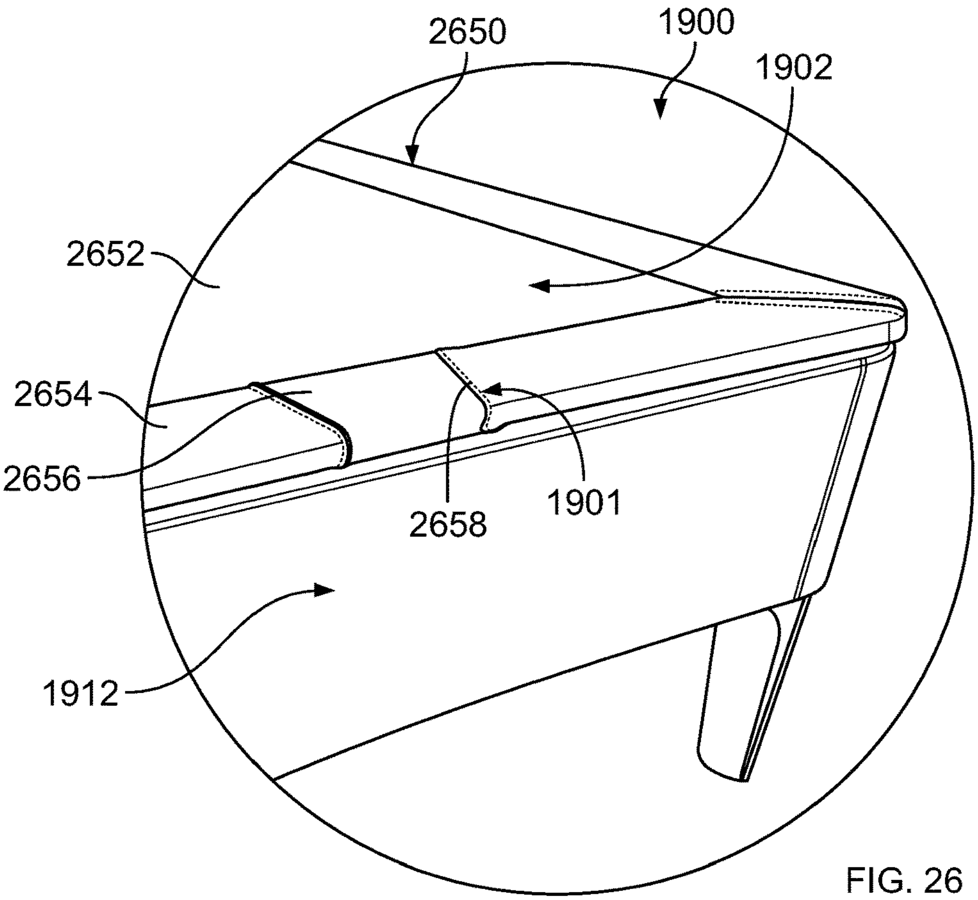
FIG. 26
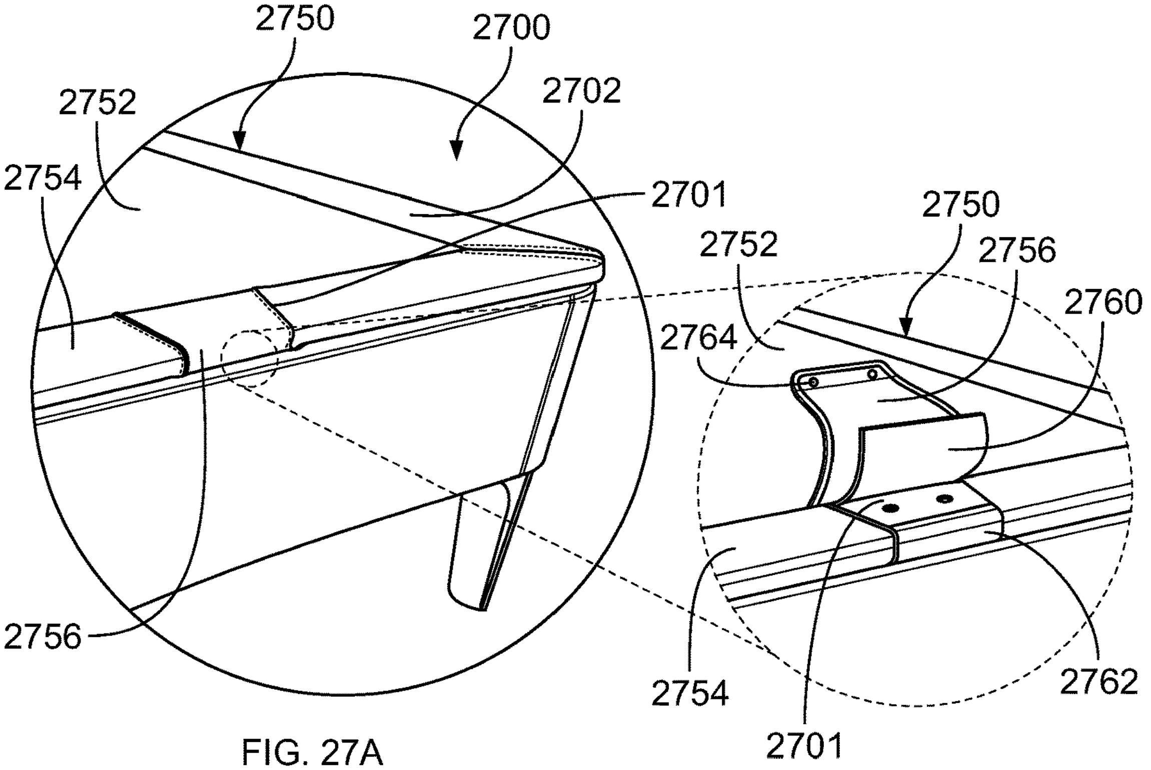
FIG. 27A
FIG. 27B

BED SNORE SENSOR FOR DETECTING SIGNAL INDICATIVE OF A SNORE

CROSS-REFERENCE TO RELATED APPLICATIONS

This application claims is a continuation of U.S. application Ser. No. 16/233,343, filed on Dec. 27, 2018, which claims priority to U.S. Application Ser. No. 62/611,456, filed on Dec. 28, 2017. The disclosure of the prior application is considered part of the disclosure of this application, and is incorporated in its entirety into this application.

BACKGROUND

In general, a bed is a piece of furniture used as a location to sleep or relax. Many modern beds include a soft mattress on a bed frame. The mattress may include springs, foam material, and/or an air chamber to support the weight of one or more occupants.

SUMMARY

A system can include a foundation structure and a sensor. The foundation structure can have a plurality of deck panels configured to support a mattress. The plurality of deck panels can include a head panel. The plurality of deck panels can have a head, a foot, a first side, and a second side, a first edge along the head, a second edge along the foot opposite of the first edge, a third edge along the first side, and a fourth edge along the second side opposite the third edge. The sensor can be configured to detect a sound indicative of a snore. The sensor can be positioned along the third edge or fourth edge of the head panel.

Implementations can include any, all, or none of the following features. A controller can be coupled to the sensor, the controller configured to determine a position of a snoring person based on data received from the sensor. An actuator can be configured to control an elevation angle of the head panel, the actuator being coupled to the controller and the head panel. The actuator can be configured to adjust the head elevation angle between zero and seven degrees from the rest of the foundation in response to detecting a snore using the sensor. The sensor can be positioned along the third edge or fourth edge within two feet of the first edge. The sensor can be positioned along the third edge or fourth edge between six and twelve inches from the first edge. The sensor can be raised when the head panel is raised. The sensor can be positioned along the third edge, the sensor being at least eight inches away from the first edge. The head panel can be a left head panel, wherein the deck panels further includes a right head panel, and wherein the sensor is positioned along the third edge on the left head panel. The sensor can be a MEMs type acoustic sensor. The sensor can be positioned in a water-resistant compartment. The head panel can be a first head panel and the sensor is a first sensor. The system can include a second head panel configured to have an adjustable angle compared to the foundation structure and a second sensor configured to detect a sound indicative of a snore, wherein the second sensor is positioned along an a side edge of the second panel opposite of the first sensor. A fabric deck panel cover can be configured to cover at least a portion of the head panel and the sensor. The fabric deck panel cover can include a detachable and re-attachable flap that is positioned and configured to be opened to allow for access to the sensor. Portions of the fabric deck panel cover can be more permanently attached to the head panel than a portion of the fabric deck panel cover that includes the flap. The sensor can be removable and replaceable.

A method can include detecting a noise with one or more acoustic sensors located on an outer edge of a deck panel of a bed foundation within two feet of a head edge of the deck panel at a head of the bed foundation, determining that the noise is a snore based on a signal from the one or more acoustic sensors, determining a determined side of a bed the snore originated based on the signal from the one or more acoustic sensors, and adjusting the determined side of the bed in response to determining the determined side.

Implementations can include any, all, or none of the following features. Adjusting the determined side of the bed comprises adjusting an angle of a head of the determined side of the bed. The angle can be adjusted from horizontal to substantially seven degrees above horizontal in response to determining the determined side. Adjusting the determined side of the bed comprises adjusting a firmness of a mattress on the determined side of the bed.

A foundation for a bed can include a foundation support structure, a plurality of deck panels, left and right snore sensors, and an actuation system. The plurality of deck panels can include left and right head panels, wherein the deck panels are supported by the foundation support structure with the left head panel positioned on a left side of the foundation at a head of the foundation and with the right head panel positioned on a right side of the foundation at the head of the foundation. The left snore sensor can be positioned on a left edge of the left head panel and configured to detect a sound indicative of a snore. The right snore sensor can be positioned on a right edge of the right head panel and configured to detect a sound indicative of a snore. The actuation system can be in communication with the left and right snore sensors and configured to raise the left head panel in response to determining that a snore is produced by a user on the left side of the foundation based in part by data collected by one or both of the left and right snore sensors and configured to raise the right deck panel in response to determining that a snore is produced by a user on the right side of the foundation based in part by data collected by one or both of the left and right snore sensors.

Implementations can include any, all, or none of the following features. The left and right snore sensors are each positioned within two feet of a head edge of their respective left and right head panels. Each of the left and right head panels comprises a fabric wrapped around the left and right snore sensors. A left rail can be positioned on a left side of the foundation under the left snore sensor, wherein the left snore sensor is raised when the left head panel is raised and the left rail is not raised when the left head panel is raised. A right rail can be positioned on a right side of the foundation under the right snore sensor, wherein the right snore sensor is raised when the right head panel is raised and the right rails is not raised when the right head panel is raised. The left snore sensor can be raised when the left head panel is raised and the right snore sensor is raised when the right head panel is raised. A bed can include the foundation and a mattress positioned on and supported by the deck panels. The mattress can be partially split at a head of the mattress such that a left portion of the head of the mattress can be raised along with the left head panel and a right portion of the head of the mattress can be raised along with the right head panel, wherein the left and right snore sensors are positioned along the left and right edges of the left and right head panels in a location configured to detect snore when the mattress is positioned on the left and right head panels.

Other features, aspects and potential advantages will be apparent from the accompanying description and figures.

DESCRIPTION OF DRAWINGS

FIGS. 20A-20B are schematic diagrams of example snore sensors.

FIG. 26 is a perspective view of a portion of the foundation of FIG. 19 with the snore sensor covered with fabric.

FIGS. 27A-27B are views of another embodiment of a foundation with a snore sensor.

Like reference symbols in the various drawings indicate like elements.

DETAILED DESCRIPTION

Snoring can be an issue for people that sleep in the same room or the same bed. For light sleepers, the snoring of another person can prevent or stop restful sleep. While manual adjustments of bed foundations can reduce snoring for a sleeping occupant, the manual operation of such a system requires a person to be conscious to operate the system. Such a restriction can mean that a person that is awoken by a snore may need to adjust the bed before trying to go back to sleep. This interruption in sleep can reduce the amount of sleep people receive.

This document describes an automatic snore detection and bed adjustments system. The system is capable of detecting a snore, determining what side of the bed a snore originates from, and adjusts the bed in response to the snore. Such automatic intervention reduces the chance of other sleepers from being awoken by the snoring.

Example Airbed Hardware

Figure 1:
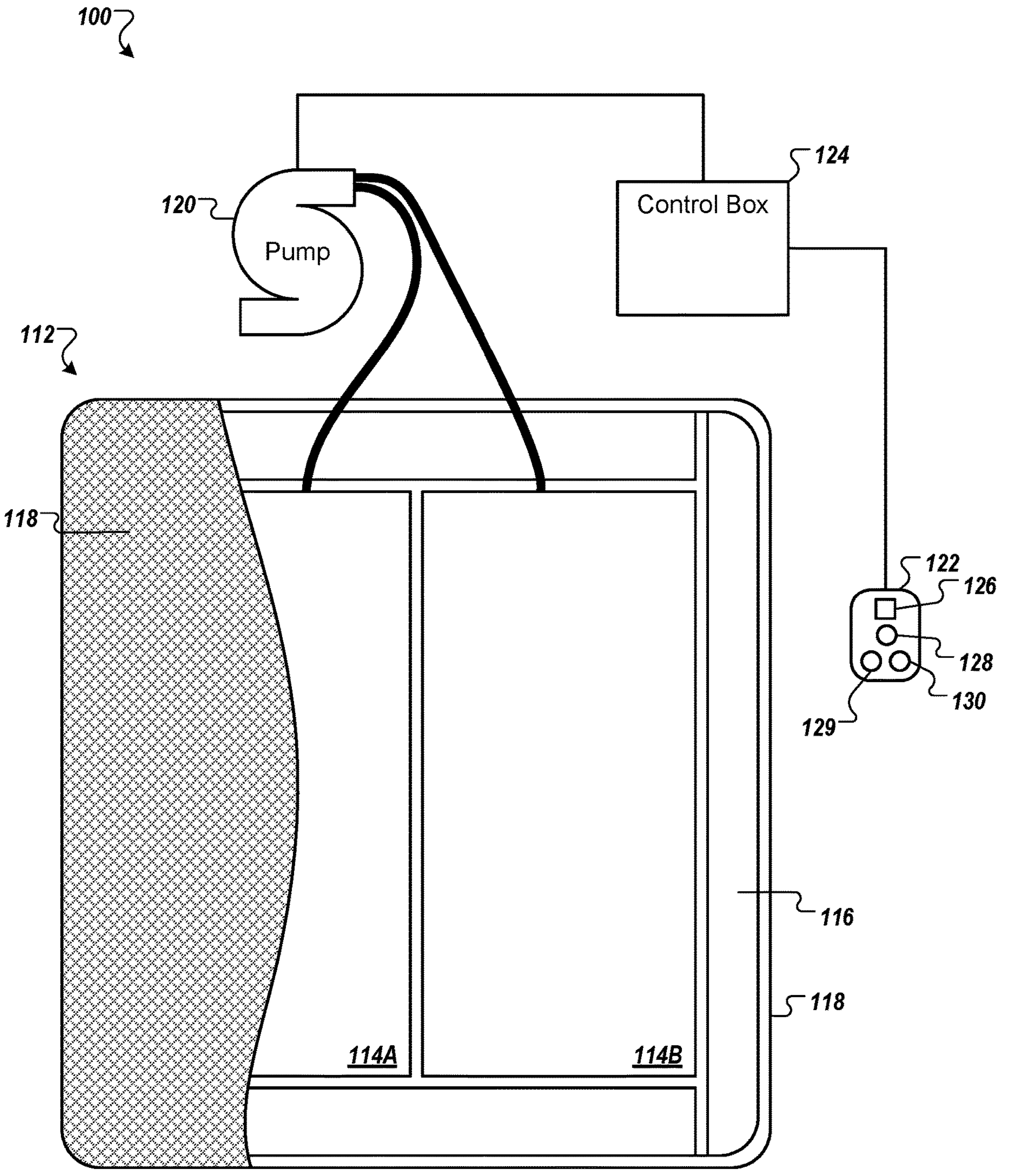
FIG. 1 shows an example air bed system.

FIG. 1 shows an example air bed system 100 that includes a bed 112. The bed 112 includes at least one air chamber 114 surrounded by a resilient border 116 and encapsulated by bed ticking 118. The resilient border 116 can comprise any suitable material, such as foam.

As illustrated in FIG. 1, the bed 112 can be a two chamber design having first and second fluid chambers, such as a first air chamber 114A and a second air chamber 114B. In alternative embodiments, the bed 112 can include chambers for use with fluids other than air that are suitable for the application. In some embodiments, such as single beds or kids' beds, the bed 112 can include a single air chamber 114A or 114B or multiple air chambers 114A and 114B. First and second air chambers 114A and 114B can be in fluid communication with a pump 120. The pump 120 can be in electrical communication with a remote control 122 via control box 124. The control box 124 can include a wired or wireless communications interface for communicating with one or more devices, including the remote control 122. The control box 124 can be configured to operate the pump 120 to cause increases and decreases in the fluid pressure of the first and second air chambers 114A and 114B based upon commands input by a user using the remote control 122. In some implementations, the control box 124 is integrated into a housing of the pump 120.

The remote control 122 can include a display 126, an output selecting mechanism 128, a pressure increase button 129, and a pressure decrease button 130. The output selecting mechanism 128 can allow the user to switch air flow generated by the pump 120 between the first and second air chambers 114A and 114B, thus enabling control of multiple air chambers with a single remote control 122 and a single pump 120. For example, the output selecting mechanism 128 can by a physical control (e.g., switch or button) or an input control displayed on display 126. Alternatively, separate remote control units can be provided for each air chamber and can each include the ability to control multiple air chambers. Pressure increase and decrease buttons 129 and 130 can allow a user to increase or decrease the pressure, respectively, in the air chamber selected with the output selecting mechanism 128. Adjusting the pressure within the selected air chamber can cause a corresponding adjustment to the firmness of the respective air chamber. In some embodiments, the remote control 122 can be omitted or modified as appropriate for an application. For example, in some embodiments the bed 112 can be controlled by a computer, tablet, smart phone, or other device in wired or wireless communication with the bed 112.

Figure 2:
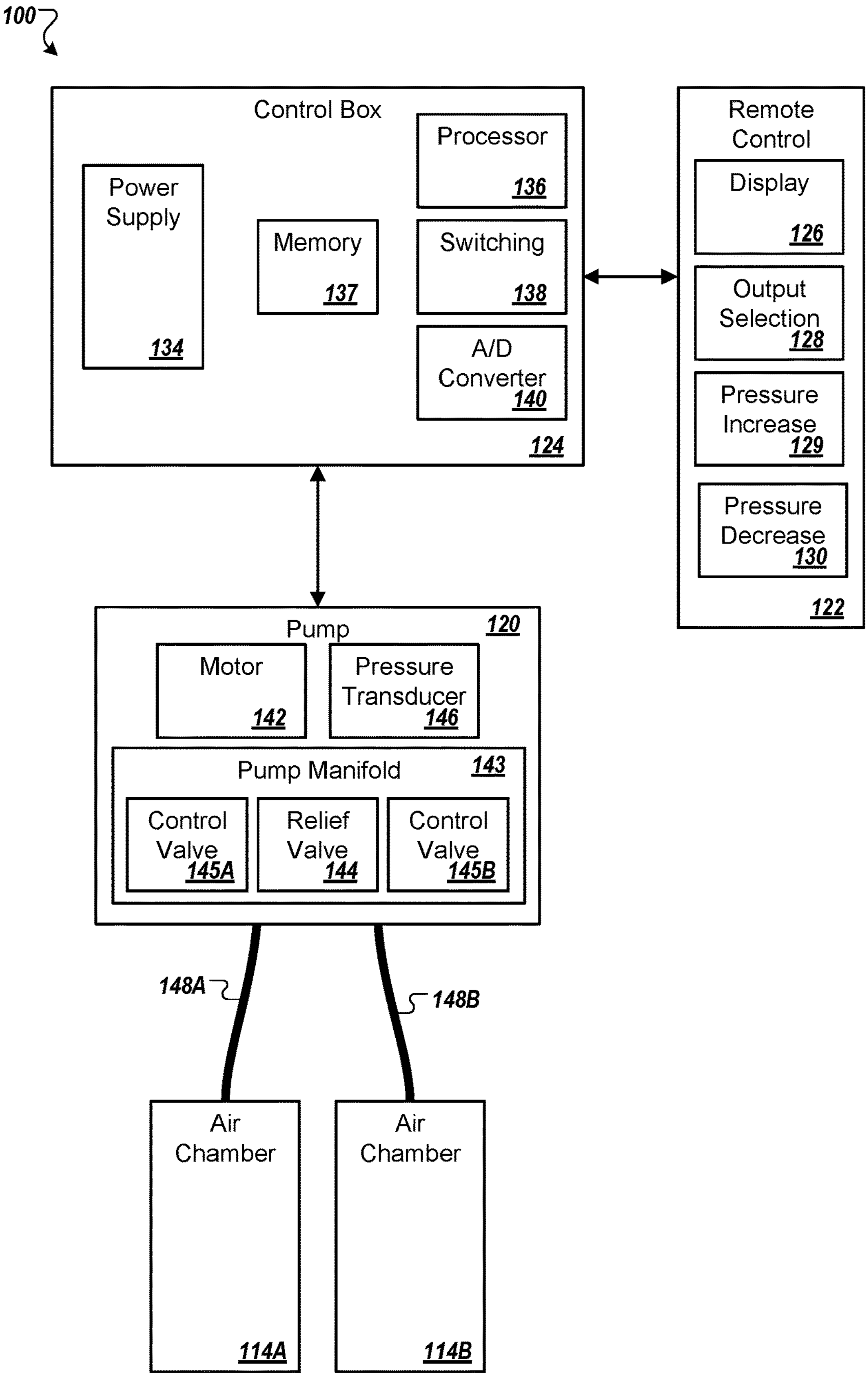
FIG. 2 is a block diagram of an example of various components of an air bed system.

FIG. 2 is a block diagram of an example of various components of an air bed system. For example, these components can be used in the example air bed system 100. As shown in FIG. 2, the control box 124 can include a power supply 134, a processor 136, a memory 137, a switching mechanism 138, and an analog to digital (A/D) converter 140. The switching mechanism 138 can be, for example, a relay or a solid state switch. In some implementations, the switching mechanism 138 can be located in the pump 120 rather than the control box 124.

The pump 120 and the remote control 122 are in two-way communication with the control box 124. The pump 120 includes a motor 142, a pump manifold 143, a relief valve 144, a first control valve 145A, a second control valve 145B, and a pressure transducer 146. The pump 120 is fluidly connected with the first air chamber 114A and the second air chamber 114B via a first tube 148A and a second tube 148B, respectively. The first and second control valves 145A and 145B can be controlled by switching mechanism 138, and are operable to regulate the flow of fluid between the pump 120 and first and second air chambers 114A and 114B, respectively.

In some implementations, the pump 120 and the control box 124 can be provided and packaged as a single unit. In some alternative implementations, the pump 120 and the control box 124 can be provided as physically separate units. In some implementations, the control box 124, the pump 120, or both are integrated within or otherwise contained within a bed frame or bed support structure that supports the bed 112. In some implementations, the control box 124, the pump 120, or both are located outside of a bed frame or bed support structure (as shown in the example in FIG. 1).

The example air bed system 100 depicted in FIG. 2 includes the two air chambers 114A and 114B and the single pump 120. However, other implementations can include an air bed system having two or more air chambers and one or more pumps incorporated into the air bed system to control the air chambers. For example, a separate pump can be associated with each air chamber of the air bed system or a pump can be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber.

In use, the processor 136 can, for example, send a decrease pressure command to one of air chambers 114A or 114B, and the switching mechanism 138 can be used to convert the low voltage command signals sent by the processor 136 to higher operating voltages sufficient to operate the relief valve 144 of the pump 120 and open the control valve 145A or 145B. Opening the relief valve 144 can allow air to escape from the air chamber 114A or 114B through the respective air tube 148A or 148B. During deflation, the pressure transducer 146 can send pressure readings to the processor 136 via the A/D converter 140. The A/D converter 140 can receive analog information from pressure transducer 146 and can convert the analog information to digital information useable by the processor 136. The processor 136 can send the digital signal to the remote control 122 to update the display 126 in order to convey the pressure information to the user.

As another example, the processor 136 can send an increase pressure command. The pump motor 142 can be energized in response to the increase pressure command and send air to the designated one of the air chambers 114A or 114B through the air tube 148A or 148B via electronically operating the corresponding valve 145A or 145B. While air is being delivered to the designated air chamber 114A or 114B in order to increase the firmness of the chamber, the pressure transducer 146 can sense pressure within the pump manifold 143. Again, the pressure transducer 146 can send pressure readings to the processor 136 via the A/D converter 140. The processor 136 can use the information received from the A/D converter 140 to determine the difference between the actual pressure in air chamber 114A or 114B and the desired pressure. The processor 136 can send the digital signal to the remote control 122 to update display 126 in order to convey the pressure information to the user.

Generally speaking, during an inflation or deflation process, the pressure sensed within the pump manifold 143 can provide an approximation of the pressure within the respective air chamber that is in fluid communication with the pump manifold 143. An example method of obtaining a pump manifold pressure reading that is substantially equivalent to the actual pressure within an air chamber includes turning off pump 120, allowing the pressure within the air chamber 114A or 114B and the pump manifold 143 to equalize, and then sensing the pressure within the pump manifold 143 with the pressure transducer 146. Thus, providing a sufficient amount of time to allow the pressures within the pump manifold 143 and chamber 114A or 114B to equalize can result in pressure readings that are accurate approximations of the actual pressure within air chamber 114A or 114B. In some implementations, the pressure of the air chambers 114A and/or 114B can be continuously monitored using multiple pressure sensors (not shown).

In some implementations, information collected by the pressure transducer 146 can be analyzed to determine various states of a person lying on the bed 112. For example, the processor 136 can use information collected by the pressure transducer 146 to determine a heart rate or a respiration rate for a person lying in the bed 112. For example, a user can be lying on a side of the bed 112 that includes the chamber 114A. The pressure transducer 146 can monitor fluctuations in pressure of the chamber 114A and this information can be used to determine the user's heart rate and/or respiration rate. As another example, additional processing can be performed using the collected data to determine a sleep state of the person (e.g., awake, light sleep, deep sleep). For example, the processor 136 can determine when a person falls asleep and, while asleep, the various sleep states of the person.

Additional information associated with a user of the air bed system 100 that can be determined using information collected by the pressure transducer 146 includes motion of the user, presence of the user on a surface of the bed 112, weight of the user, heart arrhythmia of the user, and apnea. Taking user presence detection for example, the pressure transducer 146 can be used to detect the user's presence on the bed 112, e.g., via a gross pressure change determination and/or via one or more of a respiration rate signal, heart rate signal, and/or other biometric signals. For example, a simple pressure detection process can identify an increase in pressure as an indication that the user is present on the bed 112. As another example, the processor 136 can determine that the user is present on the bed 112 if the detected pressure increases above a specified threshold (so as to indicate that a person or other object above a certain weight is positioned on the bed 112). As yet another example, the processor 136 can identify an increase in pressure in combination with detected slight, rhythmic fluctuations in pressure as corresponding to the user being present on the bed 112. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 120. For example, one or more pressure sensors can be located within one or more internal cavities of the pump 120 to detect fluctuations in pressure within the pump 120. The fluctuations in pressure detected at the pump 120 can indicate fluctuations in pressure in one or both of the chambers 114A and 114B. One or more sensors located at the pump 120 can be in fluid communication with the one or both of the chambers 114A and 114B, and the sensors can be operative to determine pressure within the chambers 114A and 114B. The control box 124 can be configured to determine at least one vital sign (e.g., heart rate, respiratory rate) based on the pressure within the chamber 114A or the chamber 114B.

In some implementations, the control box 124 can analyze a pressure signal detected by one or more pressure sensors to determine a heart rate, respiration rate, and/or other vital signs of a user lying or sitting on the chamber 114A or the chamber 114B. More specifically, when a user lies on the bed 112 positioned over the chamber 114A, each of the user's heart beats, breaths, and other movements can create a force on the bed 112 that is transmitted to the chamber 114A. As a result of the force input to the chamber 114A from the user's movement, a wave can propagate through the chamber 114A and into the pump 120. A pressure sensor located at the pump 120 can detect the wave, and thus the pressure signal output by the sensor can indicate a heart rate, respiratory rate, or other information regarding the user.

With regard to sleep state, air bed system 100 can determine a user's sleep state by using various biometric signals such as heart rate, respiration, and/or movement of the user. While the user is sleeping, the processor 136 can receive one or more of the user's biometric signals (e.g., heart rate, respiration, and motion) and determine the user's present sleep state based on the received biometric signals. In some implementations, signals indicating fluctuations in pressure in one or both of the chambers 114A and 114B can be amplified and/or filtered to allow for more precise detection of heart rate and respiratory rate.

The control box 124 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 1 Hz. The control box 124 can also be configured to determine other characteristics of a user based on the received pressure signal, such as blood pressure, tossing and turning movements, rolling movements, limb movements, weight, the presence or lack of presence of a user, and/or the identity of the user. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire contents of which is incorporated herein by reference.

For example, the pressure transducer 146 can be used to monitor the air pressure in the chambers 114A and 114B of the bed 112. If the user on the bed 112 is not moving, the air pressure changes in the air chamber 114A or 114B can be relatively minimal, and can be attributable to respiration and/or heartbeat. When the user on the bed 112 is moving, however, the air pressure in the mattress can fluctuate by a much larger amount. Thus, the pressure signals generated by the pressure transducer 146 and received by the processor 136 can be filtered and indicated as corresponding to motion, heartbeat, or respiration.

In some implementations, rather than performing the data analysis in the control box 124 with the processor 136, a digital signal processor (DSP) can be provided to analyze the data collected by the pressure transducer 146. Alternatively, the data collected by the pressure transducer 146 could be sent to a cloud-based computing system for remote analysis.

In some implementations, the example air bed system 100 further includes a temperature controller configured to increase, decrease, or maintain the temperature of a bed, for example for the comfort of the user. For example, a pad can be placed on top of or be part of the bed 112, or can be placed on top of or be part of one or both of the chambers 114A and 114B. Air can be pushed through the pad and vented to cool off a user of the bed. Conversely, the pad can include a heating element that can be used to keep the user warm. In some implementations, the temperature controller can receive temperature readings from the pad. In some implementations, separate pads are used for the different sides of the bed 112 (e.g., corresponding to the locations of the chambers 114A and 114B) to provide for differing temperature control for the different sides of the bed.

In some implementations, the user of the air bed system 100 can use an input device, such as the remote control 122, to input a desired temperature for the surface of the bed 112 (or for a portion of the surface of the bed 112). The desired temperature can be encapsulated in a command data structure that includes the desired temperature as well as identifies the temperature controller as the desired component to be controlled. The command data structure can then be transmitted via Bluetooth or another suitable communication protocol to the processor 136. In various examples, the command data structure is encrypted before being transmitted. The temperature controller can then configure its elements to increase or decrease the temperature of the pad depending on the temperature input into remote control 122 by the user.

In some implementations, data can be transmitted from a component back to the processor 136 or to one or more display devices, such as the display 126. For example, the current temperature as determined by a sensor element of temperature controller, the pressure of the bed, the current position of the foundation or other information can be transmitted to control box 124. The control box 124 can then transmit the received information to remote control 122 where it can be displayed to the user (e.g., on the display 126).

In some implementations, the example air bed system 100 further includes an adjustable foundation and an articulation controller configured to adjust the position of a bed (e.g., the bed 112) by adjusting the adjustable foundation that supports the bed. For example, the articulation controller can adjust the bed 112 from a flat position to a position in which a head portion of a mattress of the bed is inclined upward (e.g., to facilitate a user sitting up in bed and/or watching television). In some implementations, the bed 112 includes multiple separately articulable sections. For example, portions of the bed corresponding to the locations of the chambers 114A and 114B can be articulated independently from each other, to allow one person positioned on the bed 112 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 112 can include more than one zone that can be independently adjusted. The articulation controller can also be configured to provide different levels of massage to one or more users on the bed 112.

Example of a Bed in a Bedroom Environment

Figure 3:
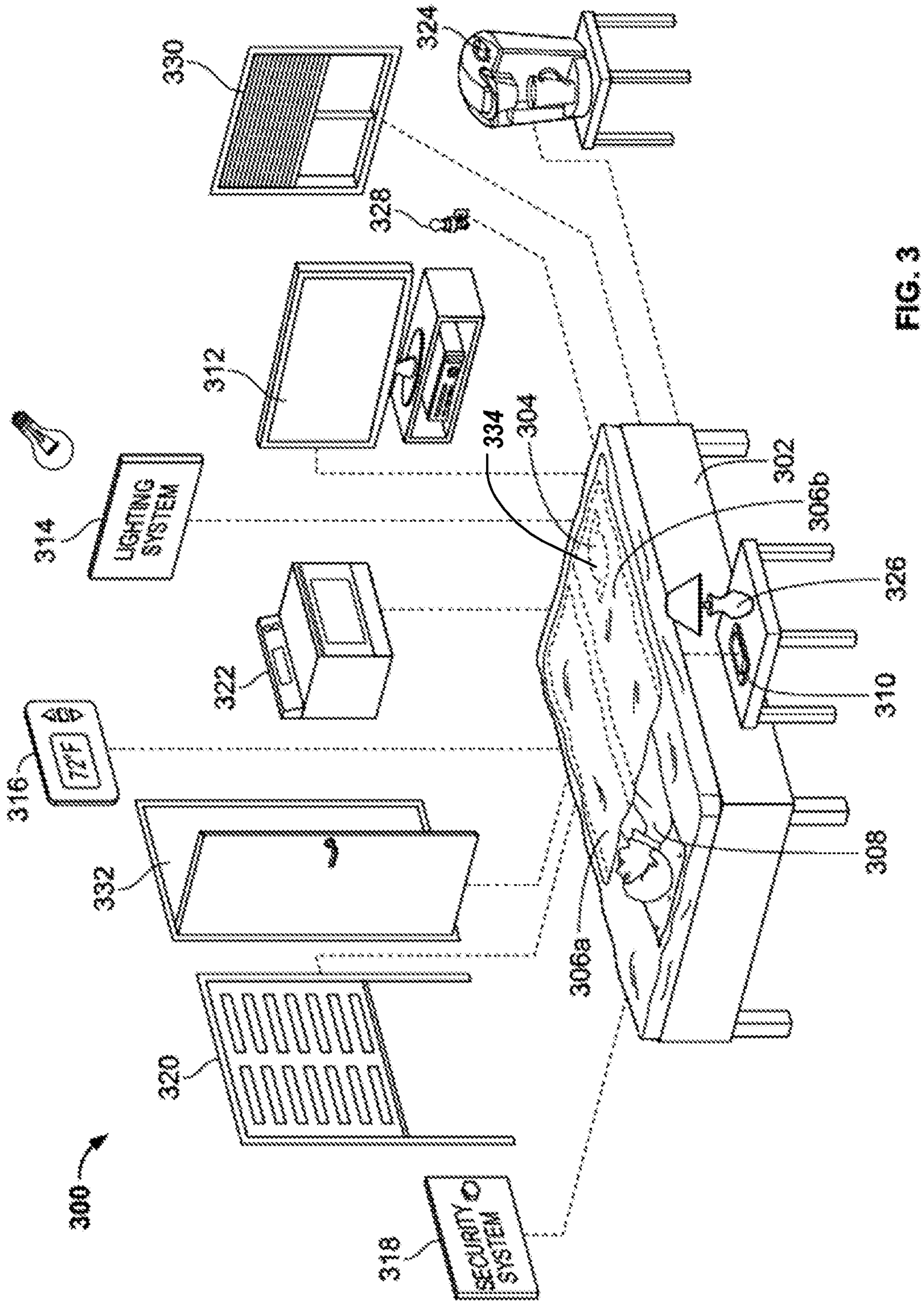
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306*a* and 306*b* (as described above with respect to the air chambers 114A-114B). The pump 304 additionally includes circuitry for controlling inflation and deflation functionality performed by the pump 304. The circuitry is further programmed to detect fluctuations in air pressure of the air chambers 306*a-b* and used the detected fluctuations in air pressure to identify bed presence of a user 308, sleep state of the user 308, movement of the user 308, and biometric signals of the user 308 such as heart rate and respiration rate. In the example shown, the pump 304 is located within a support structure of the bed 302 and the control circuitry 334 for controlling the pump 304 is integrated with the pump 304. In some implementations, the control circuitry 334 is physically separate from the pump 304 and is in wireless or wired communication with the pump 304. In some implementations, the pump 304 and/or control circuitry 334 are located outside of the bed 302. In some implementations, various control functions can be performed by systems located in different physical locations. For example, circuitry for controlling actions of the pump 304 can be located within a pump casing of the pump 304 while control circuitry 334 for performing other functions associated with the bed 302 can be located in another portion of the bed 302, or external to the bed 302. As another example, control circuitry 334 located within the pump 304 can communicate with control circuitry 334 at a remote location through a LAN or WAN (e.g., the internet). As yet another example, the control circuitry 334 can be included in the control box 124 of FIGS. 1 and 2.

In some implementations, one or more devices other than, or in addition to, the pump 304 and control circuitry 334 can be utilized to identify user bed presence, sleep state, movement, and biometric signals. For example, the bed 302 can include a second pump in addition to the pump 304, with each of the two pumps connected to a respective one of the air chambers 306*a-b*. For example, the pump 304 can be in fluid communication with the air chamber 306*b* to control inflation and deflation of the air chamber 306*b* as well as detect user signals for a user located over the air chamber 306*b* such as bed presence, sleep state, movement, and biometric signals while the second pump is in fluid communication with the air chamber 306*a* to control inflation and deflation of the air chamber 306*a* as well as detect user signals for a user located over the air chamber 306*a*.

As another example, the bed 302 can include one or more pressure sensitive pads or surface portions that are operable to detect movement, including user presence, user motion, respiration, and heart rate. For example, a first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located during sleep. The movement detected by the one or more pressure sensitive pads or surface portions can be used by control circuitry 334 to identify user sleep state, bed presence, or biometric signals.

In some implementations, information detected by the bed (e.g., motion information) is processed by control circuitry 334 (e.g., control circuitry 334 integrated with the pump 304) and provided to one or more user devices such as a user device 310 for presentation to the user 308 or to other users. In the example depicted in FIG. 3, the user device 310 is a tablet device; however, in some implementations, the user device 310 can be a personal computer, a smart phone, a smart television (e.g., a television 312), or other user device capable of wired or wireless communication with the control circuitry 334. The user device 310 can be in communication with control circuitry 334 of the bed 302 through a network or through direct point-to-point communication. For example, the control circuitry 334 can be connected to a LAN (e.g., through a Wi-Fi router) and communicate with the user device 310 through the LAN. As another example, the control circuitry 334 and the user device 310 can both connect to the Internet and communicate through the Internet. For example, the control circuitry 334 can connect to the Internet through a WiFi router and the user device 310 can connect to the Internet through communication with a cellular communication system. As another example, the control circuitry 334 can communicate directly with the user device 310 through a wireless communication protocol such as Bluetooth. As yet another example, the control circuitry 334 can communicate with the user device 310 through a wireless communication protocol such as ZigBee, Z-Wave, infrared, or another wireless communication protocol suitable for the application. As another example, the control circuitry 334 can communicate with the user device 310 through a wired connection such as, for example, a USB connector, serial/RS232, or another wired connection suitable for the application.

The user device 310 can display a variety of information and statistics related to sleep, or user 308's interaction with the bed 302. For example, a user interface displayed by the user device 310 can present information including amount of sleep for the user 308 over a period of time (e.g., a single evening, a week, a month, etc.) amount of deep sleep, ratio of deep sleep to restless sleep, time lapse between the user 308 getting into bed and the user 308 falling asleep, total amount of time spent in the bed 302 for a given period of time, heart rate for the user 308 over a period of time, respiration rate for the user 308 over a period of time, or other information related to user interaction with the bed 302 by the user 308 or one or more other users of the bed 302. In some implementations, information for multiple users can be presented on the user device 310, for example information for a first user positioned over the air chamber 306*a* can be presented along with information for a second user positioned over the air chamber 306*b*. In some implementations, the information presented on the user device 310 can vary according to the age of the user 308. For example, the information presented on the user device 310 can evolve with the age of the user 308 such that different information is presented on the user device 310 as the user 308 ages as a child or an adult.

The user device 310 can also be used as an interface for the control circuitry 334 of the bed 302 to allow the user 308 to enter information. The information entered by the user 308 can be used by the control circuitry 334 to provide better information to the user or to various control signals for controlling functions of the bed 302 or other devices. For example, the user can enter information such as weight, height, and age and the control circuitry 334 can use this information to provide the user 308 with a comparison of the user's tracked sleep information to sleep information of other people having similar weights, heights, and/or ages as the user 308. As another example, the user 308 can use the user device 310 as an interface for controlling air pressure of the air chambers 306*a* and 306*b*, for controlling various recline or incline positions of the bed 302, for controlling temperature of one or more surface temperature control devices of the bed 302, or for allowing the control circuitry 334 to generate control signals for other devices (as described in greater detail below).

In some implementations, control circuitry 334 of the bed 302 (e.g., control circuitry 334 integrated into the pump 304) can communicate with other first, second, or third party devices or systems in addition to or instead of the user device 310. For example, the control circuitry 334 can communicate with the television 312, a lighting system 314, a thermostat 316, a security system 318, or other house hold devices such as an oven 322, a coffee maker 324, a lamp 326, and a nightlight 328. Other examples of devices and/or systems that the control circuitry 334 can communicate with include a system for controlling window blinds 330, one or more devices for detecting or controlling the states of one or more doors 332 (such as detecting if a door is open, detecting if a door is locked, or automatically locking a door), and a system for controlling a garage door 320 (e.g., control circuitry 334 integrated with a garage door opener for identifying an open or closed state of the garage door 320 and for causing the garage door opener to open or close the garage door 320). Communications between the control circuitry 334 of the bed 302 and other devices can occur through a network (e.g., a LAN or the Internet) or as point-to-point communication (e.g., using Bluetooth, radio communication, or a wired connection). In some implementations, control circuitry 334 of different beds 302 can communicate with different sets of devices. For example, a kid bed may not communicate with and/or control the same devices as an adult bed. In some embodiments, the bed 302 can evolve with the age of the user such that the control circuitry 334 of the bed 302 communicates with different devices as a function of age of the user.

The control circuitry 334 can receive information and inputs from other devices/systems and use the received information and inputs to control actions of the bed 302 or other devices. For example, the control circuitry 334 can receive information from the thermostat 316 indicating a current environmental temperature for a house or room in which the bed 302 is located. The control circuitry 334 can use the received information (along with other information) to determine if a temperature of all or a portion of the surface of the bed 302 should be raised or lowered. The control circuitry 334 can then cause a heating or cooling mechanism of the bed 302 to raise or lower the temperature of the surface of the bed 302. For example, the user 308 can indicate a desired sleeping temperature of 74 degrees while a second user of the bed 302 indicates a desired sleeping temperature of 72 degrees. The thermostat 316 can indicate to the control circuitry 334 that the current temperature of the bedroom is 72 degrees. The control circuitry 334 can identify that the user 308 has indicated a desired sleeping temperature of 74 degrees, and send control signals to a heating pad located on the user 308's side of the bed to raise the temperature of the portion of the surface of the bed 302 where the user 308 is located to raise the temperature of the user 308's sleeping surface to the desired temperature.

The control circuitry 334 can also generate control signals controlling other devices and propagate the control signals to the other devices. In some implementations, the control signals are generated based on information collected by the control circuitry 334, including information related to user interaction with the bed 302 by the user 308 and/or one or more other users. In some implementations, information collected from one or more other devices other than the bed 302 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry 334 of the bed 302. For example, information on the time of day can be combined with information relating to movement and bed presence of the user 308 to generate control signals for the lighting system 314. In some implementations, rather than or in addition to providing control signals for one or more other devices, the control circuitry 334 can provide collected information (e.g., information related to user movement, bed presence, sleep state, or biometric signals for the user 308) to one or more other devices to allow the one or more other devices to utilize the collected information when generating control signals. For example, control circuitry 334 of the bed 302 can provide information relating to user interactions with the bed 302 by the user 308 to a central controller (not shown) that can use the provided information to generate control signals for various devices, including the bed 302.

Still referring to FIG. 3, the control circuitry 334 of the bed 302 can generate control signals for controlling actions of other devices, and transmit the control signals to the other devices in response to information collected by the control circuitry 334, including bed presence of the user 308, sleep state of the user 308, and other factors. For example, control circuitry 334 integrated with the pump 304 can detect a feature of a mattress of the bed 302, such as an increase in pressure in the air chamber 306*b*, and use this detected increase in air pressure to determine that the user 308 is present on the bed 302. In some implementations, the control circuitry 334 can identify a heart rate or respiratory rate for the user 308 to identify that the increase in pressure is due to a person sitting, laying, or otherwise resting on the bed 302 rather than an inanimate object (such as a suitcase) having been placed on the bed 302. In some implementations, the information indicating user bed presence is combined with other information to identify a current or future likely state for the user 308. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry 334 detects that the user 308 has left the bed 302 at 6:30 am (e.g., indicating that the user 308 has woken up for the day), and then later detects user bed presence of the user 308 at 7:30 am, the control circuitry 334 can use this information that the newly detected user bed presence is likely temporary (e.g., while the user 308 ties her shoes before heading to work) rather than an indication that the user 308 is intending to stay on the bed 302 for an extended period.

In some implementations, the control circuitry 334 is able to use collected information (including information related to user interaction with the bed 302 by the user 308, as well as environmental information, time information, and input received from the user) to identify use patterns for the user 308. For example, the control circuitry 334 can use information indicating bed presence and sleep states for the user 308 collected over a period of time to identify a sleep pattern for the user. For example, the control circuitry 334 can identify that the user 308 generally goes to bed between 9:30 pm and 10:00 pm, generally falls asleep between 10:00 pm and 11:00 pm, and generally wakes up between 6:30 am and 6:45 am based on information indicating user presence and biometrics for the user 308 collected over a week. The control circuitry 334 can use identified patterns for a user to better process and identify user interactions with the bed 302 by the user 308.

For example, given the above example user bed presence, sleep, and wake patterns for the user 308, if the user 308 is detected as being on the bed at 3:00 pm, the control circuitry 334 can determine that the user's presence on the bed is only temporary, and use this determination to generate different control signals than would be generated if the control circuitry 334 determined that the user 308 was in bed for the evening. As another example, if the control circuitry 334 detects that the user 308 has gotten out of bed at 3:00 am, the control circuitry 334 can use identified patterns for the user 308 to determine that the user has only gotten up temporarily (for example, to use the rest room, or get a glass of water) and is not up for the day. By contrast, if the control circuitry 334 identifies that the user 308 has gotten out of the bed 302 at 6:40 am, the control circuitry 334 can determine that the user is up for the day and generate a different set of control signals than those that would be generated if it were determined that the user 308 were only getting out of bed temporarily (as would be the case when the user 308 gets out of the bed 302 at 3:00 am). For other users 308, getting out of the bed 302 at 3:00 am can be the normal wake-up time, which the control circuitry 334 can learn and respond to accordingly.

As described above, the control circuitry 334 for the bed 302 can generate control signals for control functions of various other devices. The control signals can be generated, at least in part, based on detected interactions by the user 308 with the bed 302, as well as other information including time, date, temperature, etc. For example, the control circuitry 334 can communicate with the television 312, receive information from the television 312, and generate control signals for controlling functions of the television 312. For example, the control circuitry 334 can receive an indication from the television 312 that the television 312 is currently on. If the television 312 is located in a different room from the bed 302, the control circuitry 334 can generate a control signal to turn the television 312 off upon making a determination that the user 308 has gone to bed for the evening. For example, if bed presence of the user 308 on the bed 302 is detected during a particular time range (e.g., between 8:00 pm and 7:00 am) and persists for longer than a threshold period of time (e.g., 10 minutes) the control circuitry 334 can use this information to determine that the user 308 is in bed for the evening. If the television 312 is on (as indicated by communications received by the control circuitry 334 of the bed 302 from the television 312) the control circuitry 334 can generate a control signal to turn the television 312 off. The control signals can then be transmitted to the television (e.g., through a directed communication link between the television 312 and the control circuitry 334 or through a network). As another example, rather than turning off the television 312 in response to detection of user bed presence, the control circuitry 334 can generate a control signal that causes the volume of the television 312 to be lowered by a pre-specified amount.

As another example, upon detecting that the user 308 has left the bed 302 during a specified time range (e.g., between 6:00 am and 8:00 am) the control circuitry 334 can generate control signals to cause the television 312 to turn on and tune to a pre-specified channel (e.g., the user 308 has indicated a preference for watching the morning news upon getting out of bed in the morning). The control circuitry 334 can generate the control signal and transmit the signal to the television 312 to cause the television 312 to turn on and tune to the desired station (which could be stored at the control circuitry 334, the television 312, or another location). As another example, upon detecting that the user 308 has gotten up for the day, the control circuitry 334 can generate and transmit control signals to cause the television 312 to turn on and begin playing a previously recorded program from a digital video recorder (DVR) in communication with the television 312.

As another example, if the television 312 is in the same room as the bed 302, the control circuitry 334 does not cause the television 312 to turn off in response to detection of user bed presence. Rather, the control circuitry 334 can generate and transmit control signals to cause the television 312 to turn off in response to determining that the user 308 is asleep. For example, the control circuitry 334 can monitor biometric signals of the user 308 (e.g., motion, heart rate, respiration rate) to determine that the user 308 has fallen asleep. Upon detecting that the user 308 is sleeping, the control circuitry 334 generates and transmits a control signal to turn the television 312 off. As another example, the control circuitry 334 can generate the control signal to turn off the television 312 after a threshold period of time after the user 308 has fallen asleep (e.g., 10 minutes after the user has fallen asleep). As another example, the control circuitry 334 generates control signals to lower the volume of the television 312 after determining that the user 308 is asleep. As yet another example, the control circuitry 334 generates and transmits a control signal to cause the television to gradually lower in volume over a period of time and then turn off in response to determining that the user 308 is asleep.

In some implementations, the control circuitry 334 can similarly interact with other media devices, such as computers, tablets, smart phones, stereo systems, etc. For example, upon detecting that the user 308 is asleep, the control circuitry 334 can generate and transmit a control signal to the user device 310 to cause the user device 310 to turn off, or turn down the volume on a video or audio file being played by the user device 310.

The control circuitry 334 can additionally communicate with the lighting system 314, receive information from the lighting system 314, and generate control signals for controlling functions of the lighting system 314. For example, upon detecting user bed presence on the bed 302 during a certain time frame (e.g., between 8:00 pm and 7:00 am) that lasts for longer than a threshold period of time (e.g., 10 minutes) the control circuitry 334 of the bed 302 can determine that the user 308 is in bed for the evening. In response to this determination, the control circuitry 334 can generate control signals to cause lights in one or more rooms other than the room in which the bed 302 is located to switch off. The control signals can then be transmitted to the lighting system 314 and executed by the lighting system 314 to cause the lights in the indicated rooms to shut off. For example, the control circuitry 334 can generate and transmit control signals to turn off lights in all common rooms, but not in other bedrooms. As another example, the control signals generated by the control circuitry 334 can indicate that lights in all rooms other than the room in which the bed 302 is located are to be turned off, while one or more lights located outside of the house containing the bed 302 are to be turned on, in response to determining that the user 308 is in bed for the evening. Additionally, the control circuitry 334 can generate and transmit control signals to cause the nightlight 328 to turn on in response to determining user 308 bed presence or whether the user 308 is asleep. As another example, the control circuitry 334 can generate first control signals for turning off a first set of lights (e.g., lights in common rooms) in response to detecting user bed presence, and second control signals for turning off a second set of lights (e.g., lights in the room in which the bed 302 is located) in response to detecting that the user 308 is asleep.

In some implementations, in response to determining that the user 308 is in bed for the evening, the control circuitry 334 of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep when the control circuitry 334 has determined that the user 308 is in bed for the evening.

The control circuitry 334 can also be configured to implement a sunrise lighting scheme when the user 308 wakes up in the morning. The control circuitry 334 can determine that the user 308 is awake for the day, for example, by detecting that the user 308 has gotten off of the bed 302 (i.e., is no longer present on the bed 302) during a specified time frame (e.g., between 6:00 am and 8:00 am). As another example, the control circuitry 334 can monitor movement, heart rate, respiratory rate, or other biometric signals of the user 308 to determine that the user 308 is awake even though the user 308 has not gotten out of bed. If the control circuitry 334 detects that the user is awake during a specified time frame, the control circuitry 334 can determine that the user 308 is awake for the day. The specified time frame can be, for example, based on previously recorded user bed presence information collected over a period of time (e.g., two weeks) that indicates that the user 308 usually wakes up for the day between 6:30 am and 7:30 am. In response to the control circuitry 334 determining that the user 308 is awake, the control circuitry 334 can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. For example, the sunrise lighting scheme can include lighting the bedroom with blue light to gently assist the user 308 in waking up and becoming active.

In some implementations, the control circuitry 334 can generate different control signals for controlling actions of one or more components, such as the lighting system 314, depending on a time of day that user interactions with the bed 302 are detected. For example, the control circuitry 334 can use historical user interaction information for interactions between the user 308 and the bed 302 to determine that the user 308 usually falls asleep between 10:00 pm and 11:00 pm and usually wakes up between 6:30 am and 7:30 am on weekdays. The control circuitry 334 can use this information to generate a first set of control signals for controlling the lighting system 314 if the user 308 is detected as getting out of bed at 3:00 am and to generate a second set of control signals for controlling the lighting system 314 if the user 308 is detected as getting out of bed after 6:30 am. For example, if the user 308 gets out of bed prior to 6:30 am, the control circuitry 334 can turn on lights that guide the user 308's route to a restroom. As another example, if the user 308 gets out of bed prior to 6:30 am, the control circuitry 334 can turn on lights that guide the user 308's route to the kitchen (which can include, for example, turning on the nightlight 328, turning on under bed lighting, or turning on the lamp 326).

As another example, if the user 308 gets out of bed after 6:30 am, the control circuitry 334 can generate control signals to cause the lighting system 314 to initiate a sunrise lighting scheme, or to turn on one or more lights in the bedroom and/or other rooms. In some implementations, if the user 308 is detected as getting out of bed prior to a specified morning rise time for the user 308, the control circuitry 334 causes the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (i.e., prior to normal rise time for the user 308) can prevent other occupants of the house from being woken by the lights while still allowing the user 308 to see in order to reach the restroom, kitchen, or another destination within the house.

The historical user interaction information for interactions between the user 308 and the bed 302 can be used to identify user sleep and awake time frames. For example, user bed presence times and sleep times can be determined for a set period of time (e.g., two weeks, a month, etc.). The control circuitry 334 can then identify a typical time range or time frame in which the user 308 goes to bed, a typical time frame for when the user 308 falls asleep, and a typical time frame for when the user 308 wakes up (and in some cases, different time frames for when the user 308 wakes up and when the user 308 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 308 going to bed for the evening. As another example, detection of bed presence of the user 308 starting from a half hour before the earliest typical time that the user 308 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry 334 can distinguish between the user 308 going to bed for an extended period (such as for the night) as opposed to being present on the bed 302 for a shorter period (such as for a nap) by sensing duration of presence of the user 308. In some examples, the control circuitry 334 can distinguish between the user 308 going to bed for an extended period (such as for the night) as opposed to going to bed for a shorter period (such as for a nap) by sensing duration of sleep of the user 308. For example, the control circuitry 334 can set a time threshold whereby if the user 308 is sensed on the bed 302 for longer than the threshold, the user 308 is considered to have gone to bed for the night. In some examples, the threshold can be about 2 hours, whereby if the user 308 is sensed on the bed 302 for greater than 2 hours, the control circuitry 334 registers that as an extended sleep event. In other examples, the threshold can be greater than or less than two hours.

The control circuitry 334 can detect repeated extended sleep events to determine a typical bed time range of the user 308 automatically, without requiring the user 308 to enter a bed time range. This can allow the control circuitry 334 to accurately estimate when the user 308 is likely to go to bed for an extended sleep event, regardless of whether the user 308 typically goes to bed using a traditional sleep schedule or a non-traditional sleep schedule. The control circuitry 334 can then use knowledge of the bed time range of the user 308 to control one or more components (including components of the bed 302 and/or non-bed peripherals) differently based on sensing bed presence during the bed time range or outside of the bed time range.

In some examples, the control circuitry 334 can automatically determine the bed time range of the user 308 without requiring user inputs. In some examples, the control circuitry 334 can determine the bed time range of the user 308 automatically and in combination with user inputs. In some examples, the control circuitry 334 can set the bed time range directly according to user inputs. In some examples, the control circuity 334 can associate different bed times with different days of the week. In each of these examples, the control circuitry 334 can control one or more components (such as the lighting system 314, the thermostat 316, the security system 318, the oven 322, the coffee maker 324, the lamp 326, and the nightlight 328), as a function of sensed bed presence and the bed time range.

The control circuitry 334 can additionally communicate with the thermostat 316, receive information from the thermostat 316, and generate control signals for controlling functions of the thermostat 316. For example, the user 308 can indicate user preferences for different temperatures at different times, depending on the sleep state or bed presence of the user 308. For example, the user 308 may prefer an environmental temperature of 72 degrees when out of bed, 70 degrees when in bed but awake, and 68 degrees when sleeping. The control circuitry 334 of the bed 302 can detect bed presence of the user 308 in the evening and determine that the user 308 is in bed for the night. In response to this determination, the control circuitry 334 can generate control signals to cause the thermostat to change the temperature to 70 degrees. The control circuitry 334 can then transmit the control signals to the thermostat 316. Upon detecting that the user 308 is in bed during the bed time range or asleep, the control circuitry 334 can generate and transmit control signals to cause the thermostat 316 to change the temperature to 68. The next morning, upon determining that the user is awake for the day (e.g., the user 308 gets out of bed after 6:30 am) the control circuitry 334 can generate and transmit control circuitry 334 to cause the thermostat to change the temperature to 72 degrees.

In some implementations, the control circuitry 334 can similarly generate control signals to cause one or more heating or cooling elements on the surface of the bed 302 to change temperature at various times, either in response to user interaction with the bed 302 or at various pre-programmed times. For example, the control circuitry 334 can activate a heating element to raise the temperature of one side of the surface of the bed 302 to 73 degrees when it is detected that the user 308 has fallen asleep. As another example, upon determining that the user 308 is up for the day, the control circuitry 334 can turn off a heating or cooling element. As yet another example, the user 308 can pre-program various times at which the temperature at the surface of the bed should be raised or lowered. For example, the user can program the bed 302 to raise the surface temperature to 76 degrees at 10:00 pm, and lower the surface temperature to 68 degrees at 11:30 pm.

In some implementations, in response to detecting user bed presence of the user 308 and/or that the user 308 is asleep, the control circuitry 334 can cause the thermostat 316 to change the temperature in different rooms to different values. For example, in response to determining that the user 308 is in bed for the evening, the control circuitry 334 can generate and transmit control signals to cause the thermostat 316 to set the temperature in one or more bedrooms of the house to 72 degrees and set the temperature in other rooms to 67 degrees.

The control circuitry 334 can also receive temperature information from the thermostat 316 and use this temperature information to control functions of the bed 302 or other devices. For example, as discussed above, the control circuitry 334 can adjust temperatures of heating elements included in the bed 302 in response to temperature information received from the thermostat 316.

In some implementations, the control circuitry 334 can generate and transmit control signals for controlling other temperature control systems. For example, in response to determining that the user 308 is awake for the day, the control circuitry 334 can generate and transmit control signals for causing floor heating elements to activate. For example, the control circuitry 334 can cause a floor heating system for a master bedroom to turn on in response to determining that the user 308 is awake for the day.

The control circuitry 334 can additionally communicate with the security system 318, receive information from the security system 318, and generate control signals for controlling functions of the security system 318. For example, in response to detecting that the user 308 in is bed for the evening, the control circuitry 334 can generate control signals to cause the security system to engage or disengage security functions. The control circuitry 334 can then transmit the control signals to the security system 318 to cause the security system 318 to engage. As another example, the control circuitry 334 can generate and transmit control signals to cause the security system 318 to disable in response to determining that the user 308 is awake for the day (e.g., user 308 is no longer present on the bed 302 after 6:00 am). In some implementations, the control circuitry 334 can generate and transmit a first set of control signals to cause the security system 318 to engage a first set of security features in response to detecting user bed presence of the user 308, and can generate and transmit a second set of control signals to cause the security system 318 to engage a second set of security features in response to detecting that the user 308 has fallen asleep.

In some implementations, the control circuitry 334 can receive alerts from the security system 318 (and/or a cloud service associated with the security system 318) and indicate the alert to the user 308. For example, the control circuitry 334 can detect that the user 308 is in bed for the evening and in response, generate and transmit control signals to cause the security system 318 to engage or disengage. The security system can then detect a security breach (e.g., someone has opened the door 332 without entering the security code, or someone has opened a window when the security system 318 is engaged). The security system 318 can communicate the security breach to the control circuitry 334 of the bed 302. In response to receiving the communication from the security system 318, the control circuitry 334 can generate control signals to alert the user 308 to the security breach. For example, the control circuitry 334 can cause the bed 302 to vibrate. As another example, the control circuitry 334 can cause portions of the bed 302 to articulate (e.g., cause the head section to raise or lower) in order to wake the user 308 and alert the user to the security breach. As another example, the control circuitry 334 can generate and transmit control signals to cause the lamp 326 to flash on and off at regular intervals to alert the user 308 to the security breach. As another example, the control circuitry 334 can alert the user 308 of one bed 302 regarding a security breach in a bedroom of another bed, such as an open window in a kid's bedroom. As another example, the control circuitry 334 can send an alert to a garage door controller (e.g., to close and lock the door). As another example, the control circuitry 334 can send an alert for the security to be disengaged.

The control circuitry 334 can additionally generate and transmit control signals for controlling the garage door 320 and receive information indicating a state of the garage door 320 (i.e., open or closed). For example, in response to determining that the user 308 is in bed for the evening, the control circuitry 334 can generate and transmit a request to a garage door opener or another device capable of sensing if the garage door 320 is open. The control circuitry 334 can request information on the current state of the garage door 320. If the control circuitry 334 receives a response (e.g., from the garage door opener) indicating that the garage door 320 is open, the control circuitry 334 can either notify the user 308 that the garage door is open, or generate a control signal to cause the garage door opener to close the garage door 320. For example, the control circuitry 334 can send a message to the user device 310 indicating that the garage door is open. As another example, the control circuitry 334 can cause the bed 302 to vibrate. As yet another example, the control circuitry 334 can generate and transmit a control signal to cause the lighting system 314 to cause one or more lights in the bedroom to flash to alert the user 308 to check the user device 310 for an alert (in this example, an alert regarding the garage door 320 being open). Alternatively, or additionally, the control circuitry 334 can generate and transmit control signals to cause the garage door opener to close the garage door 320 in response to identifying that the user 308 is in bed for the evening and that the garage door 320 is open. In some implementations, control signals can vary depend on the age of the user 308.

The control circuitry 334 can similarly send and receive communications for controlling or receiving state information associated with the door 332 or the oven 322. For example, upon detecting that the user 308 is in bed for the evening, the control circuitry 334 can generate and transmit a request to a device or system for detecting a state of the door 332. Information returned in response to the request can indicate various states for the door 332 such as open, closed but unlocked, or closed and locked. If the door 332 is open or closed but unlocked, the control circuitry 334 can alert the user 308 to the state of the door, such as in a manner described above with reference to the garage door 320. Alternatively, or in addition to alerting the user 308, the control circuitry 334 can generate and transmit control signals to cause the door 332 to lock, or to close and lock. If the door 332 is closed and locked, the control circuitry 334 can determine that no further action is needed.

Similarly, upon detecting that the user 308 is in bed for the evening, the control circuitry 334 can generate and transmit a request to the oven 322 to request a state of the oven 322 (e.g., on or off). If the oven 322 is on, the control circuitry 334 can alert the user 308 and/or generate and transmit control signals to cause the oven 322 to turn off. If the oven is already off, the control circuitry 334 can determine that no further action is necessary. In some implementations, different alerts can be generated for different events. For example, the control circuitry 334 can cause the lamp 326 (or one or more other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user of that bed has gotten up (e.g., that a child of the user 308 has gotten out of bed in the middle of the night as sensed by a sensor in the bed 302 of the child). Other examples of alerts that can be processed by the control circuitry 334 of the bed 302 and communicated to the user include a smoke detector detecting smoke (and communicating this detection of smoke to the control circuitry 334), a carbon monoxide tester detecting carbon monoxide, a heater malfunctioning, or an alert from any other device capable of communicating with the control circuitry 334 and detecting an occurrence that should be brought to the user 308's attention.

The control circuitry 334 can also communicate with a system or device for controlling a state of the window blinds 330. For example, in response to determining that the user 308 is in bed for the evening, the control circuitry 334 can generate and transmit control signals to cause the window blinds 330 to close. As another example, in response to determining that the user 308 is up for the day (e.g., user has gotten out of bed after 6:30 am) the control circuitry 334 can generate and transmit control signals to cause the window blinds 330 to open. By contrast, if the user 308 gets out of bed prior to a normal rise time for the user 308, the control circuitry 334 can determine that the user 308 is not awake for the day and does not generate control signals for causing the window blinds 330 to open. As yet another example, the control circuitry 334 can generate and transmit control signals that cause a first set of blinds to close in response to detecting user bed presence of the user 308 and a second set of blinds to close in response to detecting that the user 308 is asleep.

The control circuitry 334 can generate and transmit control signals for controlling functions of other household devices in response to detecting user interactions with the bed 302. For example, in response to determining that the user 308 is awake for the day, the control circuitry 334 can generate and transmit control signals to the coffee maker 324 to cause the coffee maker 324 to begin brewing coffee. As another example, the control circuitry 334 can generate and transmit control signals to the oven 322 to cause the oven to begin preheating (for users that like fresh baked bread in the morning). As another example, the control circuitry 334 can use information indicating that the user 308 is awake for the day along with information indicating that the time of year is currently winter and/or that the outside temperature is below a threshold value to generate and transmit control signals to cause a car engine block heater to turn on.

As another example, the control circuitry 334 can generate and transmit control signals to cause one or more devices to enter a sleep mode in response to detecting user bed presence of the user 308, or in response to detecting that the user 308 is asleep. For example, the control circuitry 334 can generate control signals to cause a mobile phone of the user 308 to switch into sleep mode. The control circuitry 334 can then transmit the control signals to the mobile phone. Later, upon determining that the user 308 is up for the day, the control circuitry 334 can generate and transmit control signals to cause the mobile phone to switch out of sleep mode.

In some implementations, the control circuitry 334 can communicate with one or more noise control devices. For example, upon determining that the user 308 is in bed for the evening, or that the user 308 is asleep, the control circuitry 334 can generate and transmit control signals to cause one or more noise cancelation devices to activate. The noise cancelation devices can, for example, be included as part of the bed 302 or located in the bedroom with the bed 302. As another example, upon determining that the user 308 is in bed for the evening or that the user 308 is asleep, the control circuitry 334 can generate and transmit control signals to turn the volume on, off, up, or down, for one or more sound generating devices, such as a stereo system radio, computer, tablet, etc.

Additionally, functions of the bed 302 are controlled by the control circuitry 334 in response to user interactions with the bed 302. For example, the bed 302 can include an adjustable foundation and an articulation controller configured to adjust the position of one or more portions of the bed 302 by adjusting the adjustable foundation that supports the bed. For example, the articulation controller can adjust the bed 302 from a flat position to a position in which a head portion of a mattress of the bed 302 is inclined upward (e.g., to facilitate a user sitting up in bed and/or watching television). In some implementations, the bed 302 includes multiple separately articulable sections. For example, portions of the bed corresponding to the locations of the air chambers **306*a* and 306*b* can be articulated independently from each other, to allow one person positioned on the bed 302 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 302 can include more than one zone that can be independently adjusted. The articulation controller can also be configured to provide different levels of massage to one or more users on the bed 302 or to cause the bed to vibrate to communicate alerts to the user 308** as described above.

The control circuitry 334 can adjust positions (e.g., incline and decline positions for the user 308 and/or an additional user of the bed 302) in response to user interactions with the bed 302. For example, the control circuitry 334 can cause the articulation controller to adjust the bed 302 to a first recline position for the user 308 in response to sensing user bed presence for the user 308. The control circuitry 334 can cause the articulation controller to adjust the bed 302 to a second recline position (e.g., a less reclined, or flat position) in response to determining that the user 308 is asleep. As another example, the control circuitry 334 can receive a communication from the television 312 indicating that the user 308 has turned off the television 312, and in response the control circuitry 334 can cause the articulation controller to adjust the position of the bed 302 to a preferred user sleeping position (e.g., due to the user turning off the television 312 while the user 308 is in bed indicating that the user 308 wishes to go to sleep).

In some implementations, the control circuitry 334 can control the articulation controller so as to wake up one user of the bed 302 without waking another user of the bed 302. For example, the user 308 and a second user of the bed 302 can each set distinct wakeup times (e.g., 6:30 am and 7:15 am respectively). When the wakeup time for the user 308 is reached, the control circuitry 334 can cause the articulation controller to vibrate or change the position of only a side of the bed on which the user 308 is located to wake the user 308 without disturbing the second user. When the wakeup time for the second user is reached, the control circuitry 334 can cause the articulation controller to vibrate or change the position of only the side of the bed on which the second user is located. Alternatively, when the second wakeup time occurs, the control circuitry 334 can utilize other methods (such as audio alarms, or turning on the lights) to wake the second user since the user 308 is already awake and therefore will not be disturbed when the control circuitry 334 attempts to wake the second user.

Still referring to FIG. 3, the control circuitry 334 for the bed 302 can utilize information for interactions with the bed 302 by multiple users to generate control signals for controlling functions of various other devices. For example, the control circuitry 334 can wait to generate control signals for, for example, engaging the security system 318, or instructing the lighting system 314 to turn off lights in various rooms until both the user 308 and a second user are detected as being present on the bed 302. As another example, the control circuitry 334 can generate a first set of control signals to cause the lighting system 314 to turn off a first set of lights upon detecting bed presence of the user 308 and generate a second set of control signals for turning off a second set of lights in response to detecting bed presence of a second user. As another example, the control circuitry 334 can wait until it has been determined that both the user 308 and a second user are awake for the day before generating control signals to open the window blinds 330. As yet another example, in response to determining that the user 308 has left the bed and is awake for the day, but that a second user is still sleeping, the control circuitry 334 can generate and transmit a first set of control signals to cause the coffee maker 324 to begin brewing coffee, to cause the security system 318 to deactivate, to turn on the lamp 326, to turn off the nightlight 328, to cause the thermostat 316 to raise the temperature in one or more rooms to 72 degrees, and to open blinds (e.g., the window blinds 330) in rooms other than the bedroom in which the bed 302 is located. Later, in response to detecting that the second user is no longer present on the bed (or that the second user is awake) the control circuitry 334 can generate and transmit a second set of control signals to, for example, cause the lighting system 314 to turn on one or more lights in the bedroom, to cause window blinds in the bedroom to open, and to turn on the television 312 to a pre-specified channel.

Examples of Data Processing Systems Associated with a Bed

Described here are examples of systems and components that can be used for data processing tasks that are, for example, associated with a bed. In some cases, multiple examples of a particular component or group of components are presented. Some of these examples are redundant and/or mutually exclusive alternatives. Connections between components are shown as examples to illustrate possible network configurations for allowing communication between components. Different formats of connections can be used as technically needed or desired. The connections generally indicate a logical connection that can be created with any technologically feasible format. For example, a network on a motherboard can be created with a printed circuit board, wireless data connections, and/or other types of network connections. Some logical connections are not shown for clarity. For example, connections with power supplies and/or computer readable memory may not be shown for clarities sake, as many or all elements of a particular component may need to be connected to the power supplies and/or computer readable memory.

Figure 4A:
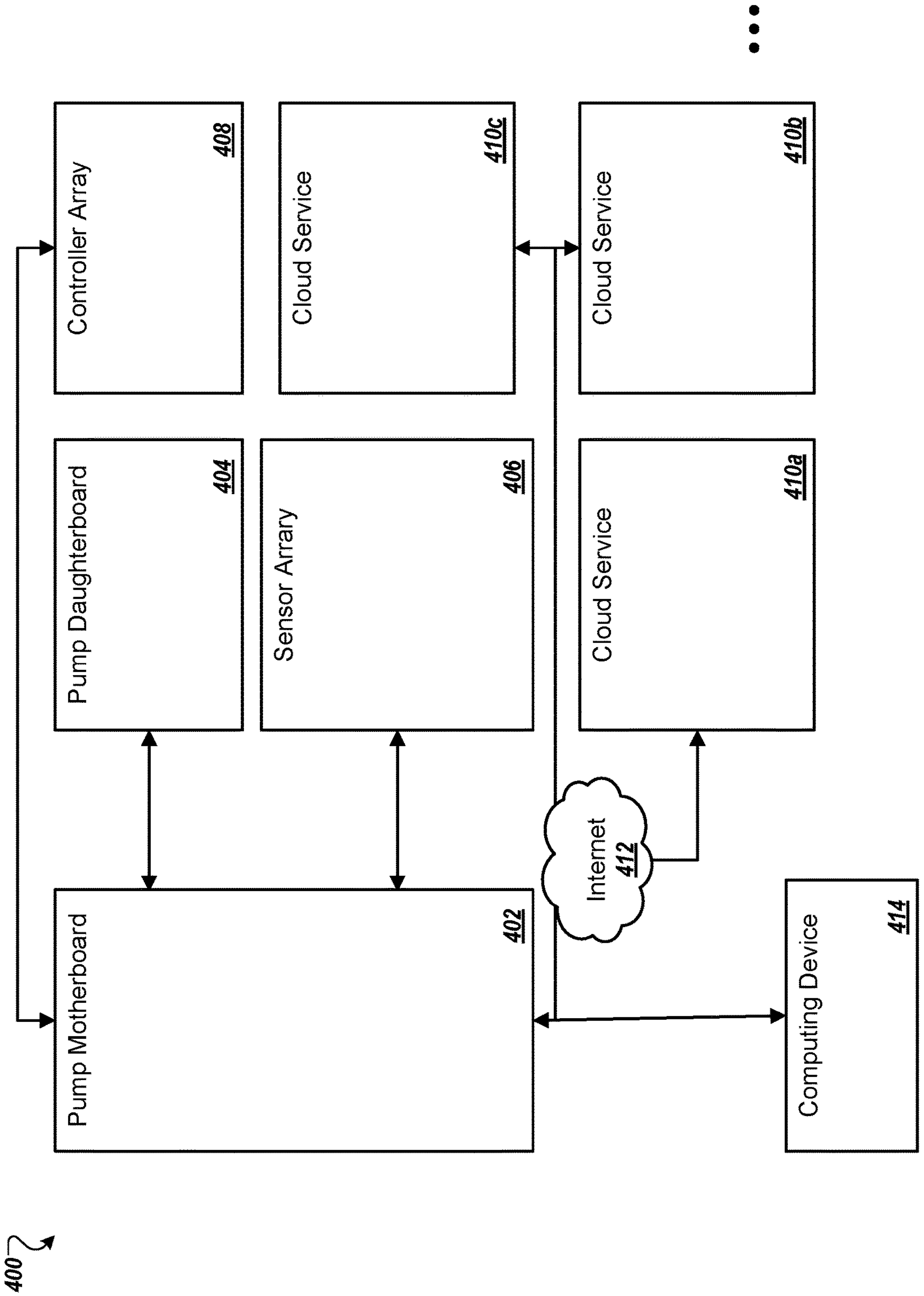
FIGS. 4A and 4B are block diagrams of example data processing systems that can be associated with a bed.

FIG. 4A is a block diagram of an example of a data processing system 400 that can be associated with a bed system, including those described above with respect to FIGS. 1-3. This system 400 includes a pump motherboard 402 and a pump daughterboard 404. The system 400 includes a sensor array 406 that can include one or more sensors configured to sense physical phenomenon of the environment and/or bed, and to report such sensing back to the pump motherboard 402 for, for example, analysis. The system 400 also includes a controller array 408 that can include one or more controllers configured to control logic-controlled devices of the bed and/or environment. The pump motherboard 400 can be in communication with one or more computing devices 414 and one or more cloud services 410 over local networks, the Internet 412, or otherwise as is technically appropriate. Each of these components will be described in more detail, some with multiple example configurations, below.

In this example, a pump motherboard 402 and a pump daughterboard 404 are communicably coupled. They can be conceptually described as a center or hub of the system 400, with the other components conceptually described as spokes of the system 400. In some configurations, this can mean that each of the spoke components communicates primarily or exclusively with the pump motherboard 402. For example, a sensor of the sensor array may not be configured to, or may not be able to, communicate directly with a corresponding controller. Instead, each spoke component can communicate with the motherboard 402. The sensor of the sensor array 406 can report a sensor reading to the motherboard 402, and the motherboard 402 can determine that, in response, a controller of the controller array 408 should adjust some parameters of a logic controlled device or otherwise modify a state of one or more peripheral devices. In one case, if the temperature of the bed is determined to be too hot, the pump motherboard 402 can determine that a temperature controller should cool the bed.

One advantage of a hub-and-spoke network configuration, sometimes also referred to as a star-shaped network, is a reduction in network traffic compared to, for example, a mesh network with dynamic routing. If a particular sensor generates a large, continuous stream of traffic, that traffic may only be transmitted over one spoke of the network to the motherboard 402. The motherboard 402 can, for example, marshal that data and condense it to a smaller data format for retransmission for storage in a cloud service 410. Additionally or alternatively, the motherboard 402 can generate a single, small, command message to be sent down a different spoke of the network in response to the large stream. For example, if the large stream of data is a pressure reading that is transmitted from the sensor array 406 a few times a second, the motherboard 402 can respond with a single command message to the controller array to increase the pressure in an air chamber. In this case, the single command message can be orders of magnitude smaller than the stream of pressure readings.

As another advantage, a hub-and-spoke network configuration can allow for an extensible network that can accommodate components being added, removed, failing, etc. This can allow, for example, more, fewer, or different sensors in the sensor array 406, controllers in the controller array 408, computing devices 414, and/or cloud services 410. For example, if a particular sensor fails or is deprecated by a newer version of the sensor, the system 400 can be configured such that only the motherboard 402 needs to be updated about the replacement sensor. This can allow, for example, product differentiation where the same motherboard 402 can support an entry level product with fewer sensors and controllers, a higher value product with more sensors and controllers, and customer personalization where a customer can add their own selected components to the system 400.

Additionally, a line of air bed products can use the system 400 with different components. In an application in which every air bed in the product line includes both a central logic unit and a pump, the motherboard 402 (and optionally the daughterboard 404) can be designed to fit within a single, universal housing. Then, for each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component will be further discussed. In some alternatives, two or more of the components of the system 400 can be realized in a single alternative component; some components can be realized in multiple, separate components; and/or some functionality can be provided by different components.

Figure 4B:
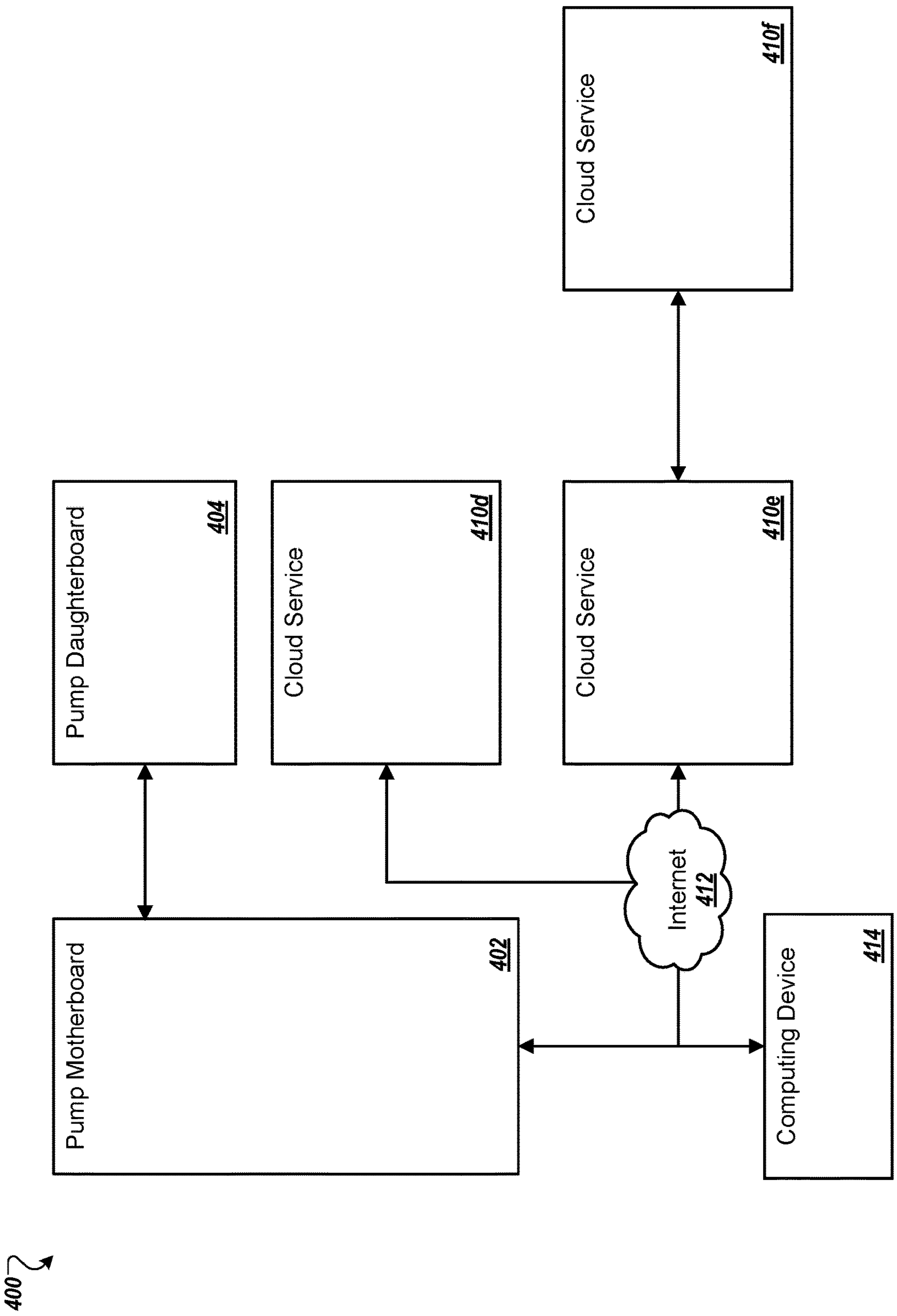

FIG. 4B is a block diagram showing some communication paths of the data processing system 400. As previously described, the motherboard 402 and the pump daughterboard 404 may act as a hub for peripheral devices and cloud services of the system 400. In cases in which the pump daughterboard 404 communicates with cloud services or other components, communications from the pump daughterboard 404 may be routed through the pump motherboard 402. This may allow, for example, the bed to have only a single connection with the internet 412. The computing device 414 may also have a connection to the internet 412, possibly through the same gateway used by the bed and/or possibly through a different gateway (e.g., a cell service provider).

Previously, a number of cloud services 410 were described. As shown in FIG. 4B, some cloud services, such as cloud services 410*d* and 410*e*, may be configured such that the pump motherboard 402 can communicate with the cloud service directly—that is the motherboard 402 may communicate with a cloud service 410 without having to use another cloud service 410 as an intermediary. Additionally or alternatively, some cloud services 410, for example cloud service 410*f*, may only be reachable by the pump motherboard 402 through an intermediary cloud service, for example cloud service 410*e*. While not shown here, some cloud services 410 may be reachable either directly or indirectly by the pump motherboard 402.

Additionally, some or all of the cloud services 410 may be configured to communicate with other cloud services. This communication may include the transfer of data and/or remote function calls according to any technologically appropriate format. For example, one cloud service 410 may request a copy for another cloud service's 410 data, for example, for purposes of backup, coordination, migration, or for performance of calculations or data mining. In another example, many cloud services 410 may contain data that is indexed according to specific users tracked by the user account cloud 410*c* and/or the bed data cloud 410*a*. These cloud services 410 may communicate with the user account cloud 410*c* and/or the bed data cloud 410*a* when accessing data specific to a particular user or bed.

Figure 5:
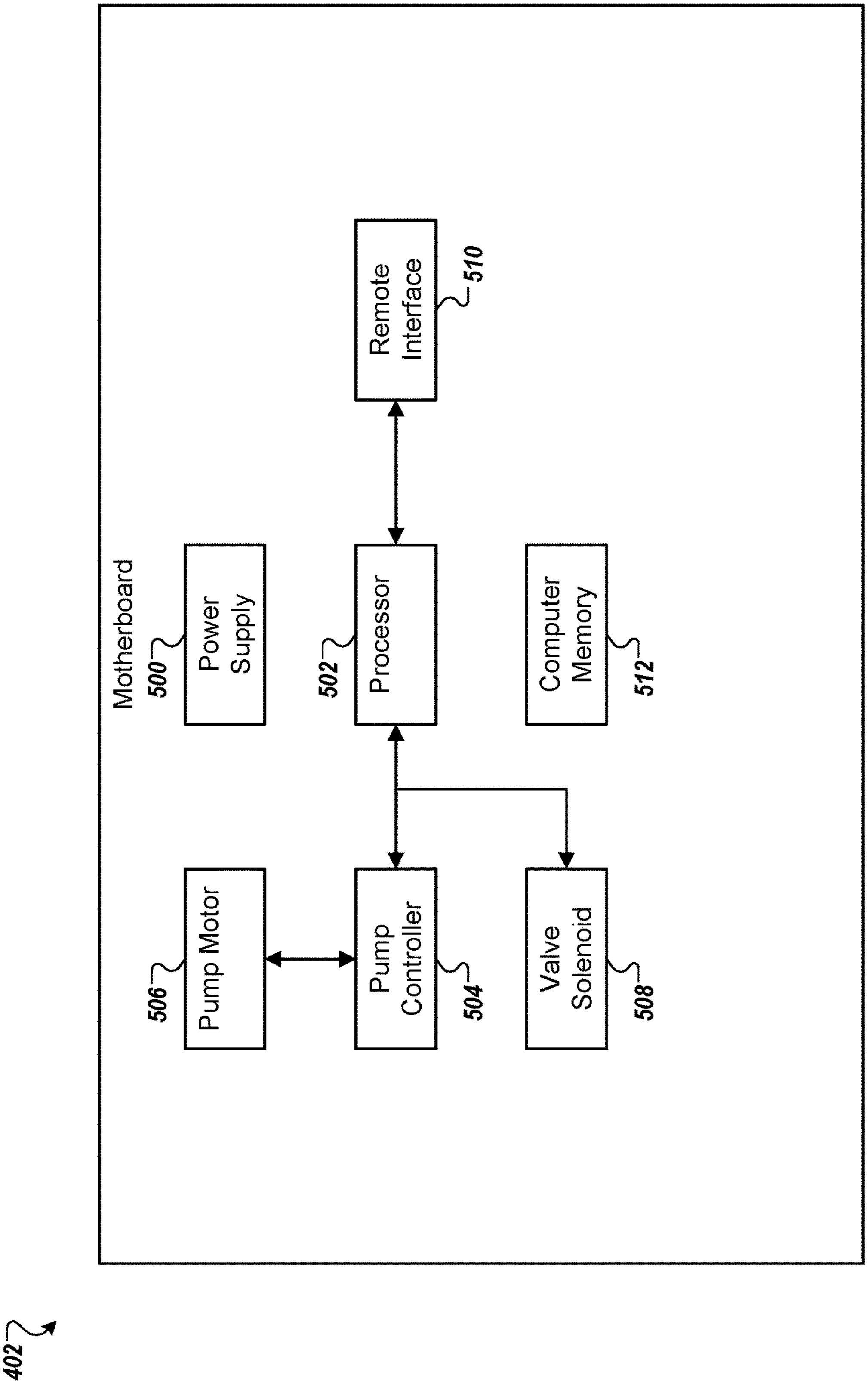
FIGS. 5 and 6 are block diagrams of examples of motherboards that can be used in a data processing system that can be associated with a bed.

FIG. 5 is a block diagram of an example of a motherboard 402 that can be used in a data processing system that can be associated with a bed system, including those described above with respect to FIGS. 1-3. In this example, compared to other examples described below, this motherboard 402 consists of relatively fewer parts and can be limited to provide a relatively limited feature set.

The motherboard includes a power supply 500, a processor 502, and computer memory 512. In general, the power supply includes hardware used to receive electrical power from an outside source and supply it to components of the motherboard 402. The power supply can include, for example, a battery pack and/or wall outlet adapter, an AC to DC converter, a DC to AC converter, a power conditioner, a capacitor bank, and/or one or more interfaces for providing power in the current type, voltage, etc., needed by other components of the motherboard 402.

The processor 502 is generally a device for receiving input, performing logical determinations, and providing output. The processor 502 can be a central processing unit, a microprocessor, general purpose logic circuity, application-specific integrated circuity, a combination of these, and/or other hardware for performing the functionality needed.

The memory 512 is generally one or more devices for storing data. The memory 512 can include long term stable data storage (e.g., on a hard disk), short term unstable (e.g., on Random Access Memory) or any other technologically appropriate configuration.

The motherboard 402 includes a pump controller 504 and a pump motor 506. The pump controller 504 can receive commands from the processor 502 and, in response, control the function of the pump motor 506. For example, the pump controller 504 can receive, from the processor 502, a command to increase the pressure of an air chamber by 0.3 pounds per square inch (PSI). The pump controller 504, in response, engages a valve so that the pump motor 506 is configured to pump air into the selected air chamber, and can engage the pump motor 506 for a length of time that corresponds to 0.3 PSI or until a sensor indicates that pressure has been increased by 0.3 PSI. In an alternative configuration, the message can specify that the chamber should be inflated to a target PSI, and the pump controller 504 can engage the pump motor 506 until the target PSI is reached.

A valve solenoid 508 can control which air chamber a pump is connected to. In some cases, the solenoid 508 can be controlled by the processor 502 directly. In some cases, the solenoid 508 can be controlled by the pump controller 504.

A remote interface 510 of the motherboard 402 can allow the motherboard 402 to communicate with other components of a data processing system. For example, the motherboard 402 can be able to communicate with one or more daughterboards, with peripheral sensors, and/or with peripheral controllers through the remote interface 510. The remote interface 510 can provide any technologically appropriate communication interface, including but not limited to multiple communication interfaces such as WiFi, Bluetooth, and copper wired networks.

Figure 6:
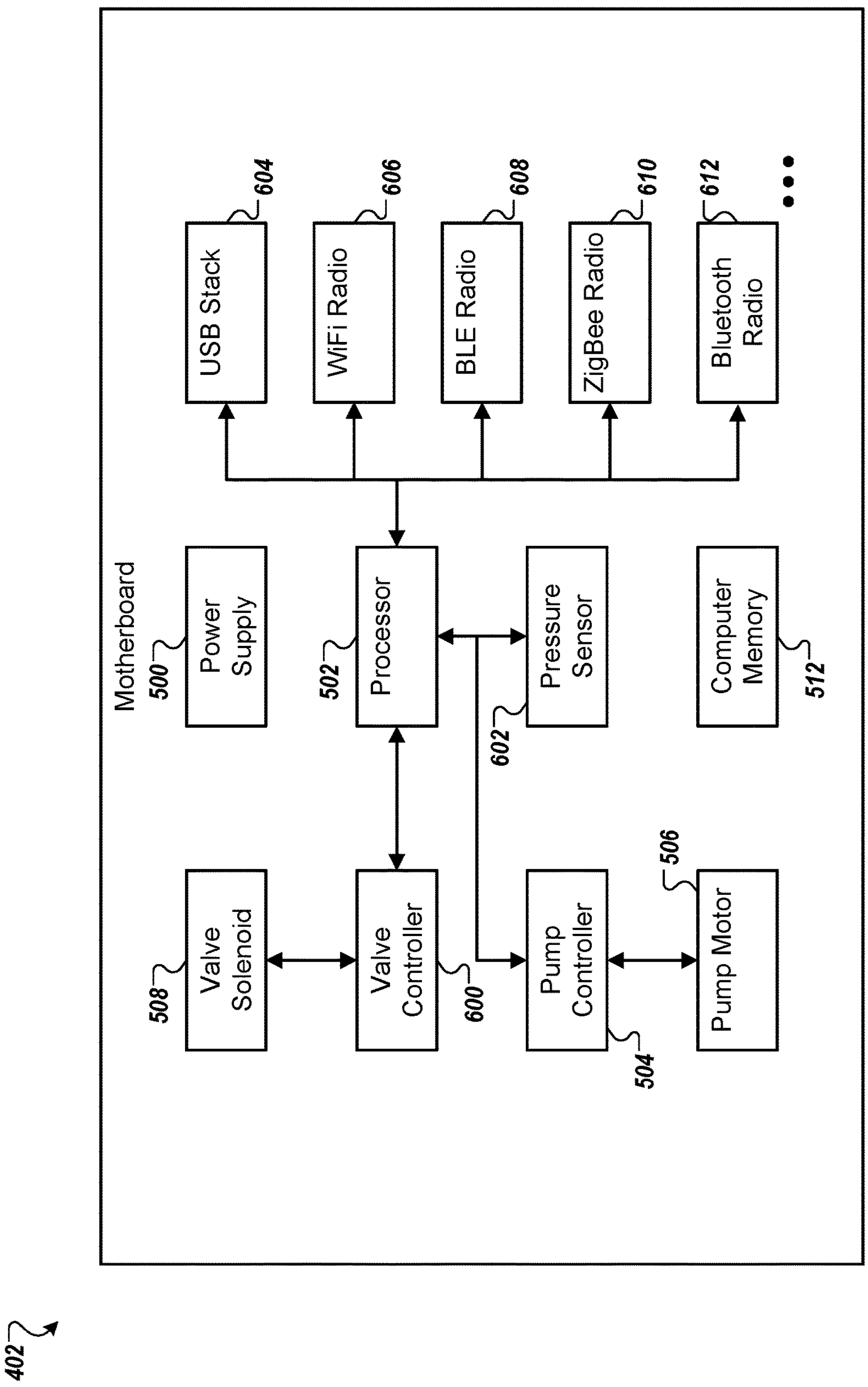

FIG. 6 is a block diagram of an example of a motherboard 402 that can be used in a data processing system that can be associated with a bed system, including those described above with respect to FIGS. 1-3. Compared to the motherboard 402 described with reference to FIG. 5, the motherboard in FIG. 6 can contain more components and provide more functionality in some applications.

In addition to the power supply 500, processor 502, pump controller 504, pump motor 506, and valve solenoid 508, this motherboard 402 is shown with a valve controller 600, a pressure sensor 602, a universal serial bus (USB) stack 604, a WiFi radio 606, a Bluetooth Low Energy (BLE) radio 608, a ZigBee radio 610, a Bluetooth radio 612 and a computer memory 512.

Similar to the way that the pump controller 504 converts commands from the processor 502 into control signals for the pump motor 506, the valve controller 600 can convert commands from the processor 502 into control signals for the valve solenoid 508. In one example, the processor 502 can issue a command to the valve controller 600 to connect the pump to a particular air chamber out of the group of air chambers in an air bed. The valve controller 600 can control the position of the valve solenoid 508 so that the pump is connected to the indicated air chamber.

The pressure sensor 602 can read pressure readings from one or more air chambers of the air bed. The pressure sensor 602 can also preform digital sensor conditioning.

The motherboard 402 can include a suite of network interfaces, including but not limited to those shown here. These network interfaces can allow the motherboard to communicate over a wired or wireless network with any number of devices, including but not limited to peripheral sensors, peripheral controllers, computing devices, and devices and services connected to the Internet 412.

Figure 7:
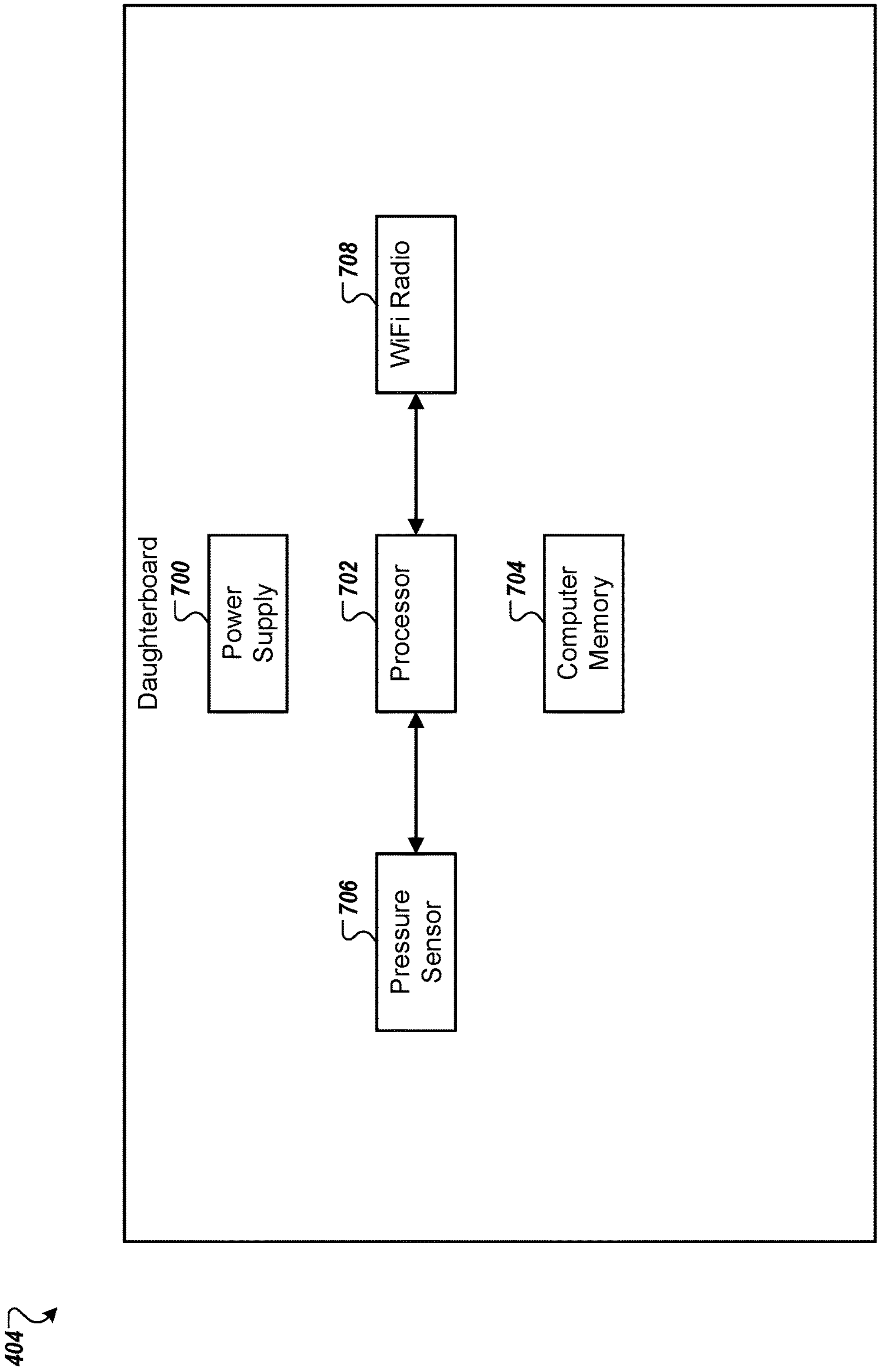
FIG. 7 is a block diagram of an example of a daughterboard that can be used in a data processing system that can be associated with a bed.

FIG. 7 is a block diagram of an example of a daughterboard 404 that can be used in a data processing system that can be associated with a bed system, including those described above with respect to FIGS. 1-3. In some configurations, one or more daughterboards 404 can be connected to the motherboard 402. Some daughterboards 404 can be designed to offload particular and/or compartmentalized tasks from the motherboard 402. This can be advantageous, for example, if the particular tasks are computationally intensive, proprietary, or subject to future revisions. For example, the daughterboard 404 can be used to calculate a particular sleep data metric. This metric can be computationally intensive, and calculating the sleep metric on the daughterboard 404 can free up the resources of the motherboard 402 while the metric is being calculated. Additionally and/or alternatively, the sleep metric can be subject to future revisions. To update the system 400 with the new sleep metric, it is possible that only the daughterboard 404 that calculates that metric need be replaced. In this case, the same motherboard 402 and other components can be used, saving the need to perform unit testing of additional components instead of just the daughterboard 404.

The daughterboard 404 is shown with a power supply 700, a processor 702, computer readable memory 704, a pressure sensor 706, and a WiFi radio 708. The processor can use the pressure sensor 706 to gather information about the pressure of the air chamber or chambers of an air bed. From this data, the processor 702 can perform an algorithm to calculate a sleep metric. In some examples, the sleep metric can be calculated from only the pressure of air chambers. In other examples, the sleep metric can be calculated from one or more other sensors. In an example in which different data is needed, the processor 702 can receive that data from an appropriate sensor or sensors. These sensors can be internal to the daughterboard 404, accessible via the WiFi radio 708, or otherwise in communication with the processor 702. Once the sleep metric is calculated, the processor 702 can report that sleep metric to, for example, the motherboard 402.

Figure 8:
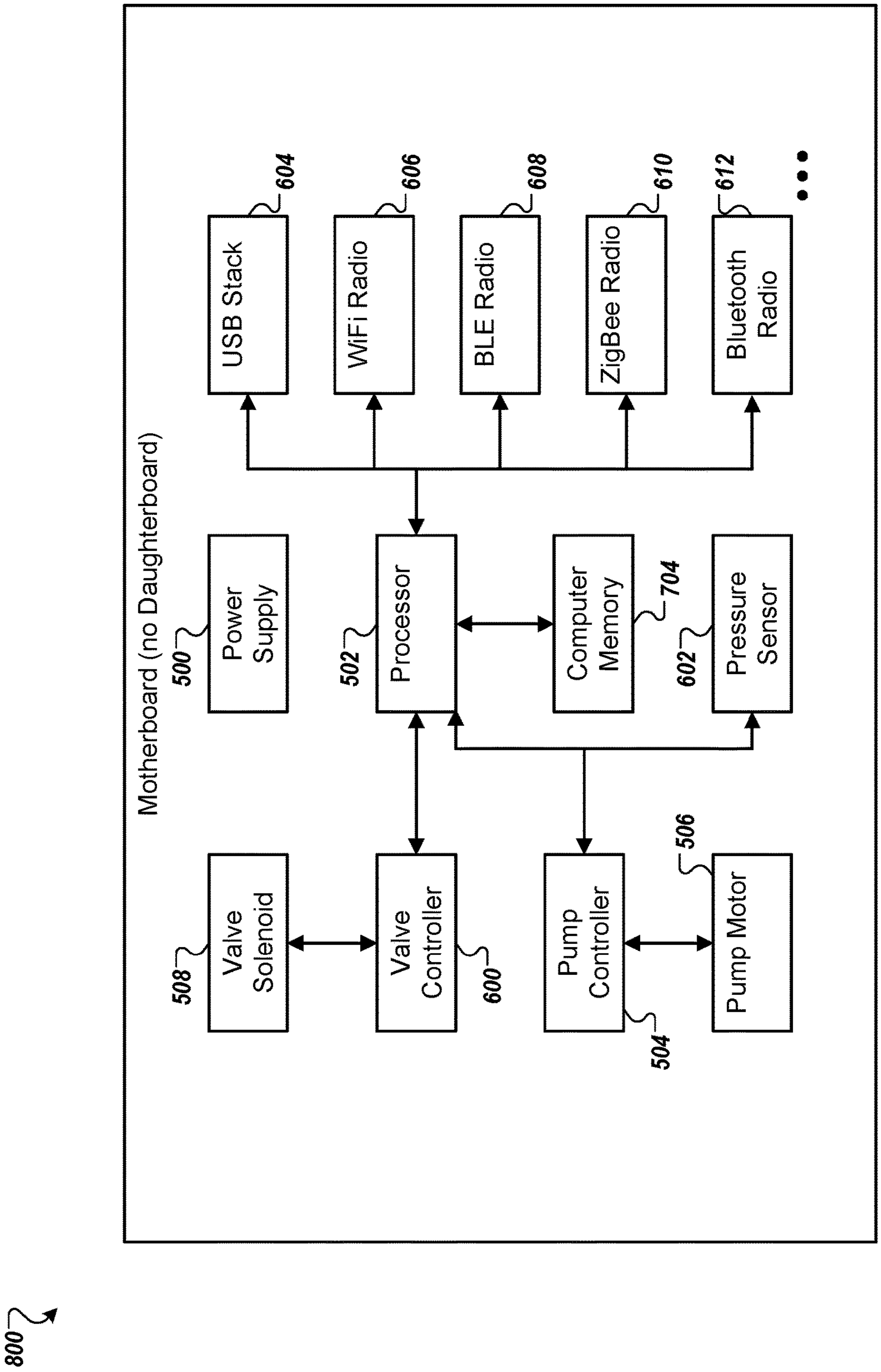
FIG. 8 is a block diagram of an example of a motherboard with no daughterboard that can be used in a data processing system that can be associated with a bed.

FIG. 8 is a block diagram of an example of a motherboard 800 with no daughterboard that can be used in a data processing system that can be associated with a bed system, including those described above with respect to FIGS. 1-3. In this example, the motherboard 800 can perform most, all, or more of the features described with reference to the motherboard 402 in FIG. 6 and the daughterboard 404 in FIG. 7.

Figure 9:
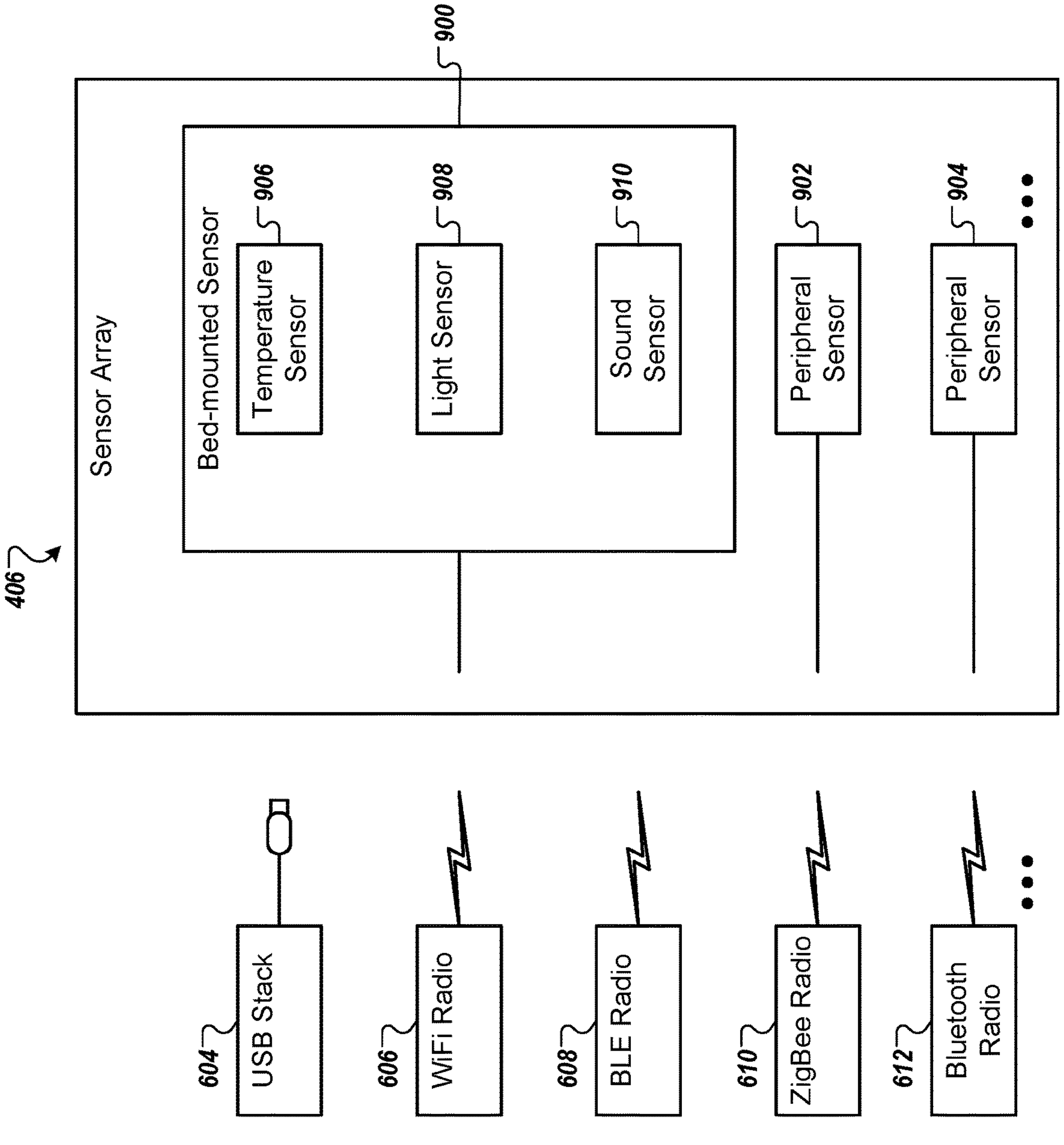
FIG. 9 is a block diagram of an example of a sensory array that can be used in a data processing system that can be associated with a bed.

FIG. 9 is a block diagram of an example of a sensory array 406 that can be used in a data processing system that can be associated with a bed system, including those described above with respect to FIGS. 1-3. In general, the sensor array 406 is a conceptual grouping of some or all the peripheral sensors that communicate with the motherboard 402 but are not native to the motherboard 402.

The peripheral sensors of the sensor array 406 can communicate with the motherboard 402 through one or more of the network interfaces of the motherboard, including but not limited to the USB stack 604, a WiFi radio 606, a Bluetooth Low Energy (BLE) radio 608, a ZigBee radio 610, and a Bluetooth radio 612, as is appropriate for the configuration of the particular sensor. For example, a sensor that outputs a reading over a USB cable can communicate through the USB stack 604.

Some of the peripheral sensors 900 of the sensor array 406 can be bed mounted 900. These sensors can be, for example, embedded into the structure of a bed and sold with the bed, or later affixed to the structure of the bed. Other peripheral sensors 902 and 904 can be in communication with the motherboard 402, but optionally not mounted to the bed. In some cases, some or all of the bed mounted sensors 900 and/or peripheral sensors 902 and 904 can share networking hardware, including a conduit that contains wires from each sensor, a multi-wire cable or plug that, when affixed to the motherboard 402, connect all of the associated sensors with the motherboard 402. In some embodiments, one, some, or all of sensors 902, 904, 906, 908, and 910 can sense one or more features of a mattress, such as pressure, temperature, light, sound, and/or one or more other features of the mattress. In some embodiments, one, some, or all of sensors 902, 904, 906, 908, and 910 can sense one or more features external to the mattress. In some embodiments, pressure sensor 902 can sense pressure of the mattress while some or all of sensors 902, 904, 906, 908, and 910 can sense one or more features of the mattress and/or external to the mattress.

Figure 10:
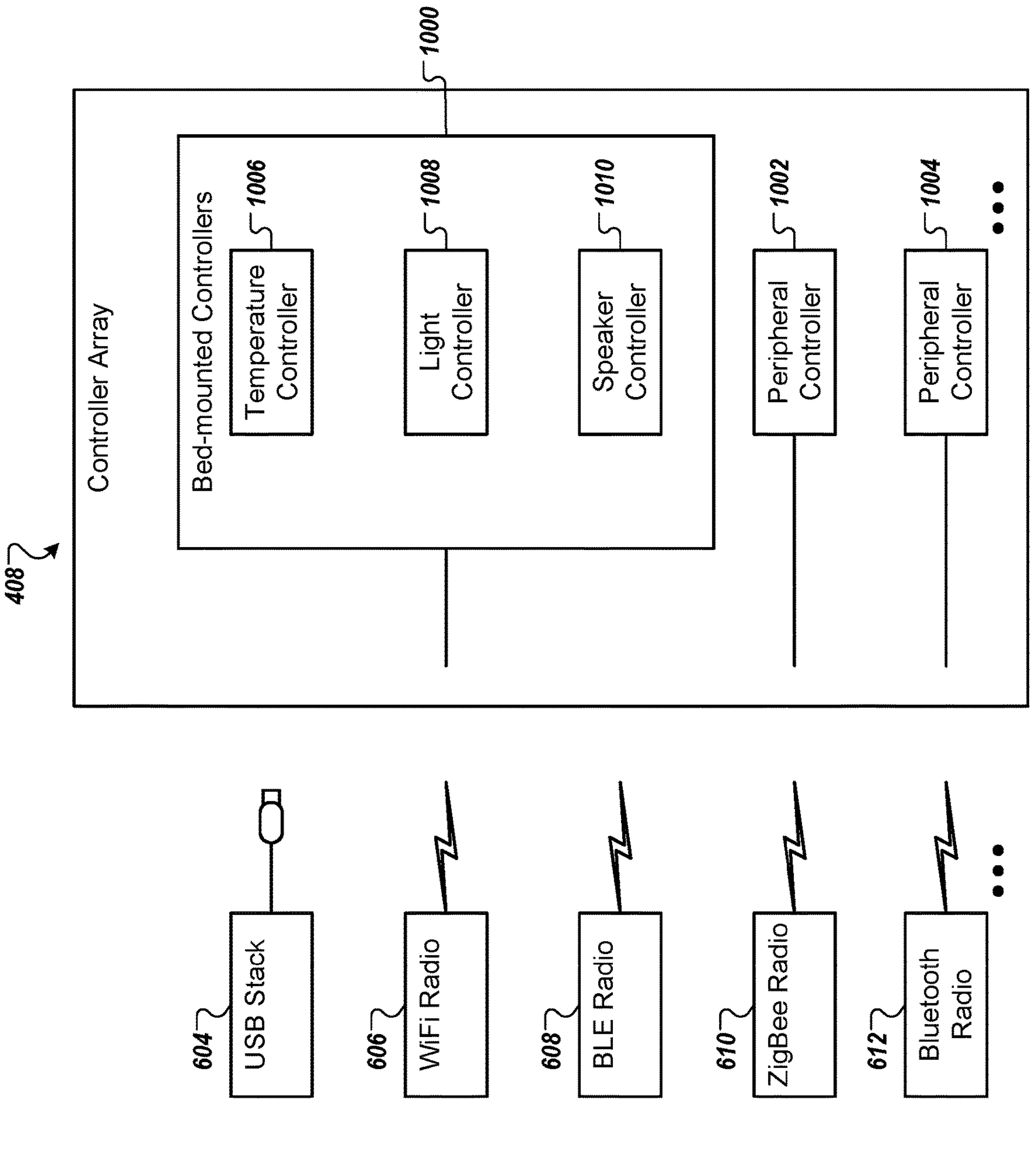
FIG. 10 is a block diagram of an example of a control array that can be used in a data processing system that can be associated with a bed

FIG. 10 is a block diagram of an example of a controller array 408 that can be used in a data processing system that can be associated with a bed system, including those described above with respect to FIGS. 1-3. In general, the controller array 408 is a conceptual grouping of some or all peripheral controllers that communicate with the motherboard 402 but are not native to the motherboard 402.

The peripheral controllers of the controller array 408 can communicate with the motherboard 402 through one or more of the network interfaces of the motherboard, including but not limited to the USB stack 604, a WiFi radio 606, a Bluetooth Low Energy (BLE) radio 608, a ZigBee radio 610, and a Bluetooth radio 612, as is appropriate for the configuration of the particular sensor. For example, a controller that receives a command over a USB cable can communicate through the USB stack 604.

Some of the controllers of the controller array 408 can be bed mounted 1000. These controllers can be, for example, embedded into the structure of a bed and sold with the bed, or later affixed to the structure of the bed. Other peripheral controllers 1002 and 1004 can be in communication with the motherboard 402, but optionally not mounted to the bed. In some cases, some or all of the bed mounted controllers 1000 and/or peripheral controllers 1002 and 1004 can share networking hardware, including a conduit that contains wires for each controller, a multi-wire cable or plug that, when affixed to the motherboard 402, connects all of the associated controllers with the motherboard 402.

Figure 11:
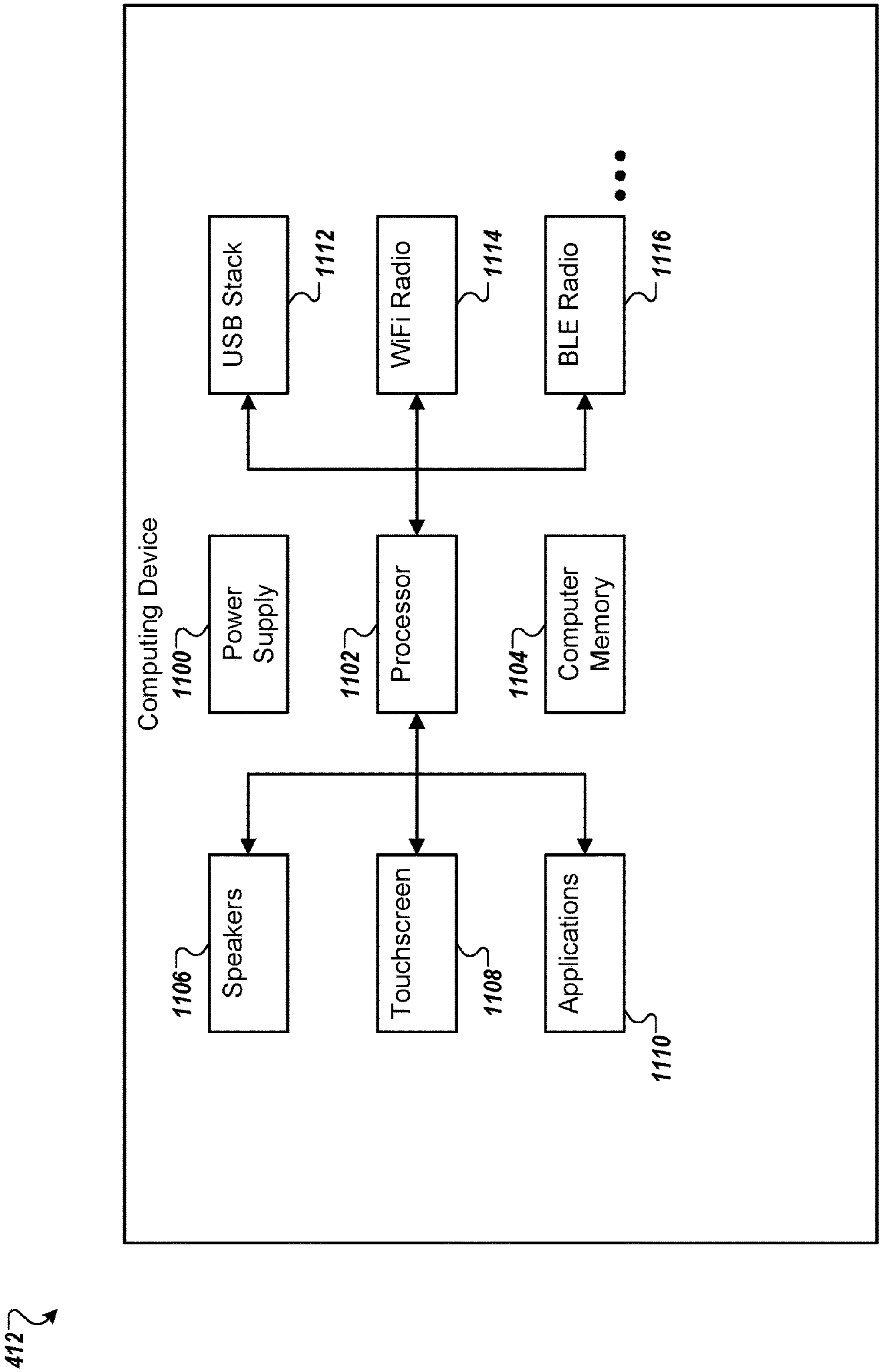
FIG. 11 is a block diagram of an example of a computing device that can be used in a data processing system that can be associated with a bed.

FIG. 11 is a block diagram of an example of a computing device 412 that can be used in a data processing system that can be associated with a bed system, including those described above with respect to FIGS. 1-3. The computing device 412 can include, for example, computing devices used by a user of a bed. Example computing devices 412 include, but are not limited to, mobile computing devices (e.g., mobile phones, tablet computers, laptops) and desktop computers.

The computing device 412 includes a power supply 1100, a processor 1102, and computer readable memory 1104. User input and output can be transmitted by, for example, speakers 1106, a touchscreen 1108, or other not shown components such as a pointing device or keyboard. The computing device 412 can run one or more applications 1110. These applications can include, for example, application to allow the user to interact with the system 400. These applications can allow a user to view information about the bed (e.g., sensor readings, sleep metrics), or configure the behavior of the system 400 (e.g., set a desired firmness to the bed, set desired behavior for peripheral devices). In some cases, the computing device 412 can be used in addition to, or to replace, the remote control 122 described previously.

Figure 12:
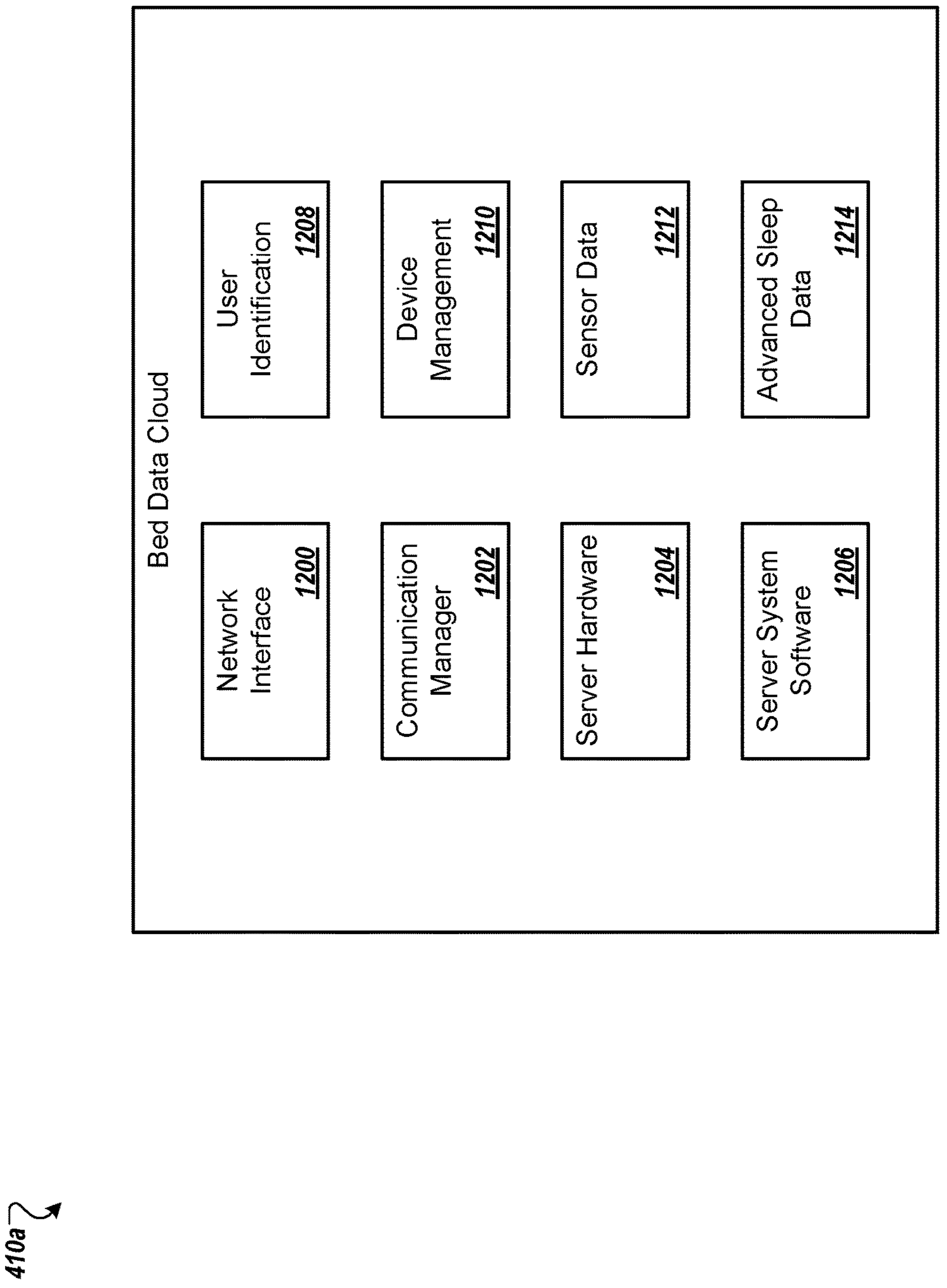
FIGS. 12-16 are block diagrams of example cloud services that can be used in a data processing system that can be associated with a bed.

FIG. 12 is a block diagram of an example bed data cloud service **410*a* that can be used in a data processing system that can be associated with a bed system, including those described above with respect to FIGS. 1-3. In this example, the bed data cloud service 410*a*** is configured to collect sensor data and sleep data from a particular bed, and to match the sensor and sleep data with one or more users that use the bed when the sensor and sleep data was generated.

The bed data cloud service **410*a* is shown with a network interface 1200, a communication manager 1202, server hardware 1204, and server system software 1206. In addition, the bed data cloud service 410*a* is shown with a user identification module 1208, a device management 1210 module, a sensor data module 1210, and an advanced sleep data module 1214**.

The network interface 1200 generally includes hardware and low level software used to allow one or more hardware devices to communicate over networks. For example, the network interface 1200 can include network cards, routers, modems, and other hardware needed to allow the components of the bed data cloud service 410*a* to communicate with each other and other destinations over, for example, the Internet 412. The communication manger 1202 generally comprises hardware and software that operate above the network interface 1200. This includes software to initiate, maintain, and tear down network communications used by the bed data cloud service 410*a*. This includes, for example, TCP/IP, SSL or TLS, Torrent, and other communication sessions over local or wide area networks. The communication manger 1202 can also provide load balancing and other services to other elements of the bed data cloud service 410*a*.

The server hardware 1204 generally includes the physical processing devices used to instantiate and maintain bed data cloud service 410*a*. This hardware includes, but is not limited to processors (e.g., central processing units, ASICs, graphical processers), and computer readable memory (e.g., random access memory, stable hard disks, tape backup). One or more servers can be configured into clusters, multi-computer, or datacenters that can be geographically separate or connected.

The server system software 1206 generally includes software that runs on the server hardware 1204 to provide operating environments to applications and services. The server system software 1206 can include operating systems running on real servers, virtual machines instantiated on real servers to create many virtual servers, server level operations such as data migration, redundancy, and backup.

The user identification 1208 can include, or reference, data related to users of beds with associated data processing systems. For example, the users can include customers, owners, or other users registered with the bed data cloud service 410*a* or another service. Each user can have, for example, a unique identifier, user credentials, contact information, billing information, demographic information, or any other technologically appropriate information.

The device manager 1210 can include, or reference, data related to beds or other products associated with data processing systems. For example, the beds can include products sold or registered with a system associated with the bed data cloud service 410*a*. Each bed can have, for example, a unique identifier, model and/or serial number, sales information, geographic information, delivery information, a listing of associated sensors and control peripherals, etc. Additionally, an index or indexes stored by the bed data cloud service 410*a* can identify users that are associated with beds. For example, this index can record sales of a bed to a user, users that sleep in a bed, etc.

The sensor data 1212 can record raw or condensed sensor data recorded by beds with associated data processing systems. For example, a bed's data processing system can have a temperature sensor, pressure sensor, and light sensor. Readings from these sensors, either in raw form or in a format generated from the raw data (e.g. sleep metrics) of the sensors, can be communicated by the bed's data processing system to the bed data cloud service 410*a* for storage in the sensor data 1212. Additionally, an index or indexes stored by the bed data cloud service 410*a* can identify users and/or beds that are associated with the sensor data 1212.

The bed data cloud service 410*a* can use any of its available data to generate advanced sleep data 1214. In general, the advanced sleep data 1214 includes sleep metrics and other data generated from sensor readings. Some of these calculations can be performed in the bed data cloud service 410*a* instead of locally on the bed's data processing system, for example, because the calculations are computationally complex or require a large amount of memory space or processor power that is not available on the bed's data processing system. This can help allow a bed system to operate with a relatively simple controller and still be part of a system that performs relatively complex tasks and computations.

Figure 13:
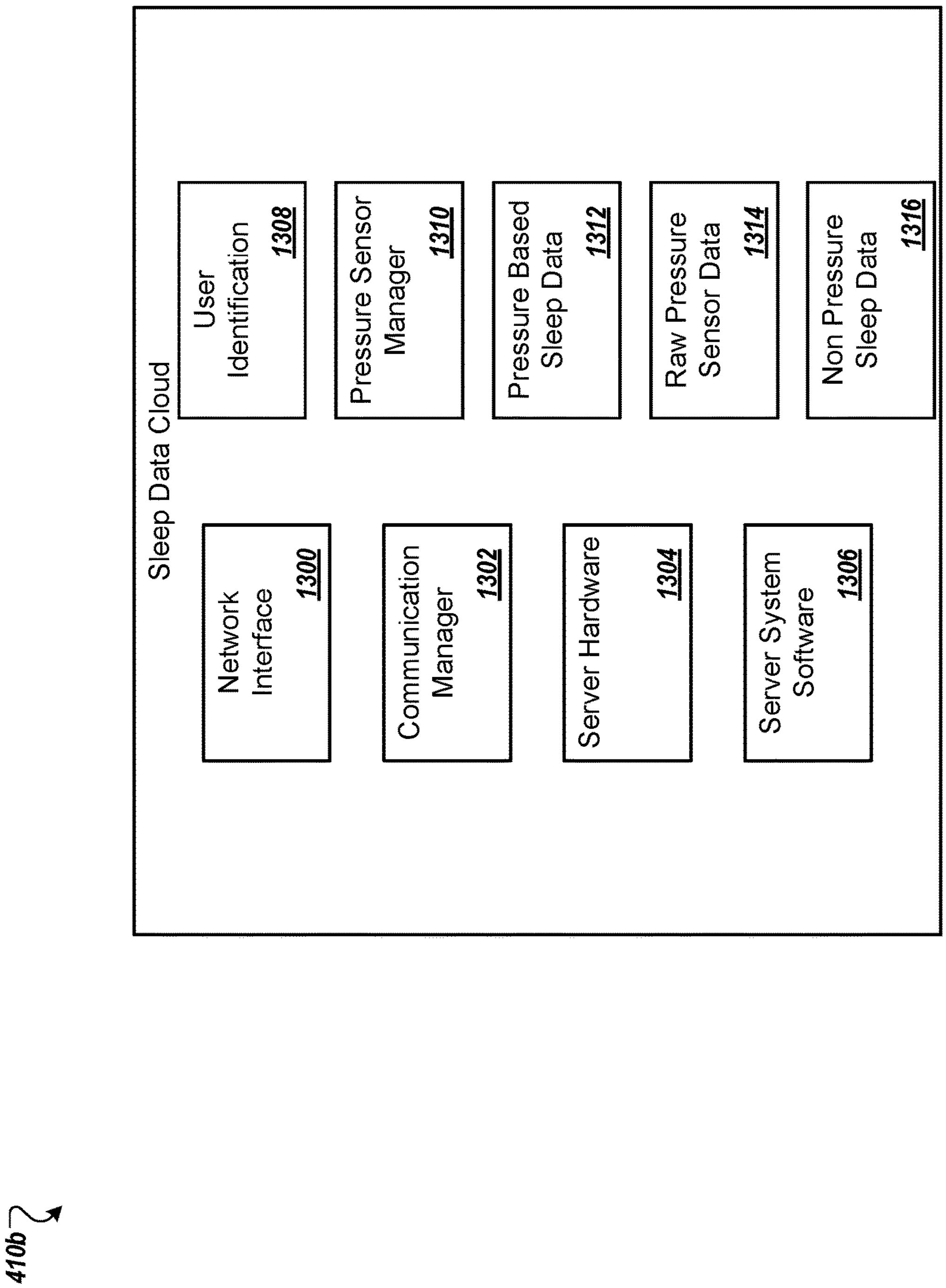

FIG. 13 is a block diagram of an example sleep data cloud service 410*b* that can be used in a data processing system that can be associated with a bed system, including those described above with respect to FIGS. 1-3. In this example, the sleep data cloud service 410*b* is configured to record data related to users' sleep experience.

The sleep data cloud service 410*b* is shown with a network interface 1300, a communication manager 1302, server hardware 1304, and server system software 1306. In addition, the sleep data cloud service 410*b* is shown with a user identification module 1308, a pressure sensor manager 1310, a pressure based sleep data module 1312, a raw pressure sensor data module 1314, and a non-pressure sleep data module 1316.

The pressure sensor manager 1310 can include, or reference, data related to the configuration and operation of pressure sensors in beds. For example, this data can include an identifier of the types of sensors in a particular bed, their settings and calibration data, etc.

The pressure based sleep data 1312 can use raw pressure sensor data 1314 to calculate sleep metrics specifically tied to pressure sensor data. For example, user presence, movements, weight change, heart rate, and breathing rate can all be determined from raw pressure sensor data 1314. Additionally, an index or indexes stored by the sleep data cloud service 410*b* can identify users that are associated with pressure sensors, raw pressure sensor data, and/or pressure based sleep data.

The non-pressure sleep data 1316 can use other sources of data to calculate sleep metrics. For example, user entered preferences, light sensor readings, and sound sensor readings can all be used to track sleep data. Additionally, an index or indexes stored by the sleep data cloud service 410*b* can identify users that are associated with other sensors and/or non-pressure sleep data 1316.

Figure 14:
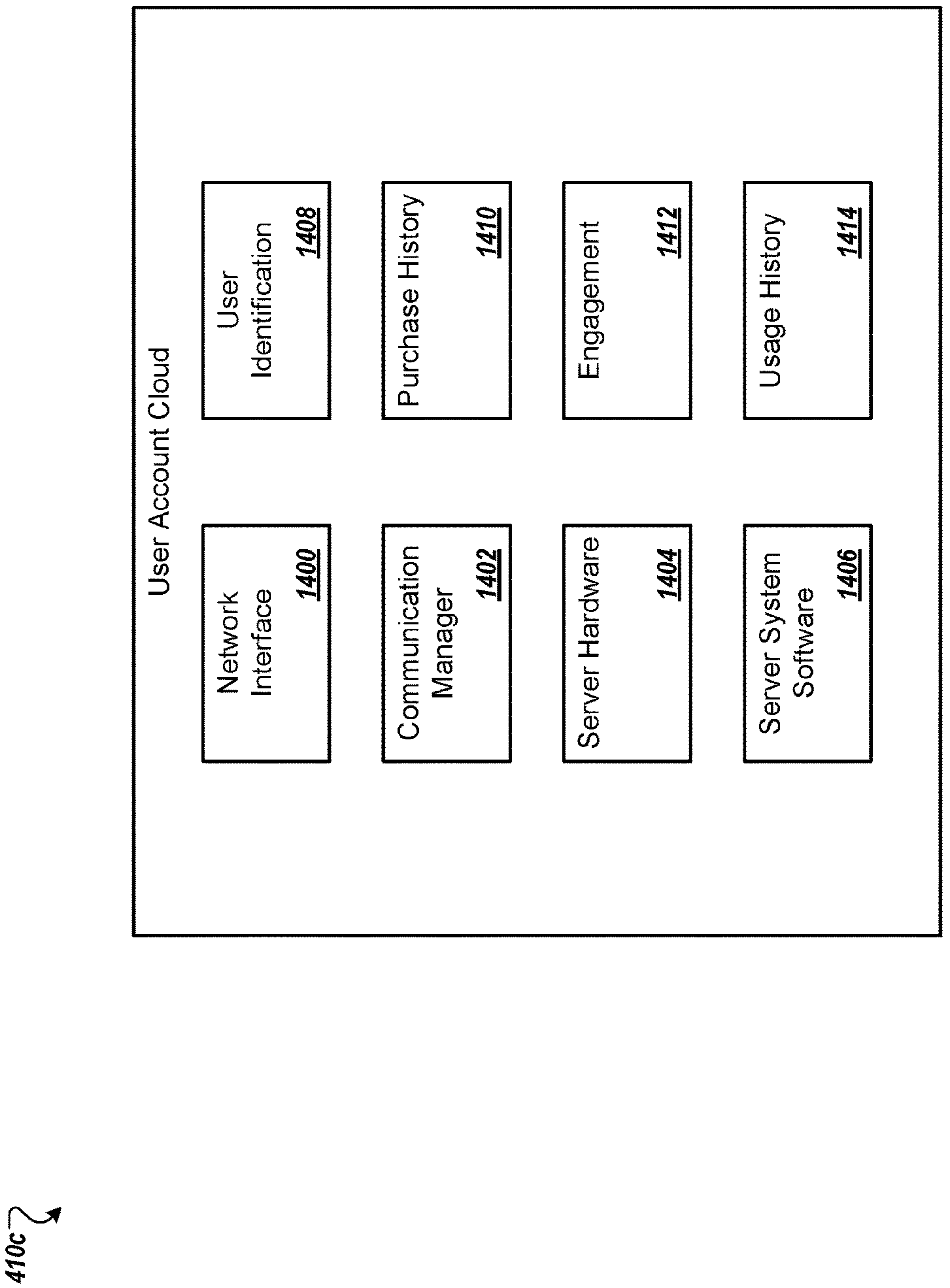

FIG. 14 is a block diagram of an example user account cloud service 410*c* that can be used in a data processing system that can be associated with a bed system, including those described above with respect to FIGS. 1-3. In this example, the user account cloud service 410*c* is configured to record a list of users and to identify other data related to those users.

The user account cloud service 410*c* is shown with a network interface 1400, a communication manager 1402, server hardware 1404, and server system software 1406. In addition, the user account cloud service 410*c* is shown with a user identification module 1408, a purchase history module 1410, an engagement module 1412, and an application usage history module 1414.

The user identification module 1408 can include, or reference, data related to users of beds with associated data processing systems. For example, the users can include customers, owners, or other users registered with the user account cloud service 410*a* or another service. Each user can have, for example, a unique identifier, and user credentials, demographic information, or any other technologically appropriate information.

The purchase history module 1410 can include, or reference, data related to purchases by users. For example, the purchase data can include a sale's contact information, billing information, and salesperson information. Additionally, an index or indexes stored by the user account cloud service 410*c* can identify users that are associated with a purchase.

The engagement 1412 can track user interactions with the manufacturer, vendor, and/or manager of the bed and or cloud services. This engagement data can include communications (e.g., emails, service calls), data from sales (e.g., sales receipts, configuration logs), and social network interactions.

The usage history module 1414 can contain data about user interactions with one or more applications and/or remote controls of a bed. For example, a monitoring and configuration application can be distributed to run on, for example, computing devices 412. This application can log and report user interactions for storage in the application usage history module 1414. Additionally, an index or indexes stored by the user account cloud service 410*c* can identify users that are associated with each log entry.

Figure 15:
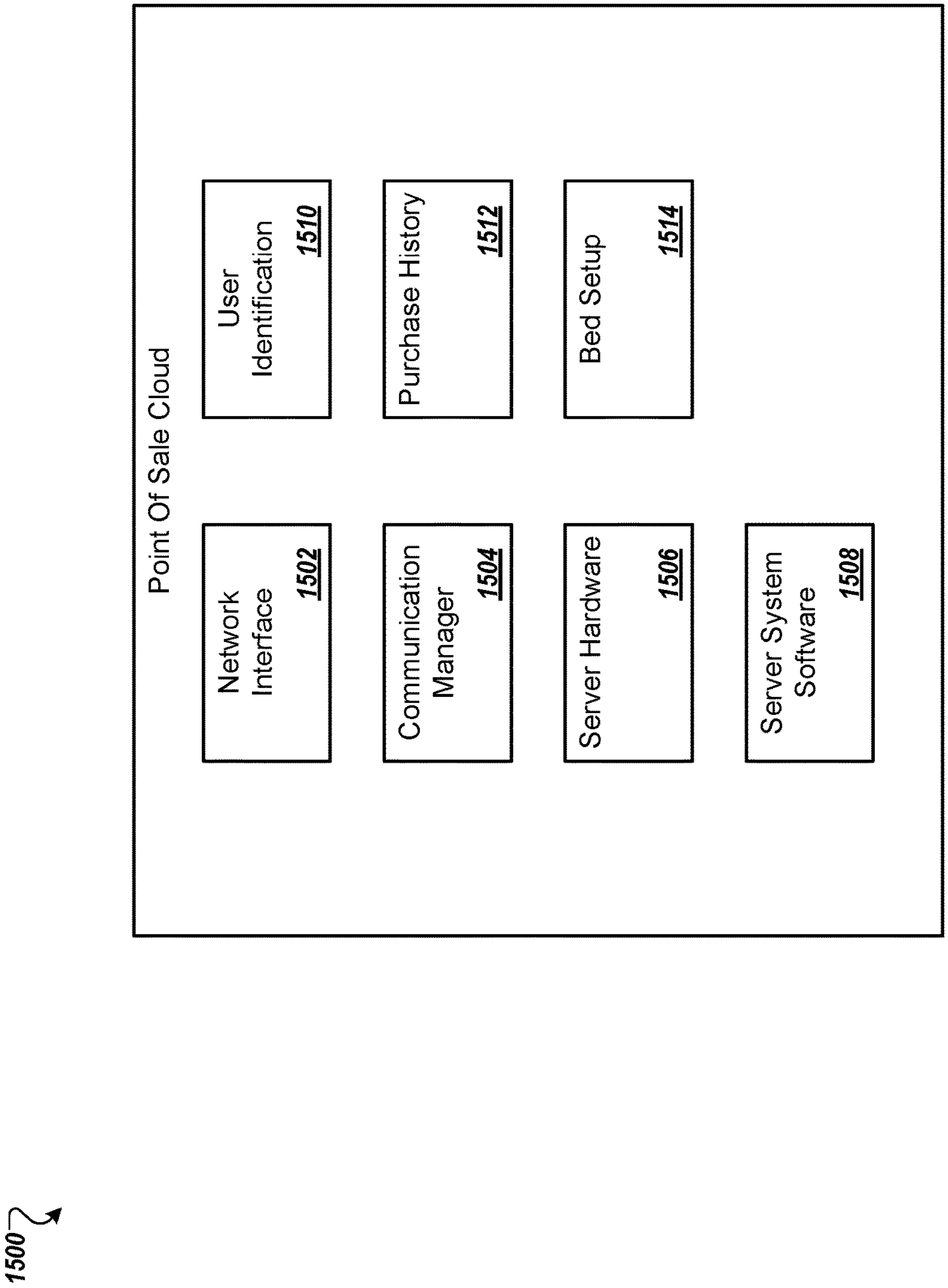

FIG. 15 is a block diagram of an example point of sale cloud service 1500 that can be used in a data processing system that can be associated with a bed system, including those described above with respect to FIGS. 1-3. In this example, the point of sale cloud service 1500 is configured to record data related to users' purchases.

The point of sale cloud service 1500 is shown with a network interface 1502, a communication manager 1504, server hardware 1506, and server system software 1508. In addition, the point of sale cloud service 1500 is shown with a user identification module 1510, a purchase history module 1512, and a setup module 1514.

The purchase history module 1512 can include, or reference, data related to purchases made by users identified in the user identification module 1510. The purchase information can include, for example, data of a sale, price, and location of sale, delivery address, and configuration options selected by the users at the time of sale. These configuration options can include selections made by the user about how they wish their newly purchased beds to be setup and can include, for example, expected sleep schedule, a listing of peripheral sensors and controllers that they have or will install, etc.

The bed setup module 1514 can include, or reference, data related to installations of beds that users' purchase. The bed setup data can include, for example, the date and address to which a bed is delivered, the person that accepts delivery, the configuration that is applied to the bed upon delivery, the name or names of the person or people who will sleep on the bed, which side of the bed each person will use, etc.

Data recorded in the point of sale cloud service 1500 can be referenced by a user's bed system at later dates to control functionality of the bed system and/or to send control signals to peripheral components according to data recorded in the point of sale cloud service 1500. This can allow a salesperson to collect information from the user at the point of sale that later facilitates automation of the bed system. In some examples, some or all aspects of the bed system can be automated with little or no user-entered data required after the point of sale. In other examples, data recorded in the point of sale cloud service 1500 can be used in connection with a variety of additional data gathered from user-entered data.

Figure 16:
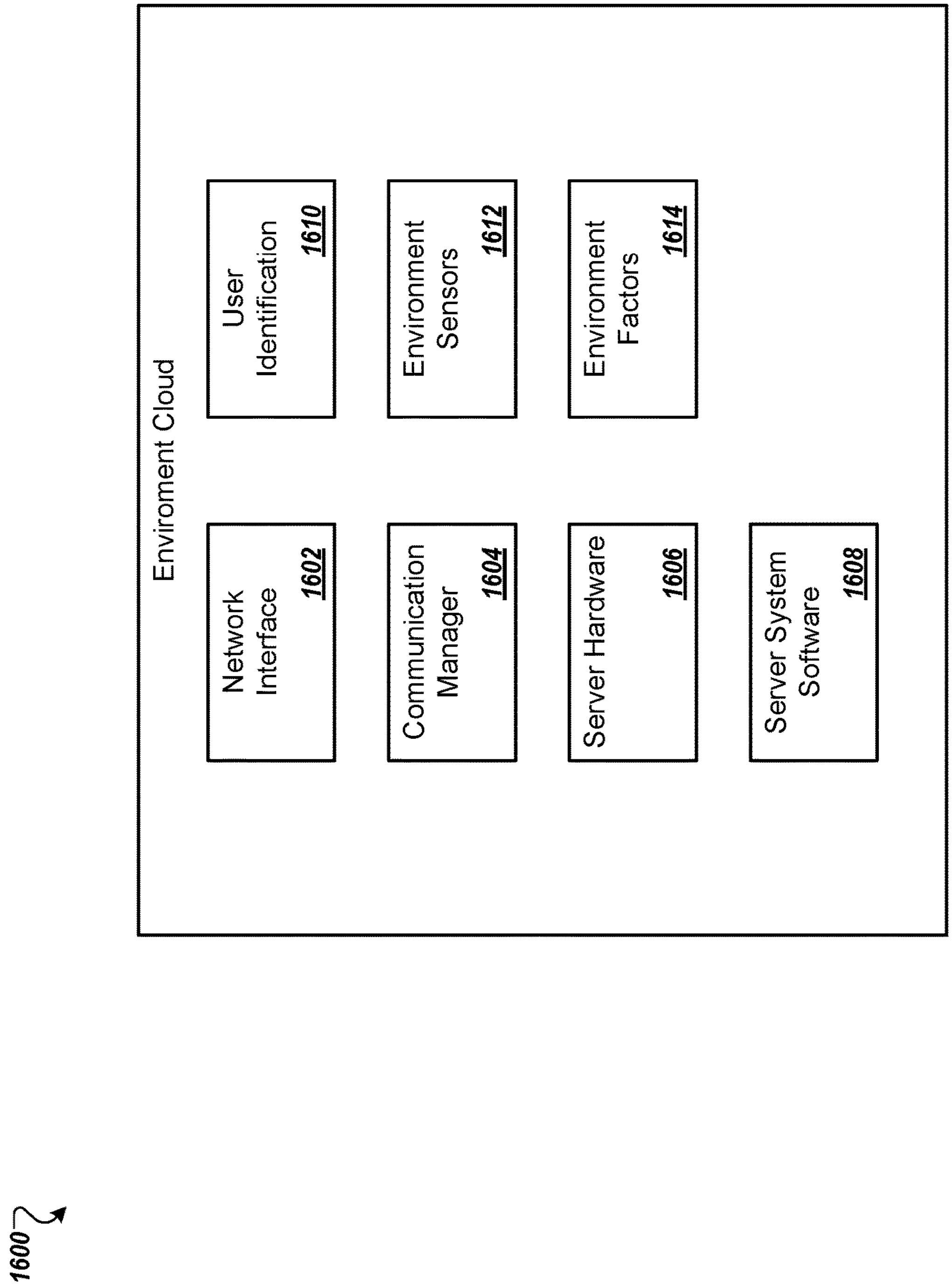

FIG. 16 is a block diagram of an example environment cloud service 1600 that can be used in a data processing system that can be associated with a bed system, including those described above with respect to FIGS. 1-3. In this example, the environment cloud service 1600 is configured to record data related to users' home environment.

The environment cloud service 1600 is shown with a network interface 1602, a communication manager 1604, server hardware 1606, and server system software 1608. In addition, the environment cloud service 1600 is shown with a user identification module 1610, an environmental sensor module 1612, and an environmental factors module 1614.

The environmental sensors module 1612 can include a listing of sensors that users' in the user identification module 1610 have installed in their bed. These sensors include any sensors that can detect environmental variables—light sensors, noise sensors, vibration sensors, thermostats, etc. Additionally, the environmental sensors module 1612 can store historical readings or reports from those sensors.

The environmental factors module 1614 can include reports generated based on data in the environmental sensors module 1612. For example, for a user with a light sensor with data in the environment sensors module 1612, the environmental factors module 1614 can hold a report indicating the frequency and duration of instances of increased lighting when the user is asleep.

In the examples discussed here, each cloud service 410 is shown with some of the same components. In various configurations, these same components can be partially or wholly shared between services, or they can be separate. In some configurations, each service can have separate copies of some or all of the components that are the same or different in some ways. Additionally, these components are only supplied as illustrative examples. In other examples each cloud service can have different number, types, and styles of components that are technically possible.

Figure 17:
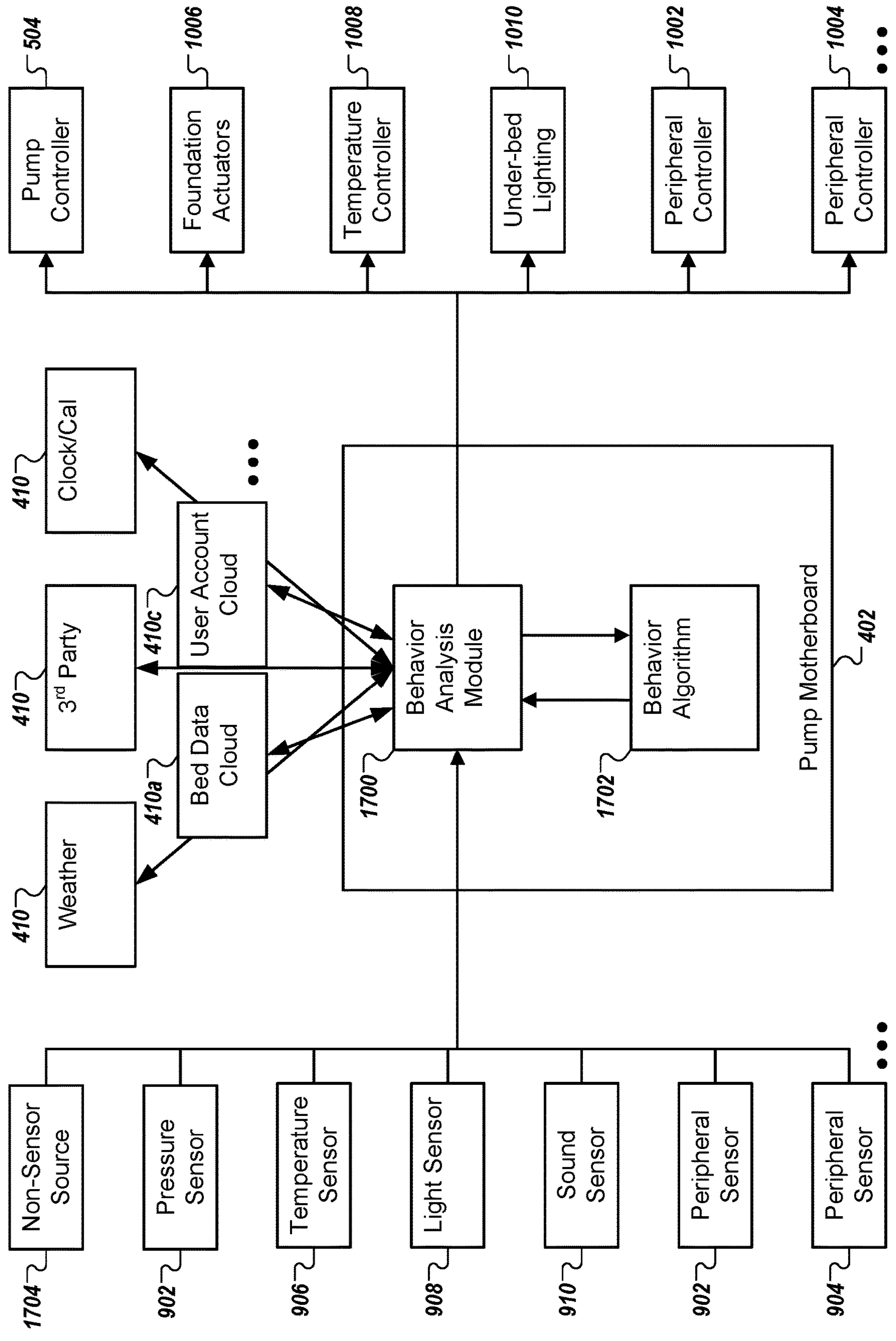
FIG. 17 is a block diagram of an example of using a data processing system that can be associated with a bed to automate peripherals around the bed.

FIG. 17 is a block diagram of an example of using a data processing system that can be associated with a bed (such as a bed of the bed systems described herein) to automate peripherals around the bed. Shown here is a behavior analysis module 1700 that runs on the pump motherboard 402. For example, the behavior analysis module 1700 can be one or more software components stored on the computer memory 512 and executed by the processor 502. In general, the behavior analysis module 1700 can collect data from a wide variety of sources (e.g., sensors, non-sensor local sources, cloud data services) and use a behavioral algorithm 1702 to generate one or more actions to be taken (e.g., commands to send to peripheral controllers, data to send to cloud services). This can be useful, for example, in tracking user behavior and automating devices in communication with the user's bed.

The behavior analysis module 1700 can collect data from any technologically appropriate source, for example, to gather data about features of a bed, the bed's environment, and/or the bed's users. Some such sources include any of the sensors of the sensor array 406. For example, this data can provide the behavior analysis module 1700 with information about the current state of the environment around the bed. For example, the behavior analysis module 1700 can access readings from the pressure sensor 902 to determine the pressure of an air chamber in the bed. From this reading, and potentially other data, user presence in the bed can be determined. In another example, the behavior analysis module can access a light sensor 908 to detect the amount of light in the bed's environment.

Similarly, the behavior analysis module 1700 can access data from cloud services. For example, the behavior analysis module 1700 can access the bed cloud service 410*a* to access historical sensor data 1212 and/or advanced sleep data 1214. Other cloud services 410, including those not previously described can be accessed by the behavior analysis module 1700. For example, the behavior analysis module 1700 can access a weather reporting service, a 3$^{rd}$ party data provider (e.g., traffic and news data, emergency broadcast data, user travel data), and/or a clock and calendar service.

Similarly, the behavior analysis module 1700 can access data from non-sensor sources 1704. For example, the behavior analysis module 1700 can access a local clock and calendar service (e.g., a component of the motherboard 402 or of the processor 502).

The behavior analysis module 1700 can aggregate and prepare this data for use by one or more behavioral algorithms 1702. The behavioral algorithms 1702 can be used to learn a user's behavior and/or to perform some action based on the state of the accessed data and/or the predicted user behavior. For example, the behavior algorithm 1702 can use available data (e.g., pressure sensor, non-sensor data, clock and calendar data) to create a model of when a user goes to bed every night. Later, the same or a different behavioral algorithm 1702 can be used to determine if an increase in air chamber pressure is likely to indicate a user going to bed and, if so, send some data to a third-party cloud service 410 and/or engage a peripheral controller 1002.

In the example shown, the behavioral analysis module 1700 and the behavioral algorithm 1702 are shown as components of the motherboard 402. However, other configurations are possible. For example, the same or a similar behavioral analysis module and/or behavior algorithm can be run in one or more cloud services, and the resulting output can be sent to the motherboard 402, a controller in the controller array 408, or to any other technologically appropriate recipient.

Figure 18:
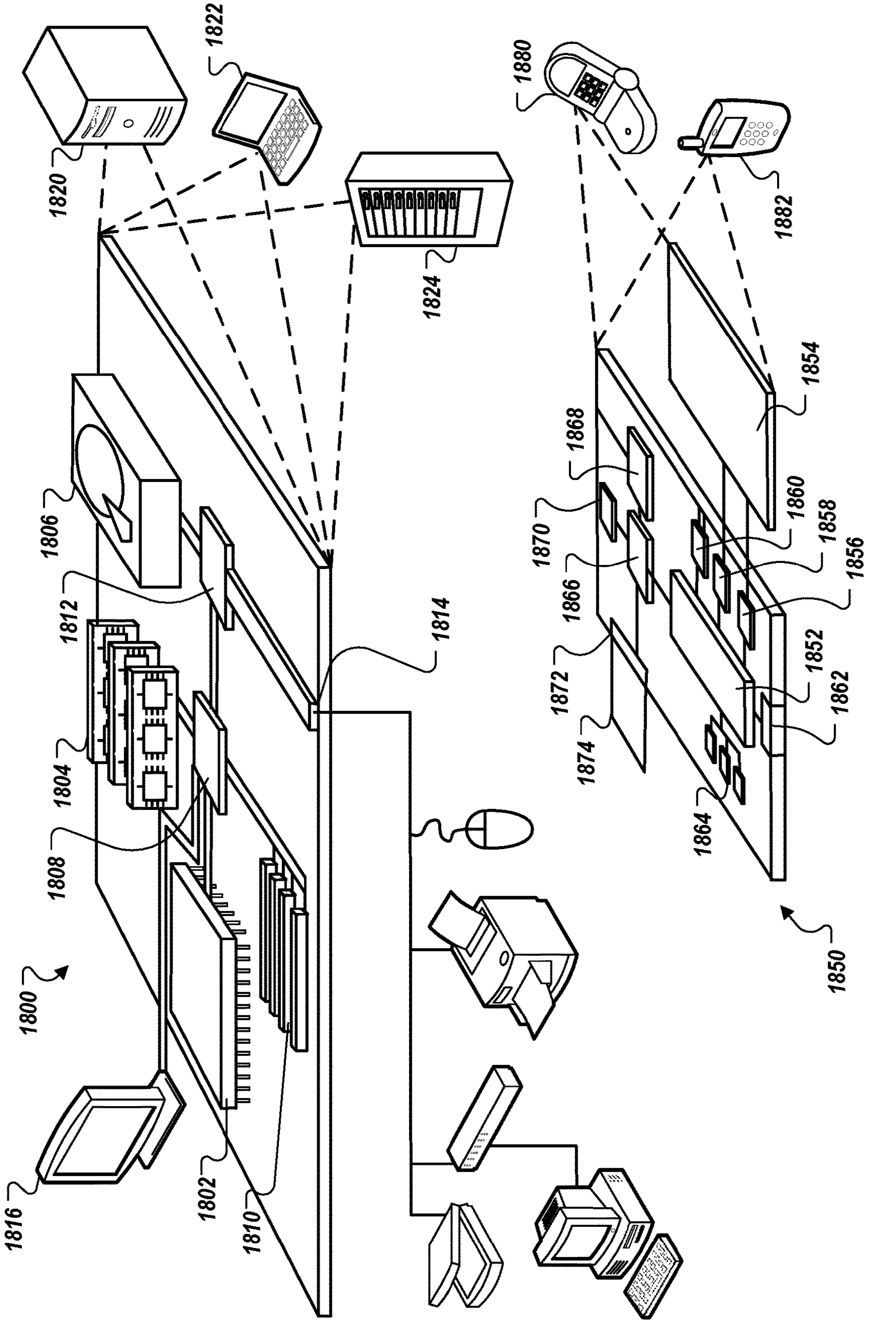
FIG. 18 is a schematic diagram that shows an example of a computing device and a mobile computing device.

FIG. 18 shows an example of a computing device 1800 and an example of a mobile computing device that can be used to implement the techniques described here. The computing device 1800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and can be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1804 stores information within the computing device 1800. In some implementations, the memory 1804 is a volatile memory unit or units. In some implementations, the memory 1804 is a non-volatile memory unit or units. The memory 1804 can also be another form of computer-readable medium, such as a magnetic or optical disk.

The storage device 1806 is capable of providing mass storage for the computing device 1800. In some implementations, the storage device 1806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1804, the storage device 1806, or memory on the processor 1802.

The high-speed interface 1808 manages bandwidth-intensive operations for the computing device 1800, while the low-speed interface 1812 manages lower bandwidth-intensive operations. Such allocation of functions is exemplary only. In some implementations, the high-speed interface 1808 is coupled to the memory 1804, the display 1816 (e.g., through a graphics processor or accelerator), and to the high-speed expansion ports 1810, which can accept various expansion cards (not shown). In the implementation, the low-speed interface 1812 is coupled to the storage device 1806 and the low-speed expansion port 1814. The low-speed expansion port 1814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1800 can be implemented in a number of different forms, as shown in the figure. For example, it can be implemented as a standard server 1820, or multiple times in a group of such servers. In addition, it can be implemented in a personal computer such as a laptop computer 1822. It can also be implemented as part of a rack server system 1824. Alternatively, components from the computing device 1800 can be combined with other components in a mobile device (not shown), such as a mobile computing device 1850. Each of such devices can contain one or more of the computing device 1800 and the mobile computing device 1850, and an entire system can be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 can also be provided with a storage device, such as a micro-drive or other device, to provide additional storage. Each of the processor 1852, the memory 1864, the display 1854, the communication interface 1866, and the transceiver 1868, are interconnected using various buses, and several of the components can be mounted on a common motherboard or in other manners as appropriate.

The processor 1852 can execute instructions within the mobile computing device 1850, including instructions stored in the memory 1864. The processor 1852 can be implemented as a chip set of chips that include separate and multiple analog and digital processors. The processor 1852 can provide, for example, for coordination of the other components of the mobile computing device 1850, such as control of user interfaces, applications run by the mobile computing device 1850, and wireless communication by the mobile computing device 1850.

The processor 1852 can communicate with a user through a control interface 1858 and a display interface 1856 coupled to the display 1854. The display 1854 can be, for example, a TFT (Thin-Film-Transistor Liquid Crystal Display) display or an OLED (Organic Light Emitting Diode) display, or other appropriate display technology. The display interface 1856 can comprise appropriate circuitry for driving the display 1854 to present graphical and other information to a user. The control interface 1858 can receive commands from a user and convert them for submission to the processor 1852. In addition, an external interface 1862 can provide communication with the processor 1852, so as to enable near area communication of the mobile computing device 1850 with other devices. The external interface 1862 can provide, for example, for wired communication in some implementations, or for wireless communication in other implementations, and multiple interfaces can also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 can also be provided and connected to the mobile computing device 1850 through an expansion interface 1872, which can include, for example, a SIMM (Single In Line Memory Module) card interface. The expansion memory 1874 can provide extra storage space for the mobile computing device 1850, or can also store applications or other information for the mobile computing device 1850. Specifically, the expansion memory 1874 can include instructions to carry out or supplement the processes described above, and can include secure information also. Thus, for example, the expansion memory 1874 can be provide as a security module for the mobile computing device 1850, and can be programmed with instructions that permit secure use of the mobile computing device 1850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1864, the expansion memory 1874, or memory on the processor 1852. In some implementations, the computer program product can be received in a propagated signal, for example, over the transceiver 1868 or the external interface 1862.

The mobile computing device 1850 can communicate wirelessly through the communication interface 1866, which can include digital signal processing circuitry where necessary. The communication interface 1866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1868 using a radio-frequency. In addition, short-range communication can occur, such as using a Bluetooth, WiFi, or other such transceiver (not shown). In addition, a GPS (Global Positioning System) receiver module 1870 can provide additional navigation- and location-related wireless data to the mobile computing device 1850, which can be used as appropriate by applications running on the mobile computing device 1850.

The mobile computing device 1850 can also communicate audibly using an audio codec 1860, which can receive spoken information from a user and convert it to usable digital information. The audio codec 1860 can likewise generate audible sound for a user, such as through a speaker, e.g., in a handset of the mobile computing device 1850. Such sound can include sound from voice telephone calls, can include recorded sound (e.g., voice messages, music files, etc.) and can also include sound generated by applications operating on the mobile computing device 1850.

The mobile computing device 1850 can be implemented in a number of different forms, as shown in the figure. For example, it can be implemented as a cellular telephone 1880. It can also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 19:
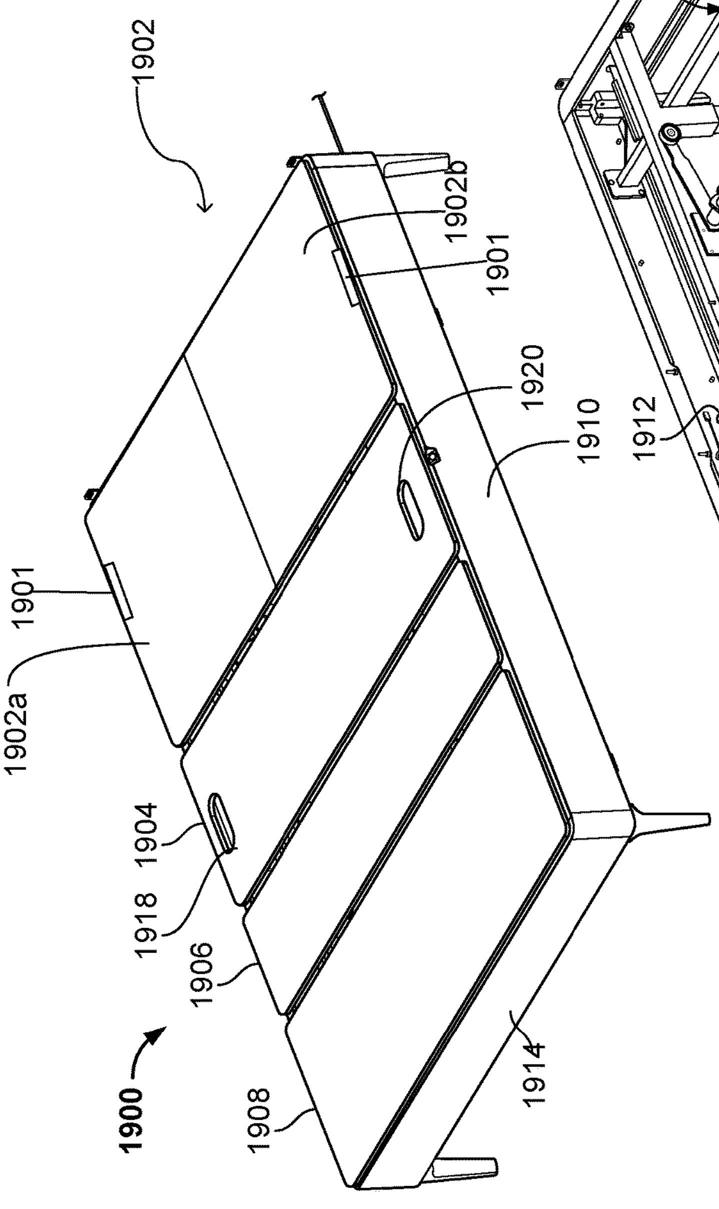
FIG. 19 is a perspective view of an implementation of a foundation.

FIG. 19 is a perspective view of an example foundation 1900. As illustrated in FIG. 19, the foundation 1900 can include one or more deck panels 1902, 1904, 1906, 1908, side rails 1910 and 1912 (the side rail 1912 is not shown in FIG. 19), a foot rail 1914, and a head rail 1916 (not shown in FIG. 19). In some embodiments, the foundation 1900 can be an articulating foundation, such that one or more of the deck panels 1902, 1904, 1906, and 1908 are raised and lowered in response to actuating motors. For example, the deck panel 1902 can be a head deck panel for raising and lowering a head of a mattress. For double occupancy beds, the one or more deck panels can be split for individual sides (left and right) of the bed. For example, the head deck panel 1902 can include a left head deck panel 1902*a* and a right head deck panel 1902*b* that can each be separately articulable for raising and lowering a portion of a mattress supporting a user resting on the raised portion of the mattress on that side of the foundation 1900. The head deck panels 1902*a* and 1902*b* can each include one or more sensors 1901 configured to detect a sound indicative of a snore. One or more of the sensors 1901 can be positioned along an outer edge parallel to the side rails 1910, 1912, or both. In some embodiments, there is a single sensor 1901 along an edge of each of the left and right head deck panels 1902*a* and 1902*b*. In other embodiments, more or fewer sensors 1901 can be used as suitable for the application. The sensor 1901 can be near a head of the foundation 1900, such as within two feet of an edge of the panel 1902 that is parallel to the head rail 1916. Each of two or more sensors 1901 can be used to determine where the snore is coming from, and then adjust only the side of the user who is snoring without bothering the other user. Because the sensors 1901 are on the head panels 1902*a* and 1902*b*, the sensors 1901 are positioned close to the heads of the users so as to detect snore sounds coming from the mouths and noses of the users. In some embodiments, either the left head panel 1902*a*, the right head panel 1902*b*, or both head panels can have an angle adjusted from horizontal when a snore is detected. For example, in some embodiments, a articulation mechanism 1924 (not shown in FIG. 19) is configured to adjust either the panel 1902*a* or 1902*b* to an elevation angle greater than zero. For example, the panel 1902 can be adjusted between zero and seven degrees from the rest of the foundation 1900 (within actuator accuracy specifications) when being adjusted to reduce snoring. In other embodiments, the panel 1902 can be raised to another angle suitable for the application.

Alternatively or in addition, in some embodiments, a mattress firmness can be adjusted in response to the detected snore. In still other embodiments, other functions can be performed in response to sensing snore via the sensors 1901.

The deck panel 1904 can be a back or hip deck panel that remains substantially stationary during actuation. Also, the sensors 1901 raise along with the user, so in the event that the user is sleeping in an elevated position, the sensors will still be located relatively close to the users' mouths when detecting the snores. This increases accuracy and reliability as compared to sensors located elsewhere.

The deck panel 1906 can be a thigh deck panel for raising a thigh section of the mattress at an angle. The deck panel 1908 can be a foot deck panel for raising and lowering a foot portion of the mattress. In some embodiments, the foundation 1900 can be a non-articulating foundation, such that the deck panels 1902, 1904, 1906, and 1908 are not raised and lowered in response to actuating motors.

The deck panels 1902, 1904, 1906, and 1908 can be removably connected to the foundation 1900 for selectively covering and exposing interior components of the foundation 1900. In embodiments where the foundation 1900 is an articulating foundation, the deck panels 1902, 1904, 1906, and 1908 can be connected to an articulation mechanism (not shown in FIG. 19) for articulating one or more of the deck panels 1902, 1904, 1906, and 1908.

In the illustrated embodiment, the deck panel 1904 defines a pair of passages 1918 and 1920 which can accommodate connections between components below and above the deck panels 1902, 1904, 1906, and 1908. For example, one or more hoses (not shown in FIG. 19) can extend from a component, such as a pump, positioned below the deck panels 1902, 1904, 1906, and 1908 to a portion of a mattress positioned above the deck panels 1902, 1904, 1906, and 1908, such as one or more inflatable mattress air chambers as described above. The passages 1918 and 1920 can extend through a non-articulating deck panel 1904 so as to help conceal hoses extending there through, even when one or more of the deck panels 1902, 1906, and 1908 are articulated up.

FIG. 20A-20B show a side and top view, respectively, of an example sensor 1901 that can be used with aspects of this disclosure. The sensor 1901 can be slightly thicker than the deck panel 1902 (FIG. 19) and include tapered edges 2002 to reduce the likelihood of snagging of any fabric or other material used to surround and/or hide the sensor 1901. The tapered edges also help reduce discontinuities in the deck surface that can contribute to discomfort of a sleeper or damage to other bed components.

The sensor 1901 includes an acoustic sensor 2004 contained within a housing 2006. In some embodiments, the acoustic sensor 2004 can include a micro-electro-mechanical (MEMs) type acoustic sensor. In other embodiments, the acoustic sensor 2004 can include a ribbon type acoustic sensor, a piezoelectric type acoustic sensor, or any other type of acoustic sensor. In some embodiments, the acoustic sensor 2004 can be a consumer grade microphone that is modified to protect the privacy of users. For example, a consumer grade microphone can be modified to have a to have a limited bandwidth (such as from 8 KHz to 800 KHz). Such a modified microphone can be suitable for detecting snore sounds without being suitable for detecting a full range of audible speech.

In some embodiments, the sensor 1901 can be waterproofed. Such waterproofing can be accomplished with a sealed housing 2006 and a gasket 2008 around a penetration for the acoustic sensor 2004. A controller, such as the central controller that contains the control circuitry 334 (not shown in FIGS. 20A-20B), is coupled to the sensor. The controller is configured to determine a presence of a snore based upon a signal received by the acoustic sensor 2004. In some embodiments, multiple sensors 1901 can be used. For example, one sensor 1901 on deck panel 1902*a* and another sensor 1901 on deck panel 1902*b*. In such embodiments, the central controller can determine a position of a snoring person based on the data received from the multiple sensors 1901. That is, the central controller can determine if a snoring occupant is on a first half (e.g. left side) or a second half (e.g. right side) of the bed. Once a presence and a location of the snoring occupant are determined, parameters of the bed can be adjusted to mitigate or reduce the snore. For example, the articulation mechanism 1924, changes an elevation angle of the head deck panel 1902 in response to a signal from the controller. In some embodiments, a mattress firmness can be adjusted in response to the detected snore.

Cabling 2010 couples the sensor 1901 to the central controller. In some embodiments, the cabling 2010 attaches to an upper side of the foundation. That is, cabling runs along a surface of the head deck that is configured to be adjacent to a mattress. The cabling 2010 is routed as to allow movement of the head deck panel 1902 (as shown in FIG. 19). While wired embodiments are described within this document, it should be recognized that wireless systems can be used in place of wired components without deviating from the subject matter described herein.

Figure 20C:
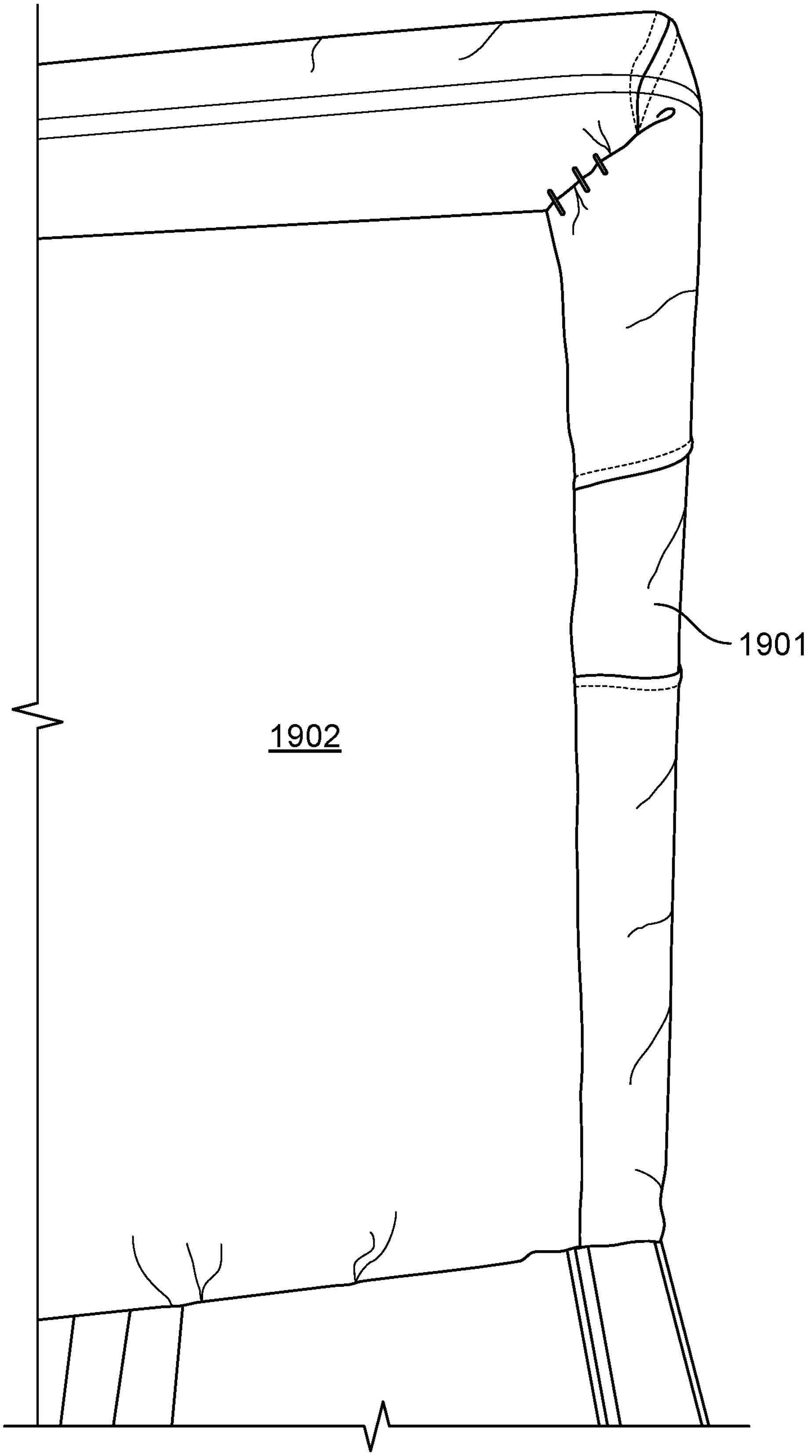
FIGS. 20C-20E are perspective views of an example snore sensor installed on an example deck panel.
Figure 20D:
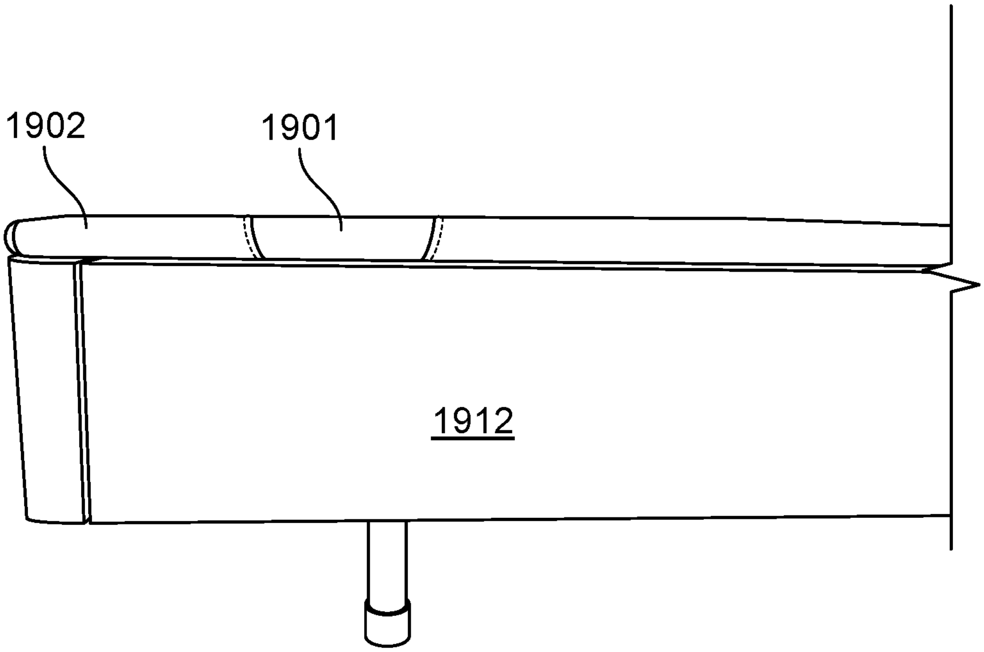
Figure 20E:
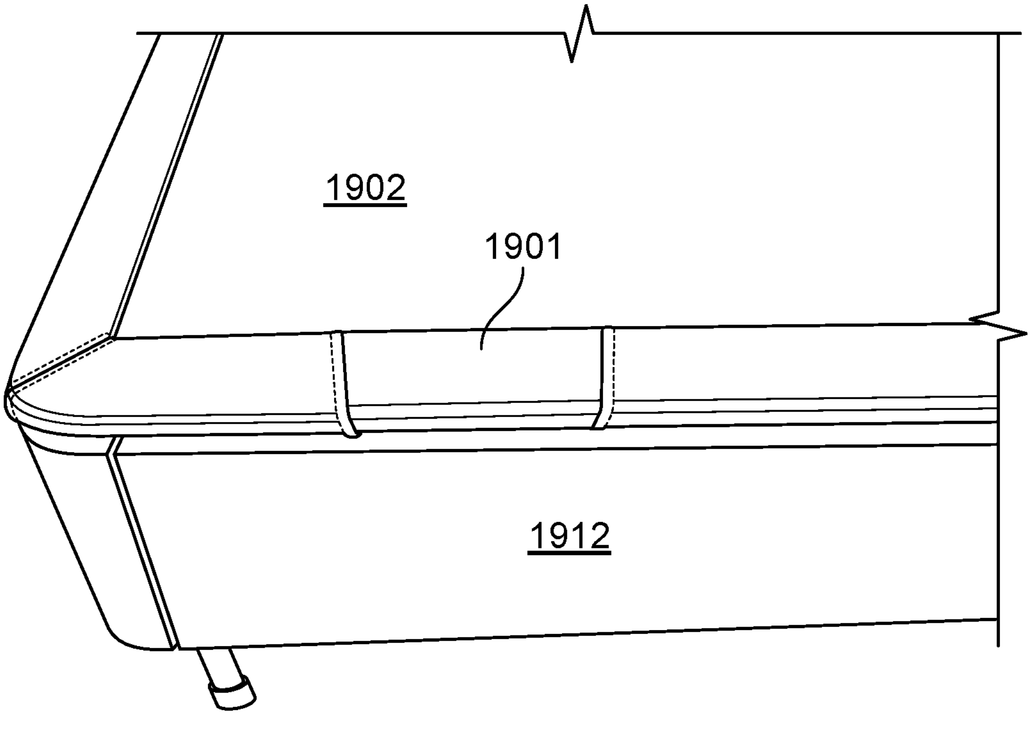

FIG. 20C is a view of a bottom of the head deck panel 1902 with one embodiment of the sensor 1901. FIG. 20D is a side view of the foundation 1900 showing the head deck panel 1902 and the sensor 1901. FIG. 20E is a perspective view of the foundation 1900 showing the head deck panel 1902 and the sensor 1901. As illustrated, the sensor 1901 is positioned along an outer edge of the panel 1902 parallel to the side rail 1912. In some embodiments, the sensor 1901 can be positioned along a side edge of the panel 1902 within two feet from a head edge of the panel 1902 (aka within two feet of an edge of the panel 1902 that is parallel and substantially flush with the head rail 1916 (not shown in FIGS. 20C-20D)). In some embodiments, the sensor 1901 can be positioned along the side edge of the panel 1902 between six and twelve inches from the head edge of the panel 1902. In some embodiments, the sensor 1901 can be positioned along the side edge of the panel 1902 between eight and ten inches from the head edge of the panel 1902.

Positioning the sensor 1901 along the side edge at a suitable location can improve operation of the system for a number of reasons. For example, such a location can avoid or reduce the risk of being obstructed by furniture and bedding, allowing for a more consistent detection of snore. Additionally, such a location can be near to a head of the sleeper, easing the detection of snores. For example, positioning the sensor 1901 on an edge of the panel 1902 allows for the sensor 1901 to be positioned below a mattress and any fitted sheets covering the mattress yet above or near the top of a bed frame surrounding at least part of the foundation 1900. Additionally, positioning the sensor 1901 at a location near a head of the foundation 1900 can avoid sheets and comforters that cover foot and middle portions of the bed, but that expose a portion of the bed and foundation 1900 at the head of the foundation 1900. Moreover, positioning the sensor 1901 near but at least partially spaced away from a head edge of the deck panel 1902 can allow for the sensor 1901 to be positioned closer to the user's nose and mouth to detect snores, but not so far from the head edge to be covered by sheets and comforters in operation. A suitable positioning of the sensor 1901 can achieve one, more, or all of these benefits in some embodiments.

In some embodiments, a sensor 1901 can be installed on a second side of the bed adjacent and parallel to the side rail 1910. In some embodiments, the deck panel 1902 can comprise two separate deck sections, such as the left deck panel 1902*a* and the right deck panel 1902*b*, that can be adjusted independently of one another. In such embodiments, the second head deck panel, such as deck panel 1902*b*, is configured to have an adjustable angle compared to the foundation structure separate and independent of the position of a first head deck panel 1902*a*. The second sensor 1901 (or set of sensors 1901) is positioned along the outer edge of the second head deck panel 1902*b* and is also coupled to the central controller.

Figure 21:
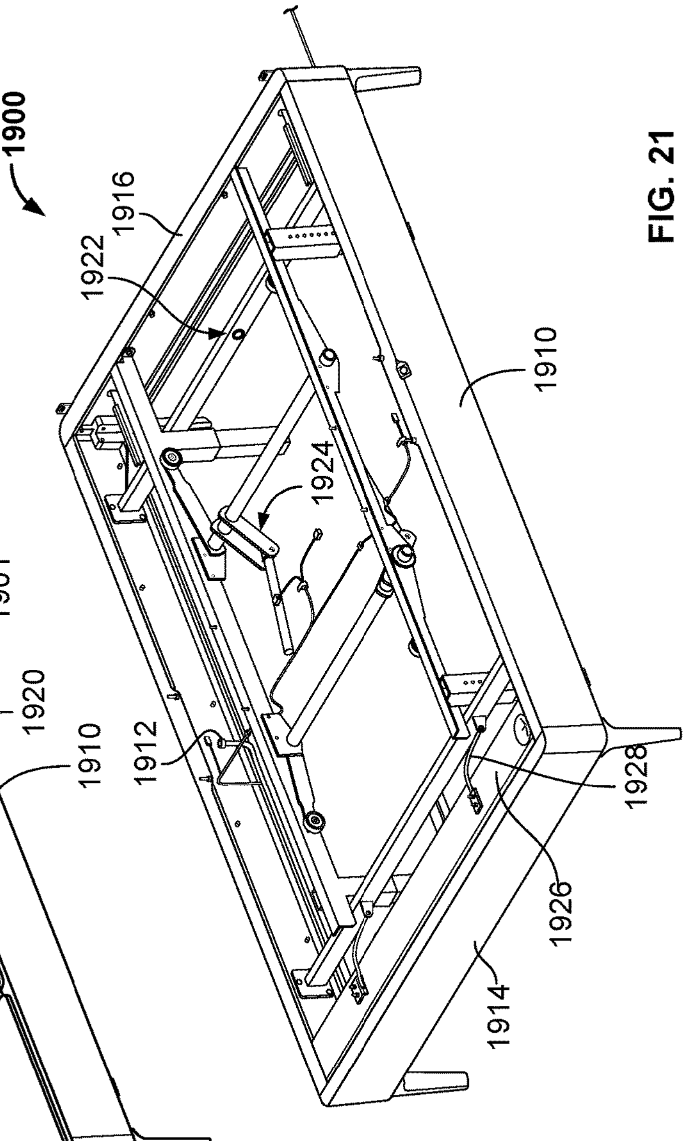
FIG. 21 is a perspective view of the foundation of FIG. 19, with the deck panels removed.

FIG. 21 is a perspective view of the foundation 1900, with the deck panels 1902, 1904, 1906, and 1908 (shown in FIG. 19) removed, exposing interior components of the foundation 1900. With the deck panels 1902, 1904, 1906, and 1908 removed, inner portions of the head rail 1916 and the side rail 1912 can be viewed. FIG. 21 also shows the foundation 1900 having a sub frame 1922 and an articulation mechanism 1924 positioned in the foundation and at least partially concealed by the deck panels 1902, 1904, 1906, and 1908 and the rails 1910, 1912, 1914, and 1916. The sub frame 1922 can provide structural support for other components of the foundation 1900, including the deck panels 1902, 1904, 1906, and 1908, the rails 1910, 1912, 1914, and 1916, and the articulation mechanism 1924. The deck panels 1902, 1904, 1906, and 1908 can be connected to the sub frame 1922 via the articulation mechanism 1924.

The foundation 1900 can include a cover 1926 near a foot of the foundation 1900 for covering components contained within the foundation 1900. The cover 1926 can be hingedly connected to the sub frame 1922 via an opening mechanism 1928. At least some components in the foundation 1900 can be substantially concealed by the cover 1926 and the foot rail 1914 when the cover 1926 is in a closed position, even when the deck panel 1908 is raised to expose the cover 1926.

Figure 22:
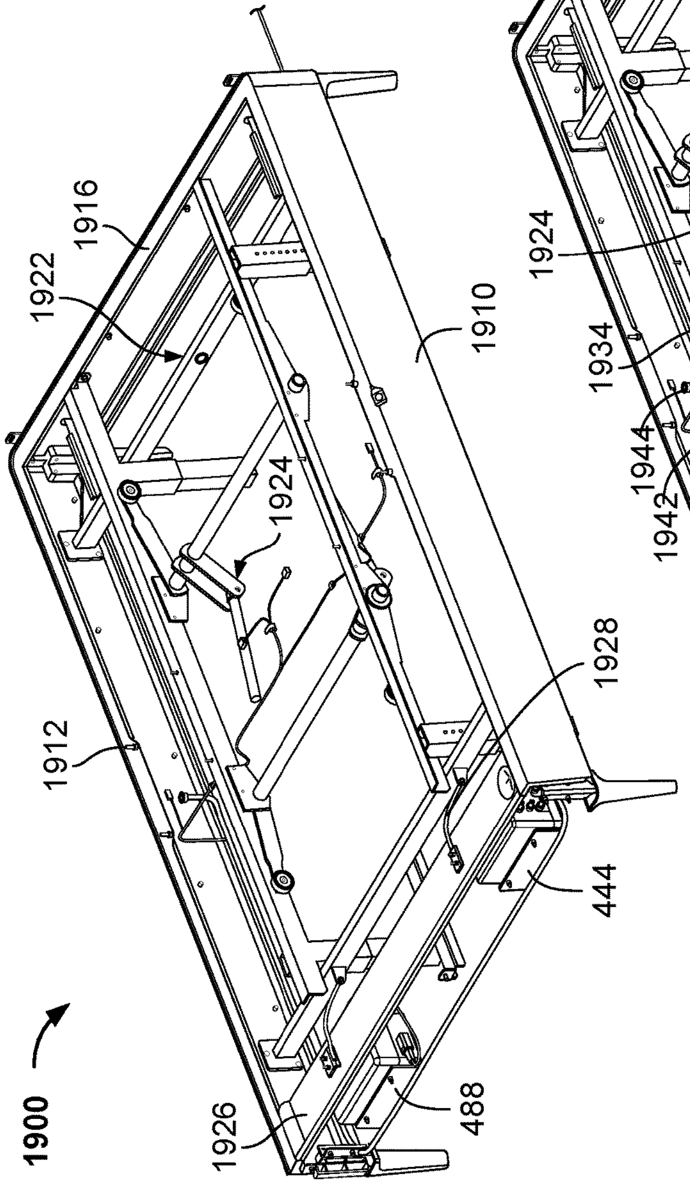
FIG. 22 is a perspective view of the foundation of FIG. 19, also with a foot rail removed.

FIG. 22 is a perspective view of the foundation 1900, with the foot rail 1914 also removed. As shown in FIG. 22, the pump 444 and the adjustable control box 488 can be positioned below the cover 1926. The cover 1926 can be pivoted open to expose and allow access to the pump 444 and the adjustable control box 488 to allow service of components contained within. In some embodiments, the cover 1926 can be omitted. In some embodiments, the pump 444 and/or the adjustable control box 488 can be positioned in other suitable locations other than those illustrated and described herein.

Figure 23:
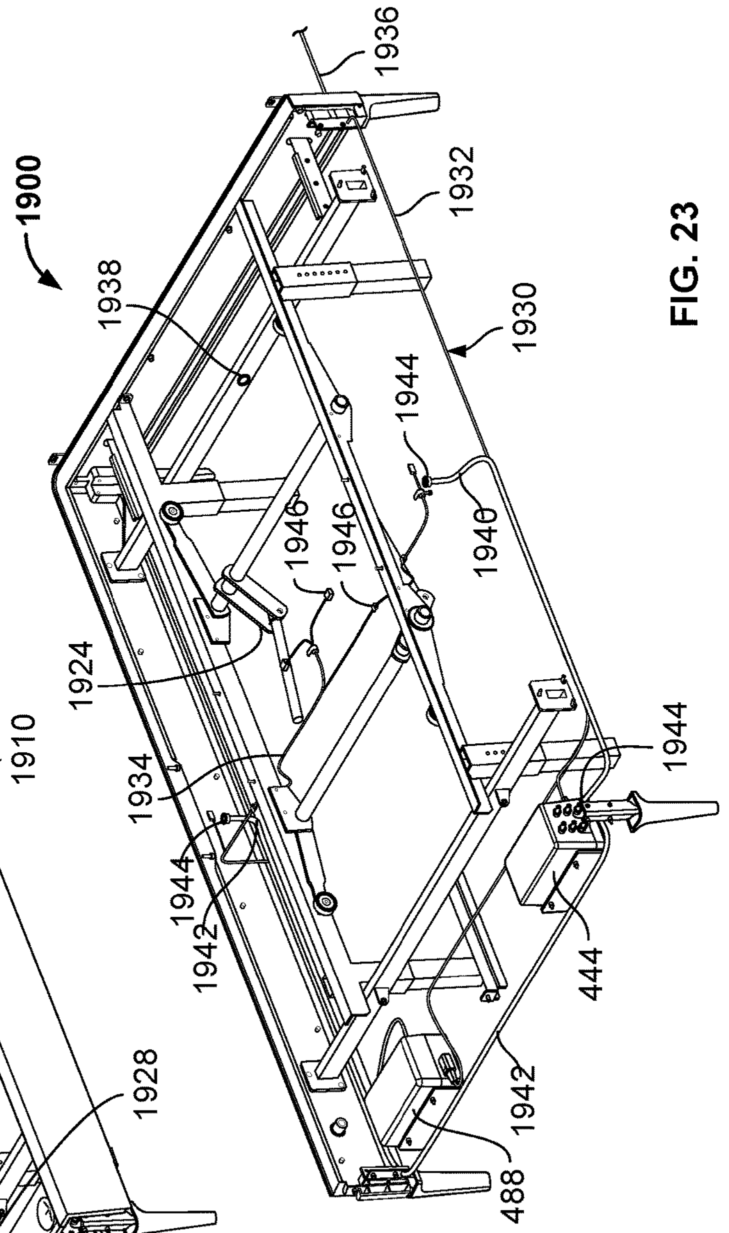
FIG. 23 is a perspective view of the foundation of FIG. 19, also with a cover and side rail removed.

FIG. 23 is a perspective view of the foundation 1900, with the cover 1926 and the side rail 1910 also removed. FIG. 23 shows a central power hub 1930, which can include a high voltage power system 1932 and a low voltage power system 1934. The high voltage power system 1932 can include an AC (alternating current) power cord 1936, which can extend from the foundation 1900 to a power source, such as an electrical wall outlet. The high voltage power system 1932 can supply power to the pump 444 and to the adjustable control box 488. The low voltage power system 1934 can extend from the adjustable control box 488 to one or more additional components of the foundation, such as one or more actuation motors (not shown in FIG. 23) of the articulation mechanism 1924, an under-bed lighting system 1938, and/or other components suitable for being powered by the foundation 1900. In some embodiments, the high voltage power system 1932 can be an AC power system that operates, for example, at 120V, and the low voltage power system 1934 can be a DC (direct current) power system that operates, for example, at one or more lower voltages than the high voltage power system 1932.

FIG. 23 also shows air hoses 1940 and 1942 extending from the pump 444. The air hoses 1940 and 1942 can extend along a perimeter of the foundation 1900 to a central portion of the foundation 1900, and extend up through the passages 1918 and 1920 (shown in FIG. 19) to supply air for controlling pressure in air chambers of a mattress. The air hoses 1940 and 1942 can include connectors 1944 configured for quickly connecting and disconnecting at one or more end.

Cords of the high voltage power system 1932 and the low voltage power system 1934 can also extend along a perimeter of the foundation 1900 and can also include connectors 1946 configured for quickly connecting and disconnecting at one or more end.

In some embodiments, lengths of the hoses 1940, 1942 and/or one or more cords of the central power hub 1930 can extend along and be connected to a structural or aesthetic component of the foundation 1900. For example, the hose 1940 can extend along and be connected to the side rail 1910 (not shown in FIG. 24) so as to be concealed and out of the way when the foundation 1900 is fully assembled. During disassembly, the hose 1940 can be disconnected from the pump 444 via the connector 1944 and can be disconnected from an air chamber of the mattress via the connector 1944 at an opposite end of the hose 1940. In some embodiments, the hose 1940 can remain attached to the side rail 1910, ready to be reconnected to the pump 444 and the air chamber of the mattress when reassembled. In other embodiments, the hose 1940 can be disconnected from the side rail 1910 and then reconnected when reassembled. In a similar manner, the hose 1942 can be connected, either releasably or substantially permanently, to one or both of the foot rail 1914 and the side rail 1912.

Moreover, cords of the central power hub 1930 can also extend along and be connected to one or more rails so as to be concealed and out of the way when the foundation 1900 is fully assembled. For example, a cord of the high voltage power system 1932 can extend along and be connected to the side rail 1910 and extend to the pump 444, while another cord of the high voltage power system 1932 can extend along and be connected to the side rail 1910 and extend to the adjustable control box 488. Both cords of the high voltage power system 1932 can be detachably connected to their respective components via the connectors 1946. The adjustable control box 488 can convert power from the high voltage power system 1932 to lower voltage DC power for use by components on the low voltage power system 1934. One or more cords of the low voltage power system 1934 can extend along one or more rails and/or structural components to the electrical component being powered, such as a lamp of the under-bed lighting system 1938. In some embodiments, the high and low voltage power systems 1932 and 1934 can include more or fewer cords and other components than as illustrated.

Figure 24:
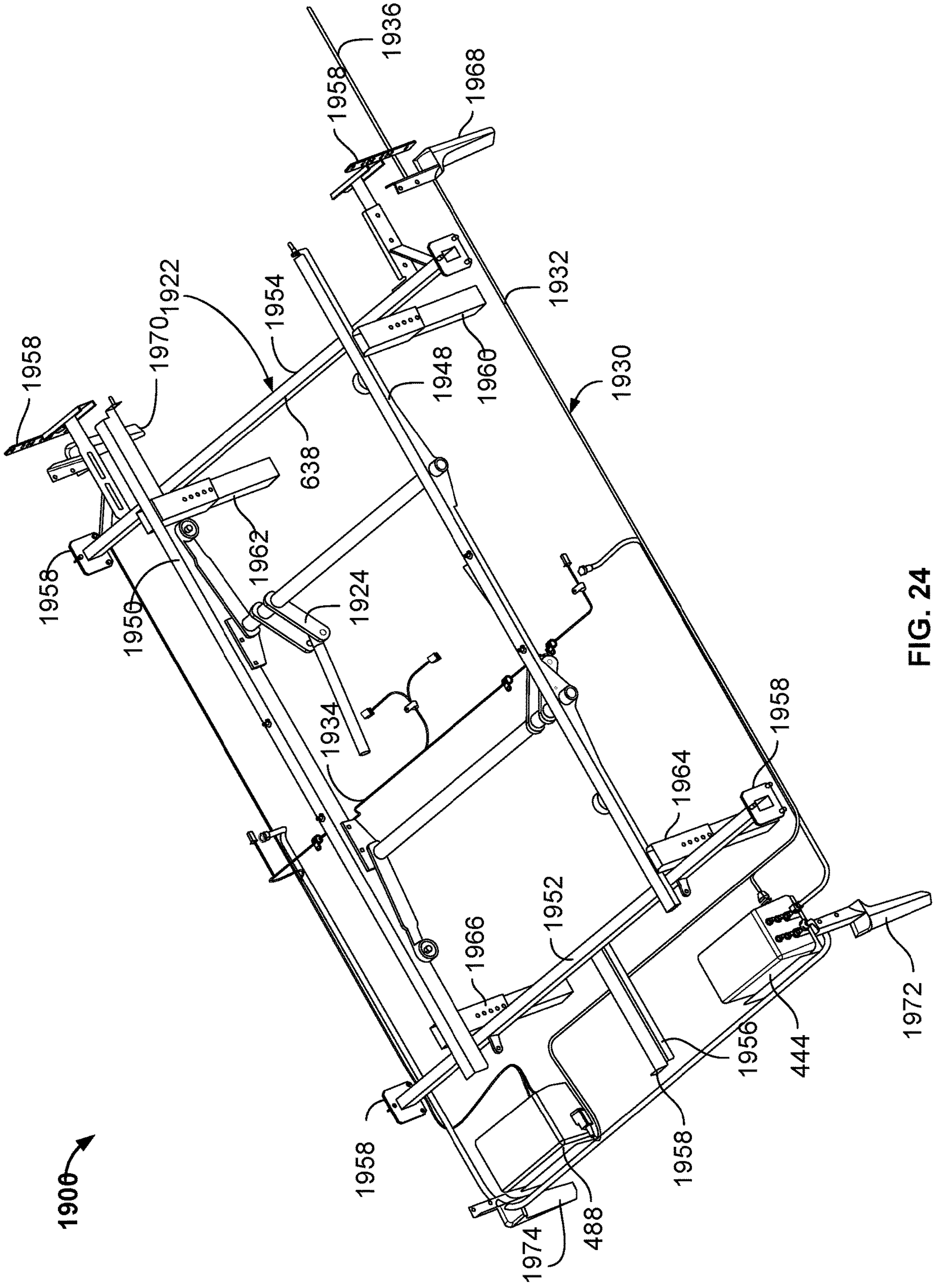
FIG. 24 is a perspective view of the foundation of FIG. 19, also with a head rail and side rail removed.

FIG. 24 is a perspective view of the foundation 1900, with the head rail 1916 and the side rail 1912 also removed. FIG. 24 shows the sub frame 1922 having a plurality of interconnected supports 1948, 1950, 1952, 1954, and 1956. The supports 1948, 1950, 1952, 1954, and 1956 can extend substantially in a horizontal plane. The supports 1948 and 1950 can extend along at least part of a length of the foundation 1900, substantially parallel to the side rails 1910 and 1912 and spaced inward of the side rails 1910 and 1912. The supports 1952 and 1954 can extend along at least part of a width of the foundation 1900, substantially parallel to the head rail 1916 and the foot rail 1914 and spaced inward of the head rail 1916 and the foot rail 1914. The supports 1952 and 1954 can be positioned below and extended across the supports 1948 and 1950 to provide strength and rigidity for the sub frame 1922. The supports 1948 and 1950 can have a substantially flat upper surface configured for supporting the deck panels 1902, 1904, 1906, and 1908 (shown in FIG. 19) when the deck panels 1902, 1904, 1906, and 1908 rest on the supports 1948 and 1950. The support 1956 can extend from the support 1952 in a cantilevered manner toward the foot of the bed. One or more connection brackets 1958 can be connected to one or more of the supports 1948, 1950, 1952, 1954, and 1956 and be configured for allowing removable connection of the rails 1910, 1912, 1914, and 1916 to the supports 1948, 1950, 1952, 1954, and 1956.

Figure 25:
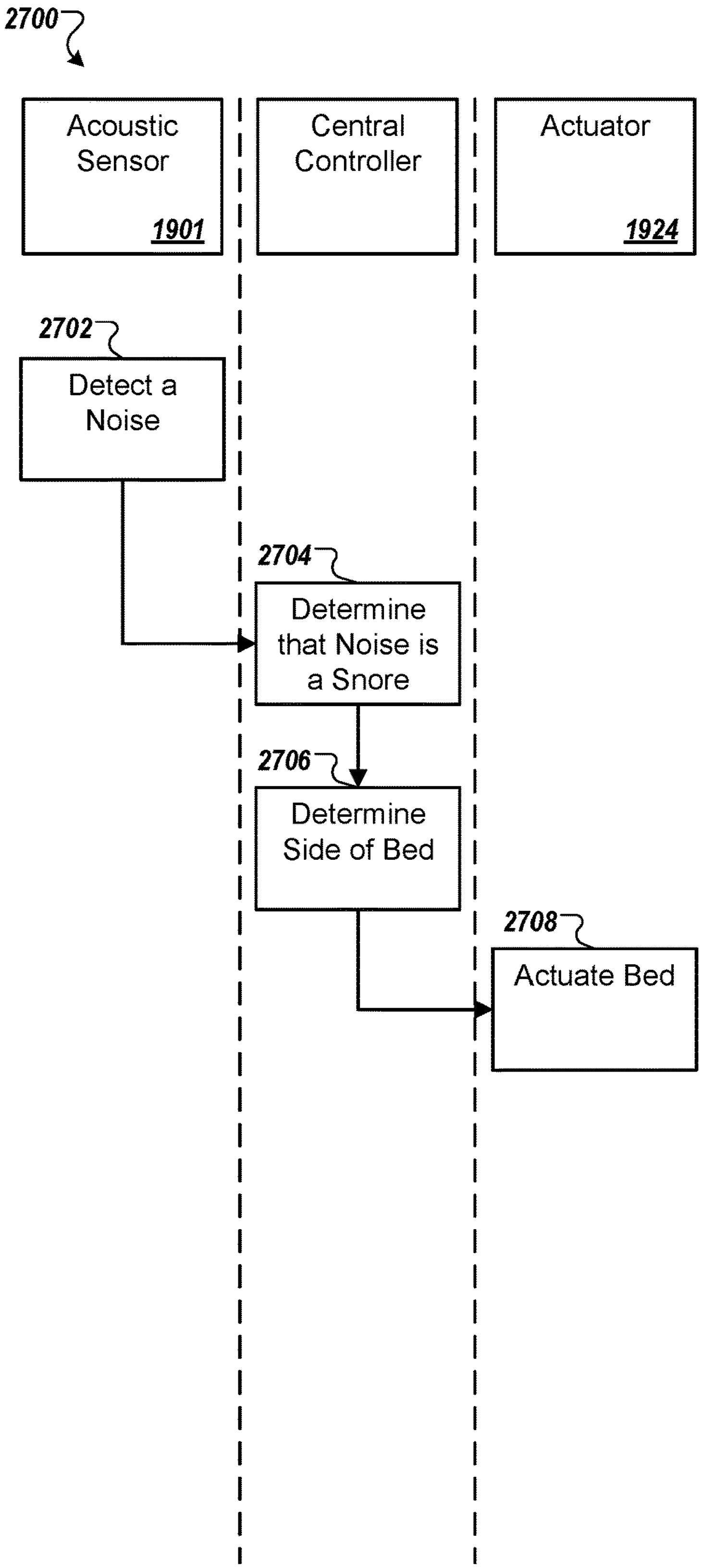
FIG. 25 is a swimlane diagram of an example process for detecting a snore and adjusting the foundation in response to the snore detection.

FIG. 25 is a swimlane diagram of an example process 2700 adjusting the foundation 1900 in response to detecting a snore. For clarity, the process 2700 is being described with reference to components of the data processing system 400. However, other systems may be used to perform the same or a similar process.

The process 2700 can begin, for example, at 2702, when a noise is detected with one or more acoustic sensors 1901 located on an outer edge of a deck panel within two feet of an edge of the deck panel at a head of a bed. At 2704, the noise is determined to be a snore based on a signal from the one or more acoustic sensors by the central controller. As previously stated, the data processing system 400 can act as the controller in this description, but in some implementations, another controller can be used. At 2706, a side of a bed that the snore originated is determined based on the signal from the one or more acoustic sensors 1901. Next, a determined side of the bed is adjusted. In some embodiments, adjusting a determined side of the bed can include, at 2708, adjusting an angle of a head of the determined side of the bed with an actuation mechanism, such as actuator 1924. In some embodiments, when such an actuation is made, the angle is adjusted from horizontal to substantially seven degrees above horizontal. In some embodiments, adjusting the determined side of the bed includes adjusting a mattress firmness of the determined side of the bed.

FIG. 26 is a perspective view of a portion of the foundation 1900 with the sensor 1901 and the deck panel 1902 wrapped in a cover 2650, such as a fabric cover. The cover 2650 can have multiple portions, including a central portion 2652, a perimeter portion 2654, and a sensor portion 2656. The central portion 2652 can be a fabric positioned generally in the center of the deck panel 1902. The sensor portion 2656 can be a fabric positioned generally over a location of the sensor 1901. The perimeter portion 2654 can be positioned around some or all of a perimeter of the deck panel 1902 except for over the sensor 1901, which is covered by the sensor portion. In some embodiments the cover 2650 can have more or fewer portions than as illustrated in FIG. 26. For example, in some embodiments the perimeter portion 2654 and the sensor portion 2652 can be the same material so long as it is suitable for covering the sensor 1901. In other embodiments, the cover can have one or more fabrics (and/or other materials) that is suitable for the application.

In the embodiment shown in FIG. 26, the central portion 2652, the perimeter portion 2654, and the sensor portion 2656 are stitched together along seams 2658. The sensor portion 2656 can be made of a material that is suitable for covering the sensor 1901 yet allowing the sensor 1901 to function appropriately. In applications when the sensor 1901 includes an acoustic sensor, the sensor portion 2656 can be configured to allow for sound to transmit through the sensor portion 2656 to be sensed by the sensor 1901.

In some embodiments, the cover 2650 can be permanently or semi-permanently attached to the deck panel 1902 with no special consideration for allowing access to the sensor 1901 for repair or replacement of the sensor 1901. For example, the cover 2650 can be attached to the deck panel 1902 with staples and/or adhesive.

In some embodiments, some or all of the cover 2650 can be configured to be removed or opened to allow access to the sensor 1901 for repair or replacement of the sensor 1901. For example, the cover 2650 can have one or more flaps that can be opened to allow access to the sensor 1901.

FIGS. 27A-27B show a foundation 2700 and a snore sensor 2701 attached to a deck panel 2702 of the foundation 2700. The foundation 2700 and the snore sensor 2701 can have many similar features as those described above with respect to foundation 1900 and senor 1901, and with some differences.

The deck panel 2702 can be wrapped in a cover 2750, such as a fabric cover. The cover 2750 can have multiple portions, including a central portion 2752, a perimeter portion 2754, and a sensor portion 2756. The sensor portion 2756 can be a flap configured to open to expose the sensor 2701. FIG. 27A shows the sensor portion 2756 covering the sensor 2701. FIG. 27B shows the sensor portion 2756 lifted open to expose the sensor 2701.

Additional components can be covered by the sensor portion 2756 of the cover 2750. For example, a fire resistance panel 2760 can be positioned between the sensor portion 2756 and the sensor 2701. An acoustic panel 2762 can also be positioned under the sensor portion 2756 at a location adjacent the sensor 2701. Accordingly, lifting the sensor portion 2756 can expose the sensor 2701, the fire resistance panel 2760, and the acoustic panel 2762 so that some or all of these components can be repaired or replaced.

In the embodiment shown in FIGS. 27A and 27B, the perimeter portion 2754 can be permanently or semi permanently attached to the deck panel 2702 while the sensor portion 2756 is less permanently attached. For example, the perimeter portion 2754 can be attached to the deck panel 2702 via staples or adhesive while the sensor portion 2756 is attached to the deck panel 2702 at least partially via one or more fasteners 2764 such as snaps, screws, and/or hook-and-loop fasteners (commonly called a VELCRO brand fastener).

As shown in FIG. 27A, the sensor portion 2756 that acts as an openable flap can be relatively small—sized just large enough to cover the sensor 2701. In some embodiments such as shown in FIGS. 27A and 27B, the sensor portion 2756 can be trapezoidal. In other embodiments, the sensor portion 2756 can have another shape suitable for the application.

Figure 28:
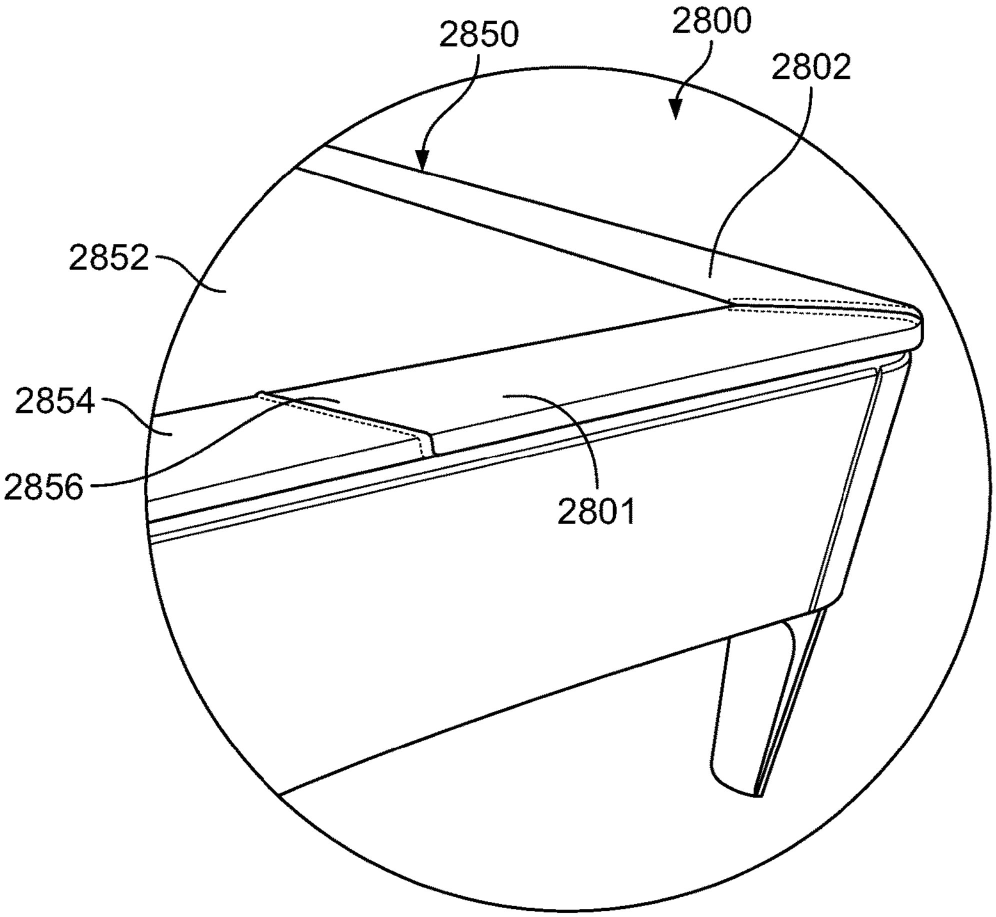
FIG. 28 is a view of another embodiment of a foundation with a snore sensor.

FIG. 28 show a foundation 2800 and a snore sensor 2801 attached to a deck panel 2802 of the foundation 2800. The foundation 2800 and the snore sensor 2801 can have many similar features as those described above with respect to foundation 1900 and senor 1901, and with some differences.

The deck panel 2802 can be wrapped in a cover 2850, such as a fabric cover. The cover 2850 can have multiple portions, including a central portion 2852, a perimeter portion 2854, and a sensor portion 2856.

Figure 29A:
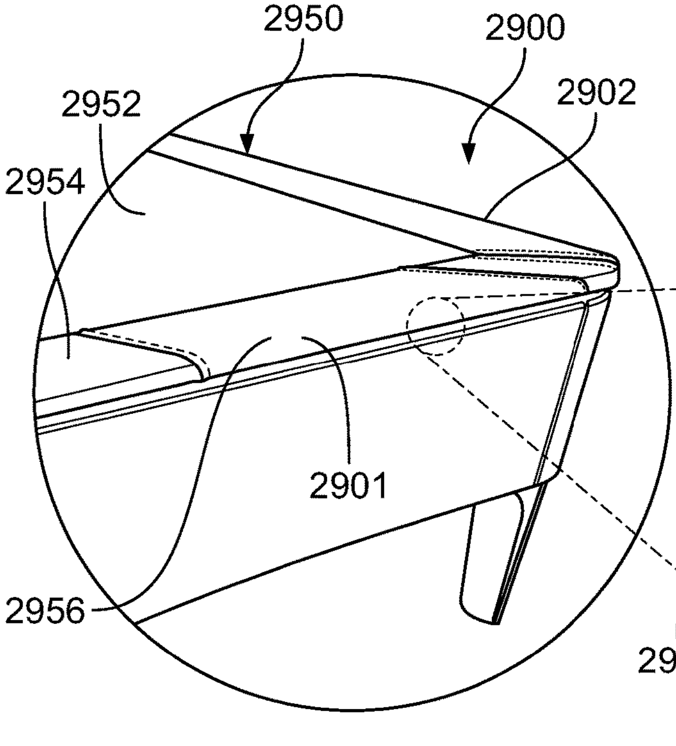
FIGS. 29A-29B are views of another embodiment of a foundation with a snore sensor.
Figure 29B:
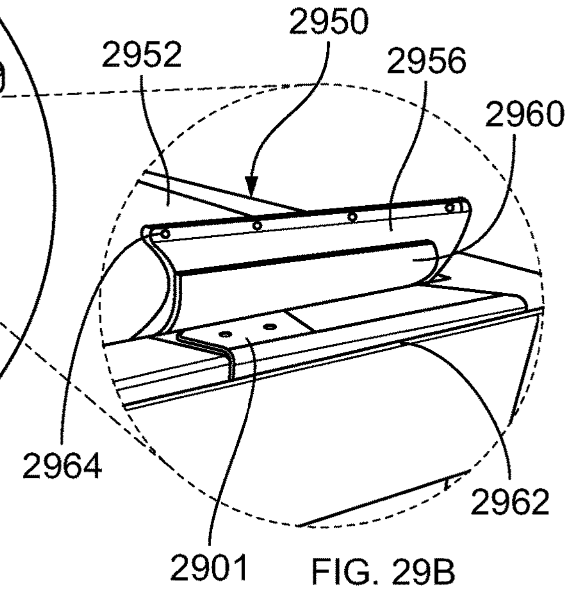

As shown in FIG. 28, the sensor portion 2856 of the cover 2850 can be larger than as shown in FIGS. 27A and 27B. For example, the sensor portion 2856 can extend to a corner of the deck panel 2802 of the foundation 2800 even if the sensor 2801 is spaced away from the corner of the deck panel 2802. For example, as shown in FIGS. 29A-29B, the sensor portion 2956 extends past the sensor 2901 to the head edge. In some embodiments, the sensor portion 2856 can be a flap configured to open to expose the sensor 2801.

FIGS. 29A-29B show a foundation 2900 and a snore sensor 2901 attached to a deck panel 2902 of the foundation 2900. The foundation 2900 and the snore sensor 2901 can have many similar features as those described above with respect to foundation 1900 and senor 1901, and with some differences.

The deck panel 2902 can be wrapped in a cover 2950, such as a fabric cover. The cover 2950 can have multiple portions, including a central portion 2952, a perimeter portion 2954, and a sensor portion 2956. The sensor portion 2956 can be a flap configured to open to expose the sensor 2901.

Additional components can be covered by the sensor portion 2956 of the cover 2950, including a fire resistance panel 2960 and an acoustic panel 2962. Accordingly, lifting the sensor portion 2956 can expose the sensor 2901, the fire resistance panel 2960, and the acoustic panel 2962 so that some or all of these components can be repaired or replaced.

The sensor portion 2956 can be sized substantially larger than the sensor 2901. Accordingly, the sensor portion 2956 can be relatively large (as shown in FIG. 29A) even if the sensor 2901 is relatively small (as shown in FIG. 29B).

Figure 30A:
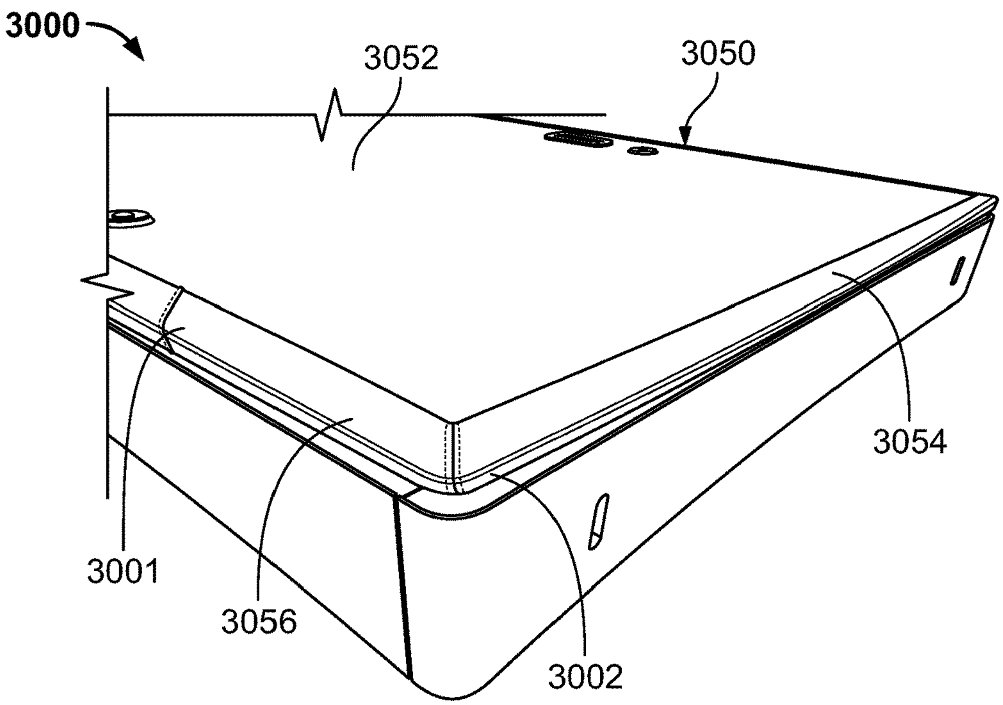
FIGS. 30A-30C are views of another embodiment of a foundation with a snore sensor.
Figure 30B:
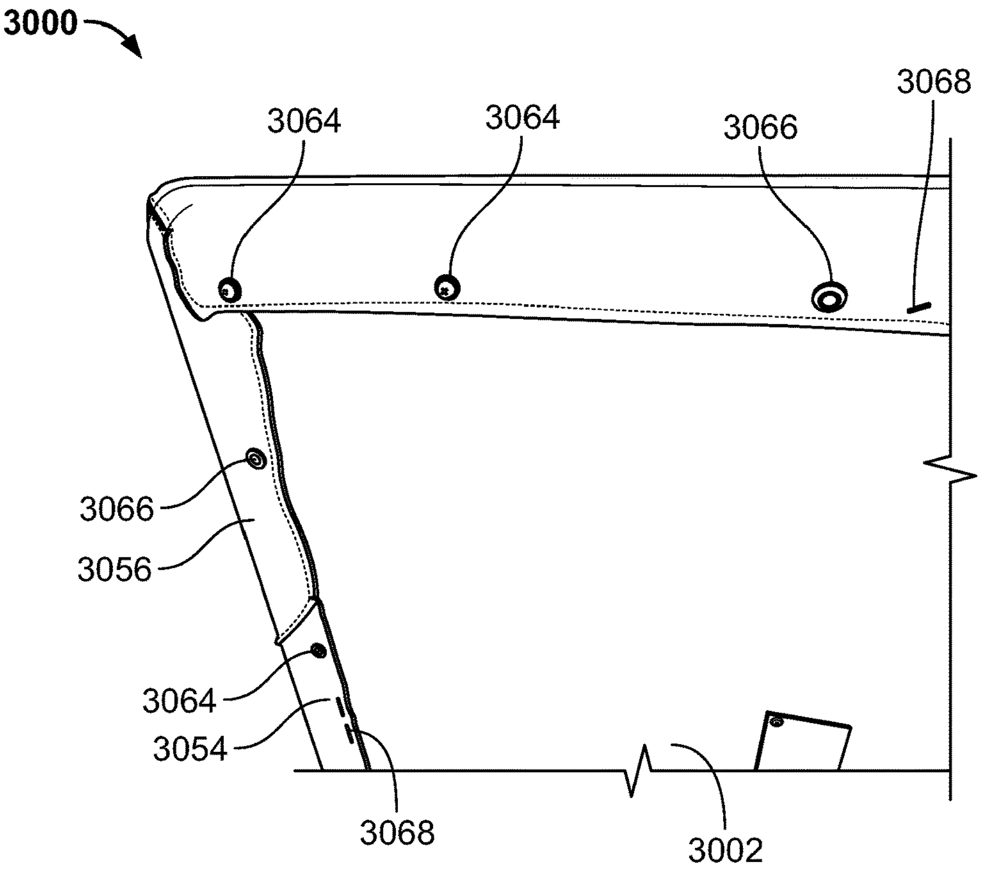
Figure 30C:
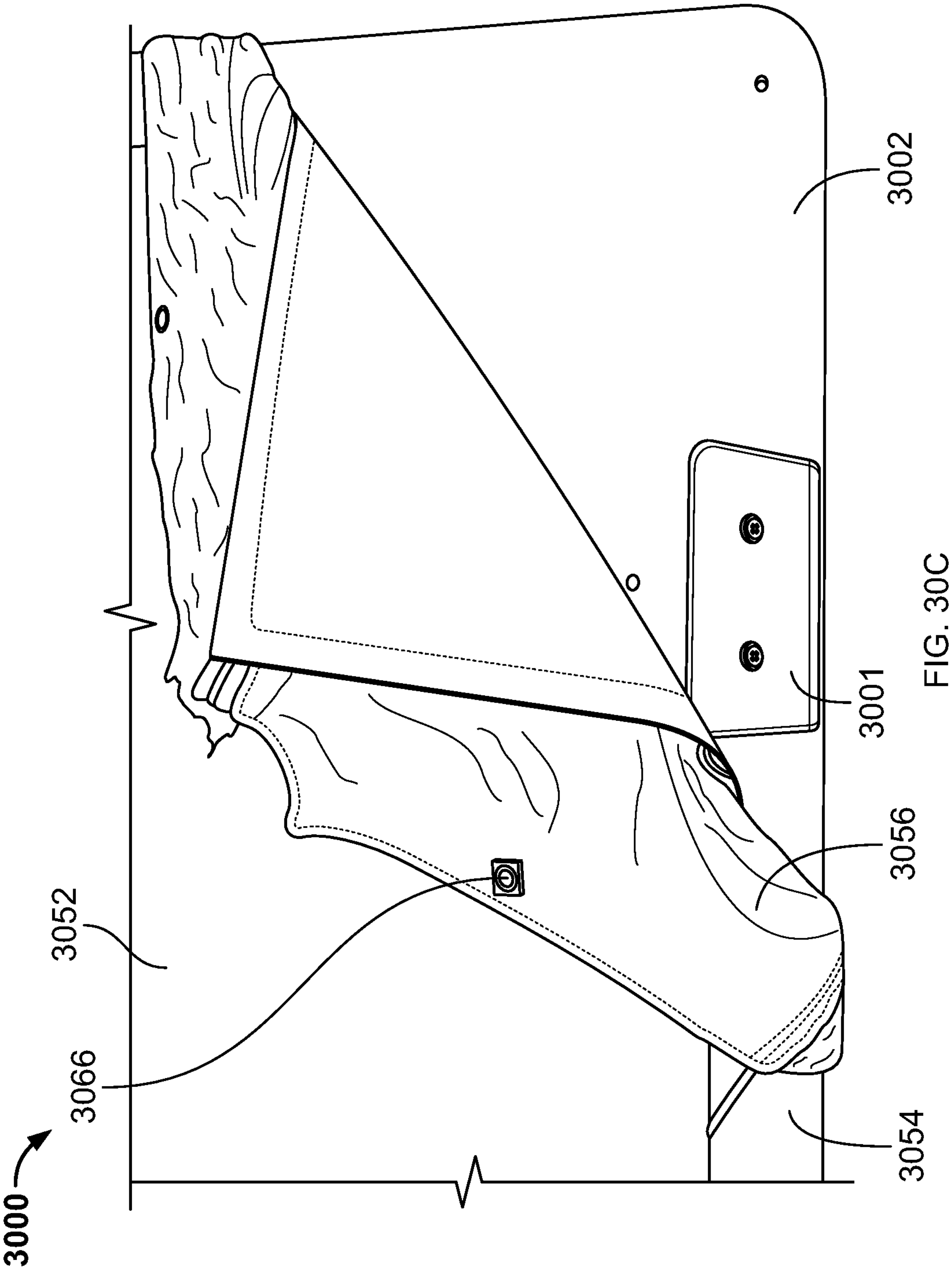

FIGS. 30A-30C show a foundation 3000 and a snore sensor 3001 attached to a deck panel 3002 of the foundation 3000. The foundation 3000 and the snore sensor 3001 can have many similar features as those described above with respect to foundation 1900 and senor 1901, and with some differences.

The deck panel 3002 can be wrapped in a cover 3050, such as a fabric cover. The cover 3050 can have multiple portions, including a central portion 3052, a perimeter portion 3054, and a sensor portion 3056.

The sensor portion 3056 can be part of a flap configured to open to expose the sensor 3001. In the embodiment shown in FIGS. 30A-30C, the central portion 3052, the perimeter portion 3054, and the sensor portion 3056 are all part of a flap that can be lifted to expose and access the sensor 3001. A plurality of fasteners 3064 (such as screws) can be used to removably detach and re-attach a portion of the cover 3050 to the deck panel 3002. The cover 3050 can include grommets 3066 to strengthen attachment locations and the fasteners 3064 can extend through the grommets 3066 to attach the removable portion of the cover 3050 to the deck panel 3002.

Other portions of the cover 3050 can be attached to the deck panel 3002 using a different mechanism, such as staples 3068. In some applications, staples 3068 can be considered more permanent than screws or other fasteners (e.g. fasteners 3064) because screws can be configured for repeated use in attaching and detaching while staples are generally configured for a single use. In addition to or in place of staples 3068, alternative mechanisms can be used to attach the cover 3050 to the deck panel 3002, such as adhesive.

FIG. 30A shows a top perspective view of the foundation 3000 with the cover 3050 attached to the deck panel 3002 of the foundation 3000. FIG. 30B shows a bottom side of the deck panel 3002, with some of the fasteners 3064 removed from the grommets 3066 and the deck panel 3002. As shown in FIGS. 29A-29B and FIG. 30B, an end of the flap is offset from and extends past the acoustic panel 2956 to couple to a bottom surface (shown in FIG. 30B) of a head panel of the foundation structure 3000. FIG. 30C shows a portion of the foundation 3000 with a flap of the cover 3050 opened at a corner of the deck panel 3002 to expose the sensor 3001. With the flap of the cover 3050 opened, the sensor 3001 can be repaired or replaced relatively easily. By using the removable and replaceable fasteners 3064 and grommets 3066, the sensor 3001 can be exposed for replacement without having to remove and replace more permanent fasteners, such as staples and/or adhesive.

As described above and shown in the figures, bed systems can include a number of components integrated and combined together in a compact, user-friendly, and functional manner. Such bed systems can include one or more of an air bed pump system, dual temperature air units, storage compartments, and/or mattress actuators with a foundation, an air mattress, and a dual temperature layer in a manner that can reduce cost of manufacturing and assembly, while creating a product that is more user-friendly and includes features that improve user comfort and sleep quality.

A number of embodiments of the inventions have been described. Nevertheless, it will be understood that various modifications can be made without departing from the spirit and scope of the invention. For example, in some embodiments, the bed need not include adjustable air chambers. Moreover, in some embodiments, various components of the foundation 1900 can be shaped differently than as illustrated. Additionally, different aspects of the different embodiments of foundations, mattresses, and other bed system components described above can be combined with other aspects as suitable for the application. Moreover, some embodiments can detect snoring using audio sensors alone, while other embodiments can detect snoring using audios sensors in conjunction with other sensors, such as air pressure sensors. Accordingly, other embodiments are within the scope of the following claims.

What is claimed is:

1. A bed system comprising:

a foundation structure comprising one or more panels configured to support a mattress, the foundation structure defining a perimeter portion about a center portion;

at least one sensor positioned in the perimeter portion of the one or more panels, the at least one sensor configured to detect a sound indicative of a snore received at the perimeter portion, the at least one sensor comprising an acoustic sensor;

a fabric deck panel cover configured to cover a top surface of the foundation structure and a portion of a side surface of the foundation structure, wherein the fabric deck panel cover comprises:

an acoustic panel positioned along a head edge of a perimeter portion of the fabric deck panel cover, the acoustic panel covering a side portion of the acoustic sensor, wherein the acoustic panel comprises a first fabric different than a second fabric comprising the perimeter portion, the first fabric configured to be suitable for covering the acoustic sensor while still allowing the acoustic sensor to detect the sound indicative of the snore at the side surface of the foundation structure, the sound indicative of the snore originating from a sleeper on the mattress;

a flap that is positioned and configured to be opened to allow for access to the at least one sensor, the flap extending from a center portion of the fabric deck panel cover to the side surface of the foundation structure, the flap comprising a sensor portion positioned along the head edge of the perimeter portion of the fabric deck panel cover; and a fire resistance panel positioned between the flap and the at least one sensor, wherein the fire resistance panel is fixed at one end to the flap at an intersection of the perimeter portion and the center portion and terminates on a top surface of a head panel of the foundation structure on the perimeter portion in contact with the acoustic panel when in a down position; and a controller configured to perform operations comprising:

receiving a signal from the at least one sensor indicative of the snore from the at least one sensor; and determining a position of a snoring person based, at least in part, on the signal indicative of the snore.

2. The bed system of claim 1, wherein the foundation structure comprises the head panel, the head panel defining the head edge of the perimeter portion, and the at least one sensor positioned along the head edge.

3. The bed system of claim 2, and wherein the fabric deck panel cover is configured to cover at least a portion of the head panel and the at least one sensor.

4. The bed system of claim 3, wherein the flap extends from the at least one sensor to a corner of the foundation structure.

5. The bed system of claim 4, wherein the at least one sensor is offset from the corner of the foundation structure.

6. The bed system of claim 1, wherein the position of the snoring person comprises one of a left side of the mattress or a right side of the mattress.

7. The bed system of claim 1, wherein the position of the snoring person comprises one of a flat position or an inclined position.

8. The bed system of claim 1, wherein the controller is further configured to perform operations comprising:

based on the signal from the at least one sensor indicative of the snore, determining whether the snoring person is positioned on a left side or a right side of the mattress; and based on a history of a movement of an actuator, the actuator configured to adjust an elevation of the mattress relative to the foundation structure, determining whether the snoring person is positioned at a flat position or an inclined position.

9. The bed system of claim 8, wherein the actuator is further configured to control the elevation of the head panel of the foundation structure.

10. The bed system of claim 9, wherein the actuator is configured to adjust an elevation angle of the head panel relative to the foundation structure between zero and seven degrees.

11. The bed system of claim 9, wherein the controller is further configured to perform operations comprising controlling the elevation of the head panel only on a side of the mattress on which the snoring person is determined to be positioned.

12. The bed system of claim 9, wherein the actuator is configured to adjust the elevation of a left side of the head panel and a right side of the head panel independently.

13. The bed system of claim 8, wherein the controller is further configured to perform operations comprising, based on determining the position of the snoring person, adjusting a firmness of the mattress.

14. The bed system of claim 13, wherein adjusting the firmness of the mattress comprises adjusting the firmness only on a side of the mattress on which the snoring person is determined to be positioned.

15. The bed system of claim 1, wherein the acoustic sensor having a bandwidth limited detect snore sounds but to not extend over a full range of audible speech.

16. The bed system of claim 1, wherein the acoustic sensor has a bandwidth between 8 KHz to 800 KHz.

17. The bed system of claim 1, further comprising a cable coupling the at least one sensor to the controller, the cable running from the at least one sensor along a portion of the top surface of the foundation structure adjacent to the mattress to reach the controller.

18. The bed system of claim 1, wherein the at least one sensor is positioned along a side edge of a head panel of the foundation structure below the mattress between six and twelve inches from a head edge of the head panel.

19. A bed system comprising:

a foundation structure comprising one or more deck panels configured to support a mattress, the foundation structure defining a perimeter portion about a center portion, the foundation structure defining a top surface;

at least one sensor positioned in the perimeter portion of the one or more deck panels, the at least one sensor configured to detect a sound indicative of a snore received at the perimeter portion, wherein the at least one sensor has a height greater than a height of the one or more deck panels of the foundation structure and tapered edges extending wider than a void within the one or more deck panels in which the at least one sensor is disposed, the tapered edges tapering toward the top surface of the foundation structure;

a fabric deck panel cover configured to cover the top surface of the foundation structure and a portion of a side surface of the foundation structure, wherein the fabric deck panel cover comprises a flap that is positioned and configured to be opened to allow for access to the at least one sensor, the flap extending from the center portion to the side surface of the foundation structure; and a controller configured to perform operations comprising:

receiving a signal from the at least one sensor indicative of the snore from the at least one sensor; and determining a position of a snoring person based, at least in part, on the signal indicative of the snore.

20. The bed system of claim 19, wherein the fabric deck panel cover further comprises an acoustic panel positioned along a head edge of the perimeter portion of the fabric deck panel cover, the acoustic panel covering a side portion of the at least one sensor comprising an acoustic sensor, wherein the acoustic panel comprises a first fabric different than a second fabric comprising the perimeter portion, the first fabric configured to be suitable for covering the acoustic sensor while still allowing the acoustic sensor to detect the sound indicative of the snore at the side surface of the foundation structure, the sound indicative of the snore originating from a sleeper on the mattress.

21. The bed system of claim 20, wherein the fabric deck panel cover further comprises a fire resistance panel positioned between the flap and the at least one sensor.

22. The bed system of claim 20, wherein a fire resistance panel is fixed at one end to the flap at an intersection of the perimeter portion and the center portion and terminates on a top surface of a head panel of the foundation structure on the perimeter portion in contact with the acoustic panel when in a down position.

23. The bed system of claim 21, wherein the fabric deck panel cover further comprises:

a central portion covering the center portion of the foundation structure;

a perimeter portion surrounding the central portion covering the perimeter portion of the foundation structure; and the flap comprises a sensor portion positioned along a head edge of the perimeter portion of the fabric deck panel cover.

24. The bed system of claim 23, wherein:

the foundation structure further comprises a deck panel coupled to a head panel of the foundation structure, the deck panel defining a deck edge of the perimeter portion; and the perimeter portion surrounds an entirety of the perimeter portion of the head panel and the deck panel.

25. The bed system of claim 24, wherein:

the perimeter portion is attached to the deck panel and the head panel by one or more of staples or adhesives; and the sensor portion is attached to the head panel by one or more of grommets, snaps, screws, or hook-and-loop fasteners.

26. The bed system of claim 23, wherein the sensor portion is trapezoidal.

27. The bed system of claim 23, wherein the sensor portion extends past the at least one sensor to the head edge.

28. The bed system of claim 23, wherein the flap is detachable from the fabric deck panel cover.

29. The bed system of claim 19, wherein the at least one sensor comprises at least one of an acoustic sensor, a ribbon-type acoustic sensor, a microphone, or a piezoelectric sensor, the at least one sensor oriented outward away from the side surface of the foundation structure.

30. A bed system comprising:

a foundation structure comprising one or more panels configured to support a mattress, the foundation structure defining a perimeter portion about a center portion;

at least one sensor positioned in the perimeter portion of the one or more panels, the at least one sensor configured to detect a sound indicative of a snore received at the perimeter portion;

a fabric deck panel cover configured to cover a top surface of the foundation structure and a portion of a side surface of the foundation structure, wherein the fabric deck panel cover comprises:

an acoustic panel positioned along a head edge of a perimeter portion of the fabric deck panel cover, the acoustic panel covering a side portion of the at least one sensor comprising an acoustic sensor, wherein the acoustic panel comprises a first fabric different than a second fabric comprising the perimeter portion, the first fabric configured to be suitable for covering the acoustic sensor while still allowing the acoustic sensor to detect the sound indicative of the snore at the side surface of the foundation structure, the sound indicative of the snore originating from a sleeper on the mattress; and a flap that is positioned and configured to be opened to allow for access to the at least one sensor, the flap extending from the center portion to the side surface of the foundation structure, the flap comprising a sensor portion positioned along the head edge of the perimeter portion of the fabric deck panel cover, wherein an end of the flap is offset from and extends past the acoustic panel to couple to a bottom surface of a head panel of the foundation structure; and a controller configured to perform operations comprising: receiving a signal from the at least one sensor indicative of the snore from the at least one sensor; and determining a position of a snoring person based, at least in part, on the signal indicative of the snore.

31. A bed system comprising:

a foundation structure comprising one or more panels configured to support a mattress, the foundation structure defining a perimeter portion about a center portion;

at least one sensor positioned in the perimeter portion of the one or more panels, the at least one sensor configured to detect a sound indicative of a snore received at the perimeter portion, wherein the at least one sensor comprises a housing and an acoustic sensor, the housing having a top surface aligned with the top surface of the foundation structure and a side surface aligned with the side surface of the foundation structure, the acoustic sensor mounted on the side surface of the housing;

a fabric deck panel cover configured to cover a top surface of the foundation structure and a portion of a side surface of the foundation structure, wherein the fabric deck panel cover comprises:

a central portion covering the center portion of the foundation structure;

a perimeter portion surrounding the central portion and covering the perimeter portion of the foundation structure;

a flap that is positioned and configured to be opened to allow for access to the at least one sensor, the flap extending from the center portion to the side surface of the foundation structure, the flap comprising:

a sensor portion positioned along a head edge of the perimeter portion of the fabric deck panel cover; and an acoustic panel, wherein the flap is configured to position the acoustic panel on the head edge on the side surface of the foundation structure when the flap is attached to the side surface of the foundation structure, wherein the acoustic panel comprises a first fabric different than a second fabric comprising the perimeter portion, the first fabric configured to be suitable for covering the acoustic sensor while still allowing the acoustic sensor to detect the sound indicative of the snore at the side surface of the foundation structure, the sound indicative of the snore originating from a sleeper on the mattress; and a controller configured to perform operations comprising: receiving a signal from the at least one sensor indicative of the snore from the at least one sensor; and determining a position of a snoring person based, at least in part, on the signal indicative of the snore.

32. A bed system comprising:

a foundation structure comprising one or more panels configured to support a mattress, the foundation structure defining a perimeter portion about a center portion;

at least one sensor positioned in the perimeter portion of the one or more panels, the at least one sensor configured to detect a sound indicative of a snore received at the perimeter portion, wherein the at least one sensor comprises an acoustic sensor, a housing, and a gasket, the housing defining a penetration to accept the acoustic sensor and the gasket surrounding the penetration, the gasket configured to prevent fluid ingress past the acoustic sensor into the housing;

a fabric deck panel cover configured to cover a top surface of the foundation structure and a portion of a side surface of the foundation structure, wherein the fabric deck panel cover comprises a flap that is positioned and configured to be opened to allow for access to the at least one sensor, the flap extending from the center portion to the side surface of the foundation structure; and a controller configured to perform operations comprising: receiving a signal from the at least one sensor indicative of the snore from the at least one sensor; and determining a position of a snoring person based, at least in part, on the signal indicative of the snore.

33. The bed system of claim 32, wherein the fabric deck panel cover further comprises an acoustic panel positioned along a head edge of the perimeter portion of the fabric deck panel cover, the acoustic panel covering a side portion of the at least one sensor comprising the acoustic sensor, wherein the acoustic panel comprises a first fabric different than a second fabric comprising the perimeter portion, the first fabric configured to be suitable for covering the acoustic sensor while still allowing the acoustic sensor to detect the sound indicative of the snore at the side surface of the foundation structure, the sound indicative of the snore originating from a sleeper on the mattress.

* * * * *